United States Patent [19]
Semple et al.

[11] Patent Number: 6,034,215
[45] Date of Patent: *Mar. 7, 2000

[54] 3-AMINO-2-OXO-1-PIPERIDNERCETIC DERIVATIVES AS ENZYME INHIBITORS

[75] Inventors: Joseph Edward Semple, San Diego; Robert John Ardecky, Encinitas; Ruth Foelsche Nutt; William Charles Ripka, both of San Diego; David C. Rowley, Encinitas; Marguerita S. L. Lim-Wilby, La Jolla; Terence Kevin Brunck, San Diego, all of Calif.

[73] Assignee: Corvas International, Inc., San Diego, Calif.

[*] Notice: This patent is subject to a terminal disclaimer.

[21] Appl. No.: 08/950,270

[22] Filed: Oct. 14, 1997

Related U.S. Application Data

[63] Continuation of application No. 08/484,720, Jun. 7, 1995, Pat. No. 5,703,208, which is a continuation-in-part of application No. 08/261,378, Jun. 17, 1994, abandoned, and application No. 08/356,831, Dec. 13, 1994, abandoned.

[51] Int. Cl.$^7$ .................................................. A61K 38/06
[52] U.S. Cl. ........................ 530/331; 540/463; 540/487; 540/524; 540/527; 546/24; 546/192; 546/243; 548/413; 548/517; 548/547; 514/18; 514/19; 514/20
[58] Field of Search .............................. 530/331; 514/18, 514/19; 540/463, 527; 546/184, 192; 548/535

[56] References Cited

U.S. PATENT DOCUMENTS 5,703,208 12/1997 Semple .................................... 530/331

*Primary Examiner*—Michael P. Woodward
*Assistant Examiner*—David Lukton
*Attorney, Agent, or Firm*—Lyon & Lyon LLP

[57] ABSTRACT

The present invention discloses peptide aldehydes which are potent and specific inhibitors of thrombin, their pharmaceutically acceptable salts, pharmaceutically acceptable compositions thereof, and methods of using them as therapeutic agents for disease states in mammals characterized by abnormal thrombosis.

18 Claims, 13 Drawing Sheets ized by abnormal thrombosis.

3-AMINO-2-OXO-1-PIPERIDNERCETIC DERIVATIVES AS ENZYME INHIBITORS

CROSS-REFERENCE TO RELATED APPLICATIONS

This is a continuation of application Ser. No. 08/484,720 filed Jun. 7, 1995, hereby incorporated by reference herein in its totality which is a Continuation-in-Part of U.S. Ser. No. 08/261,378, filed Jun. 17, 1994, now abandoned and U.S. Ser. No. 08/356,831, filed Dec. 13, 1994, now abandoned the disclosures of which are incorporated herein by reference.

TECHNICAL FIELD

In one aspect, the present invention relates compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals character-

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

P4 P3 P2 P1 P1'

Gly-Gly-Val-Arg/Gly Fibrinogen Aα Chain

Phe-Ser-Ala-Arg/Gly Fibrinogen Bβ Chain

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284

(published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-L-argininal]-2-piperidinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombin by binding to both its anion-binding exo-site and to its catalytic active site which are distinct and physically distant from each other. Rydel, T. J. et al., Science, 249: 277 (1990). Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 264: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exosite. Liu, L. W. et al., J. Biol. Chem, 266: 16977 (1991). Hirugen also is reported to block thrombin-mediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

SUMMARY OF THE INVENTION

The present invention is directed to novel compounds which are peptide argininals which incorporate lactam groups which are potent inhibitors of thrombin in vivo and in vitro.

Thus, in one aspect, the present invention is directed to compounds of the formula:

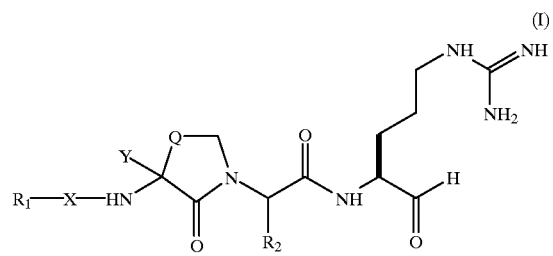

wherein
(a) X is selected from the group consisting of —S(O)$_2$—N(R')—S(O)$_2$—, —(C=O)—, —OC(=O)—, —NH—C(=O)—, —P(O)(R")—and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;
(b) R$_1$ is selected from the group consisting of:
(1) alkyl of 1 to about 12 carbon atoms,
(2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons,
(3) cyclic alkyl of 3 to about 15 carbon atoms, which optionally is substituted in the ring carbons with hydroxyl, amino, guanidino, amidino, or alkoxyl or alkyl each of which is 1 to about 3 carbons,
(4) heterocycloalkyl of 4 to about 10 ring atoms with the ring atoms selected from carbon and heteroatoms, wherein the heteroatoms are selected from the group consisting of oxygen, nitrogen, and S(O)i, wherein i is 0, 1, or 2, optionally substituted in the ring carbons with hydroxyl, alkoxyl or alkyl each of which is 1 to about 3 carbons, amino, guanidino, or amidino,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which is 1 to about 3 carbons, amino, guanidino, or amidino,
(6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons, (7) aryl of about 6 to about 14 carbon atoms which is optionally mono-, di- or tri-substituted with $Y_1$, $Y_2$, and/or $Y_3$, respectively, (8) heteroaryl of 5 to 14 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively, (9) aralkyl of about 7 to about 15 carbon atoms which is optionally mono-, di-, or tri-substituted in the aryl ring with $Y_1$, $Y_2$, and/or $Y_3$, respectively,

(10) heteroaralkyl of 6 to 11 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively,

(11) aralkenyl of about 8 to about 15 carbon atoms which is optionally mono-, di-, or tri-substituted in the aryl ring with $Y_1$, $Y_2$, and/or $Y_3$, respectively,

(12) heteroaralkenyl of 7 to 12 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively,

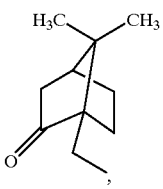

(13)

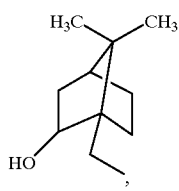

(14)

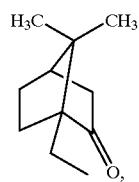

(15)

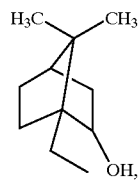

(16)

(17) perfluoroalkyl of 1 to about 12 carbon atoms
(18) perfluoroaryl of about 6 to about 14 carbon atoms,
(19) perfluoroaralkyl of about 7 to about 15 carbon atoms,
(20) hydrogen, and (21)

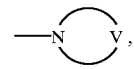

wherein

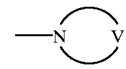

is a 5 to 7 member heterocycle of 3 to 6 ring carbon atoms, where V is —$CH_2$—, —O—, —S(=O)—, —$S(O)_2$—or —S—, wherein $Y_1$, $Y_2$, and $Y_3$ are (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)_{OZ_1}$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$, and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —$OC(Z_3)(Z_4)O$, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) Q is —$(CH_2)_n$—, wherein n is an integer from 1 to 4, or —$(CH_2)_q{}^R4$, wherein q is 1 or 2, and $R_4$ is —$S(O)_p$—, O N($R_5$), wherein p is 0, 1, or 2 and $R_5$ is selected from the group consisting of hydrogen, alkyl of 1 to 4 carbon atoms, and aryl of 1 to 4 carbon atoms;

(d) $R_2$ is selected from the group consisting of hydrogen, alkyl of 1 to 4 carbon atoms or alkenyl of 2 to 4 carbon atoms; and (e) Y is selected from the group of $R_1$ substituents, with the proviso that Y is not

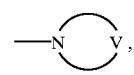

and pharmaceutically acceptable salts thereof.

Among other factors, the present invention is based on our finding that the novel compounds of our invention are active as selective inhibitors of thrombin in vivo and in vitro. In addition, we have found that certain of the preferred compounds of the present invention exhibit advantageous selectivity in that they are very potent inhibitors of thrombin but are inactive or significantly less active, (several orders of magnitude less) in inhibiting plasmin and are significantly less active in inhibiting trypsin. This selectivity for inhibition of thrombin gives these compounds a therapeutic advantage in treating or preventing thrombosis in a mammal suspected of having a condition characterized by abnormal thrombosis.

Peptidyl arginine aldehydes have been reported to exist in equilibrium structures in aqueous solutions. Bajusz, S., et al., J. Med. Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all the equilibrium forms.

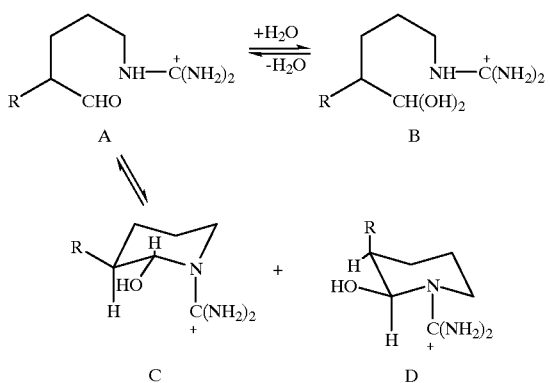

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound the present invention or pharmaceutical composition comprising such a compound.

DEFINITIONS

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, picolyl, and the like, all of which may be optionally substituted.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to natural amino acids, unnatural amino acids, and amino acid analogs in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent;

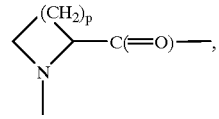

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

"Cycloalkenyl" refers to a cyclic alkenyl group. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to CH2.

The term "halogen" refers to fluorine, chlorine, bromine and iodine.

"Heteroaralkenyl" refers to an alkenyl group substitued with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. "Heteroaralkyl" refers to an alkyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. "Heteroaryl" refers to aryl groups having from 1 to 9 carbon atoms and the remainder of the atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, S(O)i, wherein i is 0–2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

The term "lower" referred to herein in connection with organic radicals or compounds defines such with up to and including 5, preferably up to and including 4 and advantageously one or two carbon atoms. Such groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroaryl alkyl" refers an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "Arg-al" refers to the residue of L-argininal which has the formula:

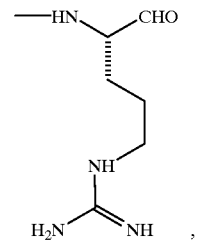

The term "Arg-ol" refers to the residue of L-argininol which has the formula:

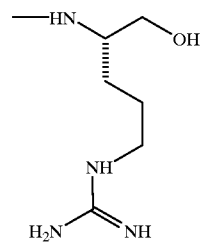

"(S)-N$^g$-nitroargininol hydrochloride" refers to the compound which has the formula:

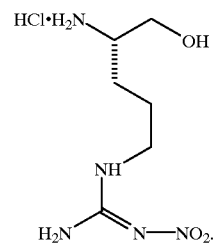

"N-alpha-t-butoxycarbonyl-N$^g$-nitro-L-arginine" refers to the compound which has the formula:

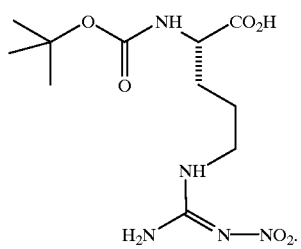

The term "homoAla(cyclo)-Gly" refers to the residue of (S)-3-amino-2-oxo-1-pyrrolidinacetic acid which has the formula:

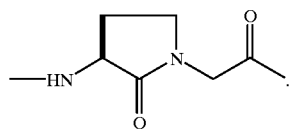

The term "norVal(cyclo)-Gly" refers to the residue of (S)-3-amino-2-oxo-1-piperidineacetic acid which has the formula:

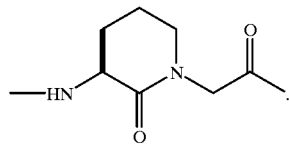

The term "norLeu(cyclo)-Gly" refers to the residue of (R)- or (S)-3-amino-2-oxo-hexahydro-1-azepineacetic acid which has the formula:

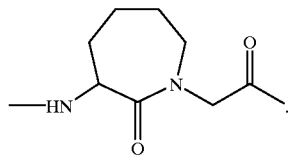

In addition, the following abbreviations stand for the following:

"Boc" refers to t-butoxycarbonyl.

"BzlSO$_2$" refers to benzylsulfonyl.

"Cbz" refers to benzyloxycarbonyl.

"DCC" refers to N,N'-dicyclohexylcarbodiimide.

"EDC" refers to 1-ethyl-3-(3-dimethylamino-propyl) carbodiimide hydrochloride salt.

"HBTU" refers to 2-(1H-benzotriazol-1-yl)-1,1,3,3-tetramethyluronium hexafluorophosphate.

"HCl" refers to hydrochloric acid.

"HPLC" refers to high pressure liquid chromatography.

"HOBt" refers to 1-hydroxybenzotriazole monohydrate.

"LiAlH$_4$" refers to lithium aluminum hydride.

"LiAlH$_2$(OEt)$_2$" refers to lithium aluminum dihydride diethoxide.

"THF" refers to tetrahydrofuran.

"TLC" refers to thin layer chromatography.

DETAILED DESCRIPTION OF THE INVENTION

Figure 1:
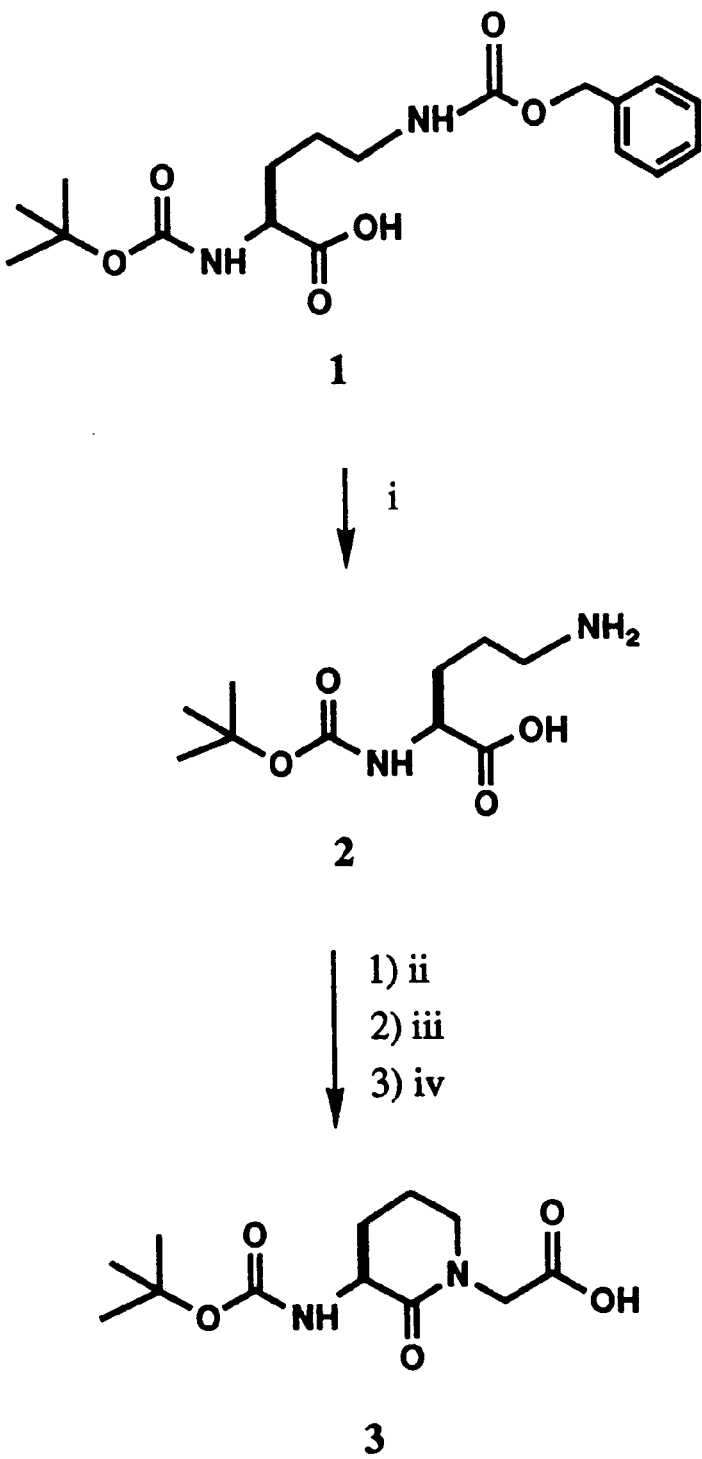
FIG. 1 depicts the reaction scheme for preparation of an intermediate used for the synthesis of the compounds of the present invention. In this figure, "i" through "iv" are defined as: i) hydrogen gas, 10% palladium on carbon; ii) glyoxylic acid; iii) hydrogen gas, 10% palladium on carbon; and iv) 50–60° C., N,N-dimethylformamide.

1. Preferred Compounds
   Compounds of the present invention have the formula:

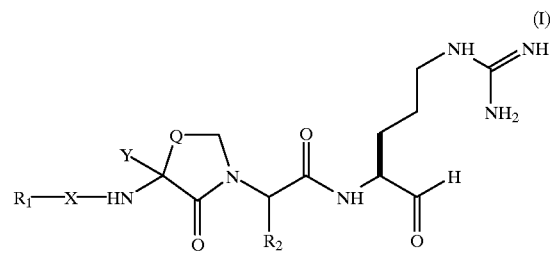

(I)

wherein
(a) X is selected from the group consisting of —S(O)$_2$——N(R')—S(O)$_2$—, —(C=O)—, —OC(=O)—, —NH—C(=O)—, —P(O)(R")—and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;
(b) R$_1$ is selected from the group consisting of:
   (1) alkyl of 1 to about 12 carbon atoms,
   (2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons,
   (3) cyclic alkyl of 3 to about 15 carbon atoms, which optionally is substituted in the ring carbons with hydroxyl, amino, guanidino, amidino, or alkoxyl or alkyl each of which is 1 to about 3 carbons,
   (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which is 1 to about 3 carbons, amino, guanidino, or amidino,
   (5) heterocyclo of 4 to about 10 ring atoms with the ring atoms selected from carbon and heteroatoms, wherein the heteroatoms are selected from the group consisting of oxygen, nitrogen, and S(O)i, wherein i is 0, 1, or 2, optionally substituted in the ring carbons with hydroxyl, alkoxyl or alkyl each of which is 1 to about 3 carbons, amino, guanidino, or amidino,
   (6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons,
   (7) aryl of about 6 to about 14 carbon atoms which is optionally mono-, di- or tri-substituted with Y$_1$, Y$_2$, and/or Y$_3$, respectively,
   (8) heteroaryl of 5 to 14 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively, (9) aralkyl of about 7 to about 15 carbon atoms which is optionally mono-, di-, or tri-substituted in the aryl ring with $Y_1$, $Y_2$, and/or $Y_3$, respectively,

(10) heteroaralkyl of 6 to 11 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively,

(11) aralkenyl of about 8 to about 15 carbon atoms which is optionally mono-, di-, or tri-substituted in the aryl ring with $Y_1$, $Y_2$, and/or $Y_3$, respectively,

(12) heteroaralkenyl of 7 to 12 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively,

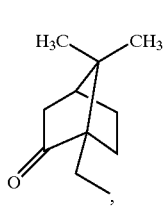

(13)

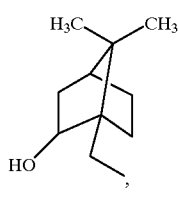

(14)

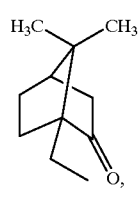

(15)

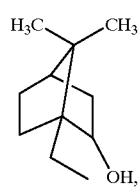

(16)

(17) perfluoroalkyl of 1 to about 12 carbon atoms,

(18) perfluoroaryl of about 6 to about 14 carbon atoms,

(19) perfluoroaralkyl of about 7 to about 15 carbon atoms,

(20) hydrogen, and (21)

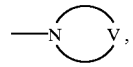

wherein

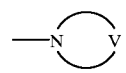

is a 5 to 7 member heterocycle of 3 to 6 ring carbon atoms, where V is —$CH_2$—, —O—, —S(=O)—, —$S(O)_2$— or —S—, wherein $Y_1$, $Y_2$, and $Y_3$ are (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$, and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) Y1 and Y2 are selected together to be —$OC(Z_3)(Z_4)O$, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) Q is —$(CH_2)_n$—, wherein n is an integer from 1 to 4, or —$(CH_2)_qR_4$-, wherein q is 1 or 2, and $R_4$ is —$S(O)_p$—, —O—, —$N(R_5)$—, wherein p is 0, 1, or 2 and $R_5$ is selected from the group consisting of hydrogen, alkyl of 1 to 4 carbon atoms, and aryl of 1 to 4 carbon atoms;

(d) R2 is selected from the group consisting of hydrogen, alkyl of 1 to 4 carbon atoms or alkenyl of 2 to 4 carbon atoms; and (d) Y is selected from the group of $R_1$ substituents, with the proviso that Y is not

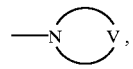

and pharmaceutically acceptable salts thereof.

Preferred X groups include a direct link, —$SO_2$—, —NH—$S(O)_2$, and —N(R')—$S(O)_2$—. Especially preferred X groups include a direct link and —$SO_2$—.

Preferred $R_1$ groups include alkyl, aralkyl and aryl groups. Suitable aryl groups include substituted or unsubstituted phenyl and naphthyl. Preferred aryl substituents include, —$C(O)OH$, —$C(O)OZ_1$, —$CH_3$, —$OCH_3$, and —$CF_3$. Meta and/or ortho substitutions are preferred. Especially preferred $R_1$ groups include aralkyl groups. Particularly preferred $R_1$ groups include substituted or unsubstituted benzyl groups. Cyclohexyl and cyclohexylmethyl are especially preferred $R_1$ groups.

Preferred are compounds where Q is —(CH$_2$)$_2$— or —(CH$_2$)$_3$—

Preferred R$_2$ groups include hydrogen.

Preferred Y groups are selected from the group consisting of
(1) hydrogen,
(2) phenyl-(CH2)$_i$—, wherein i is an integer from 0 to 3, and the phenyl is optionally mono-, di-, or tri-substituted with with Y$_1$, Y$_2$, and/or Y$_3$, respectively, as defined above,
(3) heteroaryl-(CH$_2$)$_i$—, wherein i is an integer from 0 to 3, and the heteroaryl is optionally mono-, di-, or tri-substituted with Y$_1$, Y$_2$, and/or Y$_3$, respectively, as defined above,
(4) heterocycloalkyl —(CH$_2$)$_i$—, wherein i is an integer from 0 to 3, and the heterocycloalkyl is optionally substituted with hydroxyl, alkoxyl or alkyl each of which is 1 to about 3 carbons,
(5) C$_5$ to C$_8$ cycloalkenyl, optionally substituted with Z$_5$, Z$_6$, and/or Z$_7$, as defined below, (6) C$_5$ to C$_8$ cycloalkyl, optionally mono-, di-, or tri-substituted with with Z$_5$, Z$_6$, and/or Z$_7$, respectively, wherein Z$_5$, Z$_6$, and/or Z$_7$ are independently selected from the group consisting of R$_5$, OR$_5$, and C$_{O2}$R$_5$, wherein R$_5$ is selected from the group consisting of hydrogen, methyl, alkyl of 1–3 carbon atoms,
(7) (CH$_2$)$_b$—Z$_5$, wherein b is 0 to 6 and Z$_5$ is as defined above.

More preferred Y groups include aralkyl or cycloalkyl groups. Particularly preferred are substituted or unsubstituted benzyl and 1-naphthylmethyl groups. Preferred aromatic substituents include —C(O)OH, —C(O)OZ$_1$, —CH$_3$, —OCH$_3$, and —CF$_3$. Meta and/or ortho substituents are preferred. Preferred cycloalkyl groups include those containing 5–8 ring carbons. Preferred cycloalkyl substitutents include —C(O)OH, —C(O)OZ$_1$, —CH$_3$, —OCH$_3$.

According to a particularly preferred aspect, provided are compounds of formula I wherein X is —S(O)$_2$—, R$_1$ is substituted or unsubstituted aralkyl, Q is —(CH$_2$)$_2$—and R$_2$ is hydrogen. A very preferred aspect is directed to such compounds where R$_1$ is substituted or unsubstituted benzyl.

According to another particularly preferred aspect, provided are compounds wherein X is —S(O)$_2$—, R$_1$ is substituted or unsubstituted aralkyl, Q is —(CH$_2$)$_3$— and R$_2$ is hydrogen. A very preferred aspect is directed to such compounds where R$_1$ is substituted or unsubstituted benzyl.

Preferred compounds of this invention include those whose synthesis is described in Examples 8 (and 18), 26, 34, 36(a) through 36(y), 40(b), 55, 64, 72(a) and 72(b), 80, and 82(a) through 82(f).

Especially preferred compounds of the present invention include
N-benzylsulfonyl-norVal(cyclo)-Gly-L-argininal (Example 8, 18),
N-(norVal(cyclo)-Gly-L-argininal (Example 40(b),
D,L-α-benzyl-norVal(cyclo)Gly-L-argininal (Example 55),
D,L-α-benzyl-norLeu(cyclo)Gly-L-argininal (Example 64)
N-(1-naphthyl-SO$_2$-norVal(cyclo)-Gly-L-argininal (Example 82a),
N-(BnSO$_2$-norLeu(cyclo)-Gly)-L-argininal (Example 34),
N-(2-carbomethoxybenzyl-SO$_2$-norLeu(cyclo)-Gly)-L-argininal (Example 36(e)),
N-(2-trifluoromethylbenzyl-SO$_2$-norLeu(cyclo)-Gly)-L-argininal (Example 36(g)),
N-(cyclohexylmethyl-SO$_2$-norLeu(cyclo)-Gly)-L-argininal (Example 36(i)),
N-(2-thiophenemethyl-SO$_2$-norLeu(cyclo)-Gly)-L-argininal (Example 36(k)),
N-(phenylamino-SO$_2$-norLeu(cyclo)-Gly)-L-argininal (Example 36(n)),
N-(3-carbomethoxybenzyl-SO$_2$-norLeu(cyclo)-Gly)-L-argininal (Example 36(o)),
N-(3-trifluoromethylbenzyl-SO$_2$-norLeu(cyclo)-Gly)-L-argininal (Example 36(p)),
N-(2-methylbenzyl-SO$_2$-norLeu(cyclo)-Gly)-L-argininal (Example 36(q)),
N-(3-methylbenzyl-SO$_2$-norLeu(cyclo)-Gly)-L-argininal (Example 36(r)),
N-(3-methoxybenzyl-SO$_2$-norLeu(cyclo)-Gly)-L-argininal (Example 36(t)),
N-(2-chlorobenzyl-SO$_2$-norLeu(cyclo)-Gly)-L-argininal (Example 36(u)),
N-($^2$-methyl-5-fluorobenzyl-SO$_2$-norLeu(cyclo)-Gly)-L-argininal (Example 36(w)),
N-($^2$-methyl-5-methoxybenzyl-SO$_2$-norLeu(cyclo)-Gly)-L-argininal (Example 36(x)),
N-[(S)-3-N-phenylethylamino-2-oxo-1-piperidineacetyl]-L-argininal (Example 72a),
N-[(S)-3-N-phenylpropylamino-2-oxo-1-piperidineacetyl]-L-argininal (Example 72b), and
N-[(S)-3-N-phenylethylamino-hexahydro-2-oxo-azepine-1-acetyl]-L-argininal (Example 80).

According to another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of trifluoroacetic acid, hydrochloric acid, hydrobromic acid, acetic acid, benzene sulfonic acid and other suitable acid addition salts.

In formula I, carbon atoms bearing the R$_2$ and Y groups are capable of forming stereoisomers. This invention contemplates both stereoisomeric forms.

2. Preparation of Preferred Compounds

Certain intermediates of the present invention are used in the preparation of the compounds of the present invention. For example, (S)-3-[(tert-butoxycarbonyl)amino]-2-oxo-1-piperidineacetic acid of Example 1, (S)-3-[(tert-butoxycarbonyl)amino]-2-oxo-1-pyrrolidineacetic acid of Example 21, and (S)-3-[(tert-butoxycarbonyl)amino]-2-oxo-hexahydroazepineacetic acid, benzyl ester of Example 28.

FIG. 1 exemplifies a preferred reaction scheme for the preparation of one preferred intermediate 3 used in the preparation of the compounds of the present invention. Example 1 provides the details of the preferred scheme.

As shown in FIG. 1, N-alpha-Boc-N-delta-benzyloxycarbonyl-L-ornithine 1 is hydrogenated with hydrogen gas and palladium on carbon to give 2, which is then reacted with glyoxylic acid, hydrogenated with hydrogen gas and palladium on carbon, and heated at an elevated temperature to give 3.

Figure 2:
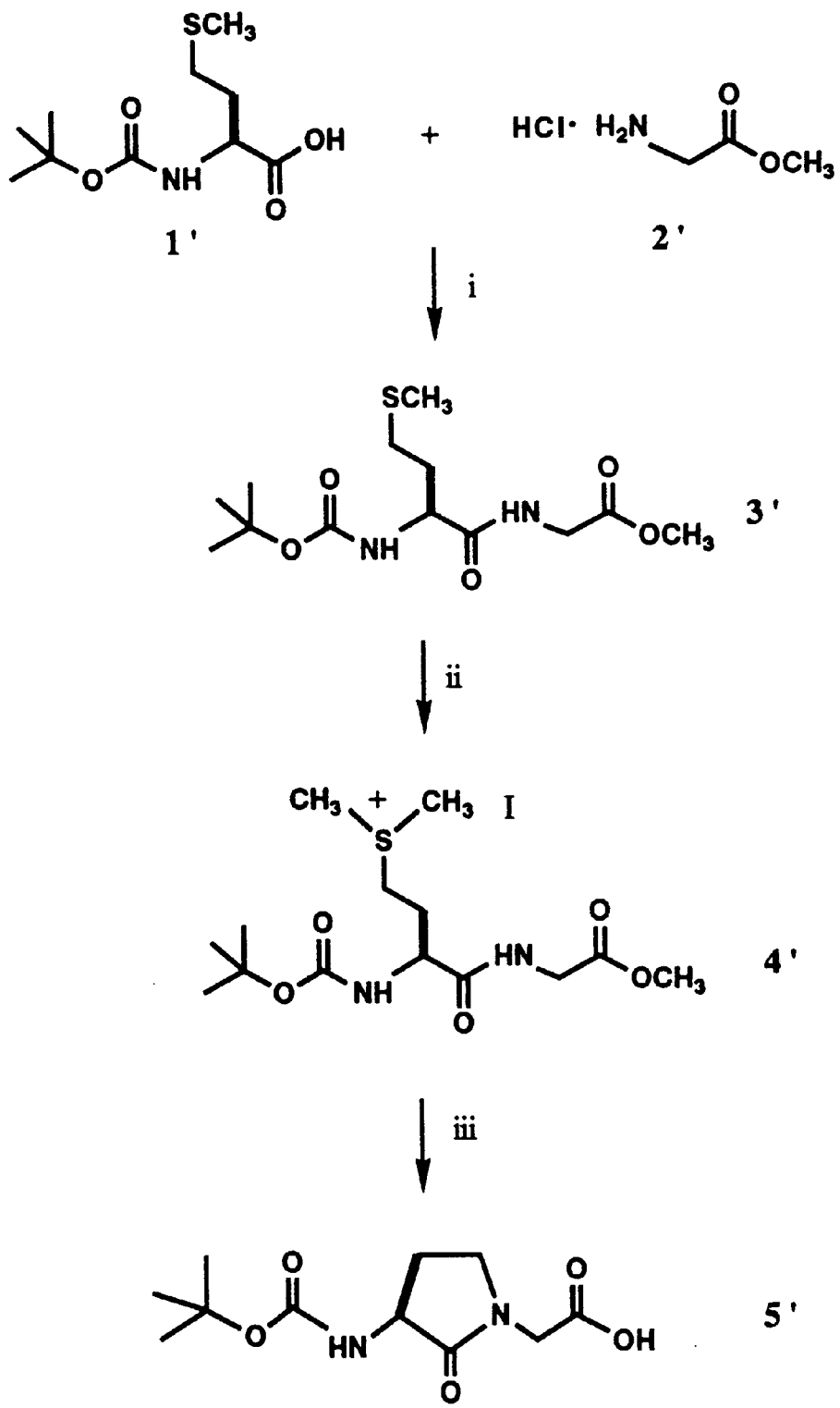
FIG. 2 depicts the reaction scheme for preparation of an intermediate used for the synthesis of the compounds of the present invention. In this figure, "i" through "iii" are defined as: i) HOBt, DCC and triethylamine; ii) methyl iodide; and iii) sodium hydride later followed by ethyl acetate and water.

FIG. 2 exemplifies a preferred reaction scheme for the preparation of one preferred intermediate, 5', used in the preparation of the compounds of the present invention. Examples 19 through 21 provide the details of the preferred scheme.

As shown in FIG. 2, N-alpha-Boc-L-methionine 1' and glycine methyl ester hydrochloride 2' are coupled by use of a carbodiimide and HOBt to give 3'. The sulfur atom on the methionine side chain of 3' is alkylated with methyl iodide to give 4'. Finally, 4' is treated with sodium hydride which results in cyclization to give 5'.

Figure 3:
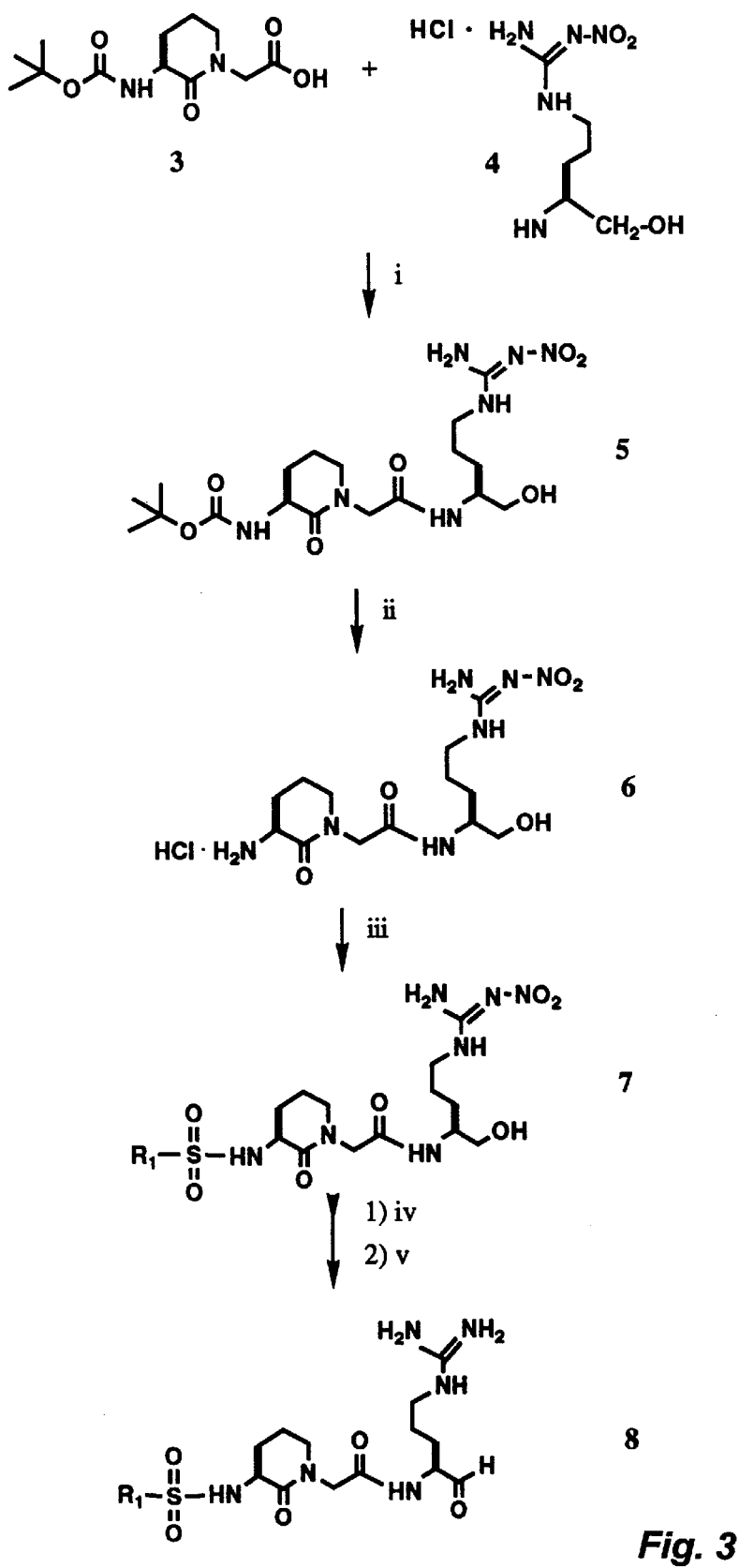
FIG. 3 depicts a preferred reaction scheme for a synthesis of certain compounds of the present invention. In this figure, "i" through "v" are defined as: i) HOBt, EDC, 4-methylmorpholine; ii) 1N HCl in ethyl acetate; iii) potassium carbonate, R$_1$—SO$_2$Cl wherein R$_1$ is as defined herein; iv) hydrogen gas, 10% palladium on carbon; and v) dimethylsulfoxide, toluene, dichloroacetic acid and EDC.
Figure 4:
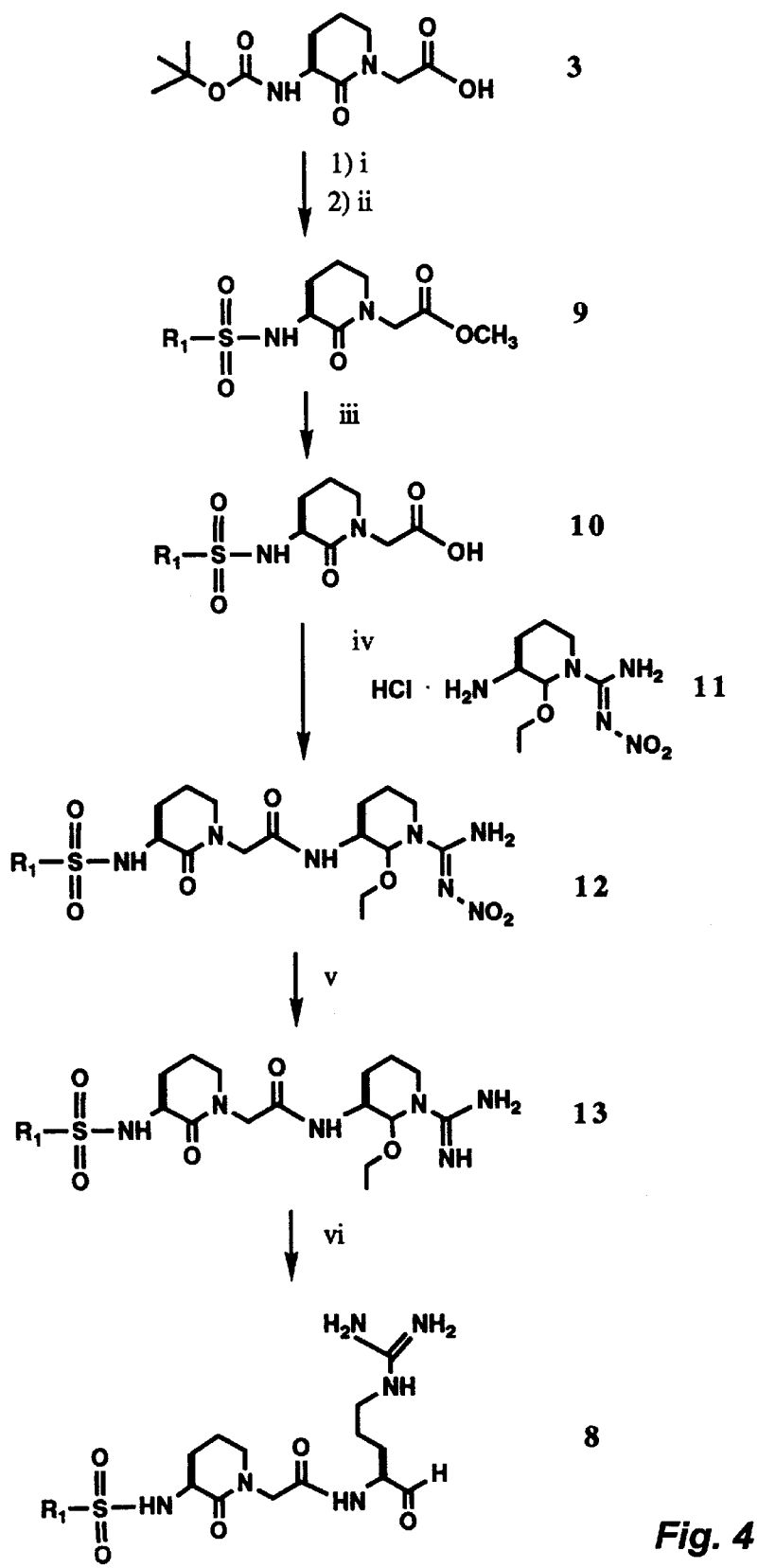
FIG. 4 depicts a preferred reaction scheme for a synthesis of certain compounds of the present invention. In this figure, "i" through "vi" are defined as: i) methanol saturated with HCl; ii) triethylamine, R-SO$_2$Cl wherein R is alkyl, aryl or aralkyl; iii) 1.0M lithium hydroxide; iv) HOBt, N,N-diisopropylethylamine, EDC; v) hydrogen gas, 10% palladium on carbon; and vi) 3N HCl.

The compounds of the present invention may be prepared by the preferred reaction schemes depicted in FIGS. 3 and 4. Examples 2 through 8 provide the details of the preferred scheme of FIG. 3, while Examples 9 through 18 provide the same for the preferred scheme of FIG. 4.

In either reaction scheme, intermediates, which include 3 and 5' shown in FIGS. 1 and 2, respectively, are coupled to argininal moieties to eventually give the compounds of the present invention.

For example, as shown in FIG. 3, 3 is coupled to ((S)—N$^g$—nitroargininol hydrochloride 4 (prepared from (S)—N—alpha-Boc-N$^g$-nitroarginine as disclosed in Examples 2 through 3) by carbodiimide coupling to give 5. 5 is treated with hydrogen chloride to remove the Boc group to give the hydrochloride 6, which is then reacted with a sulfonyl chloride, depicted by $R_1$—$S(O)_2$—Cl, to give 7. $R_1$ is as defined herein. 7 is hydrogenated with hydrogen gas and palladium on carbon to remove the N$^g$-nitro group, then the hydroxy group is oxidized using dimethylsulfoxide, dichloroacetic acid, toluene and EDC to give 8.

Alternatively, as shown in FIG. 4, treatment of 3 with saturated HCl in an alcohol removes its Boc group and converts its carboxy group to an ester, whose free amino group is then reacted with a sulfonyl chloride, depicted by $R_1$—$S(O)_2$—Cl to give 9. $R_1$ is as defined herein. 9 is base hydrolysed to give 10 which has a free carboxy group. 10 is coupled to 11 (prepared as described in Examples 12 through 15) by carbodiimide coupling to give 12. 12 is hydrogenated with hydrogen gas and palladium on carbon to give 13. 13 is hydrolyzed in aqueous acid to also give 8.

The preferred means of chemically coupling (as for example, 3 to 5 of FIG. 3 or 10 to 12 of FIG. 4) include formation of a peptide bond by using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling include DCC with HOBt, EDC with HOBt, HBTU or TBTU. In two-step coupling, an activated ester or anhydride of the C-terminal carboxy group of one coupling partner is formed prior to its coupling to the other coupling partner.

Figure 6:
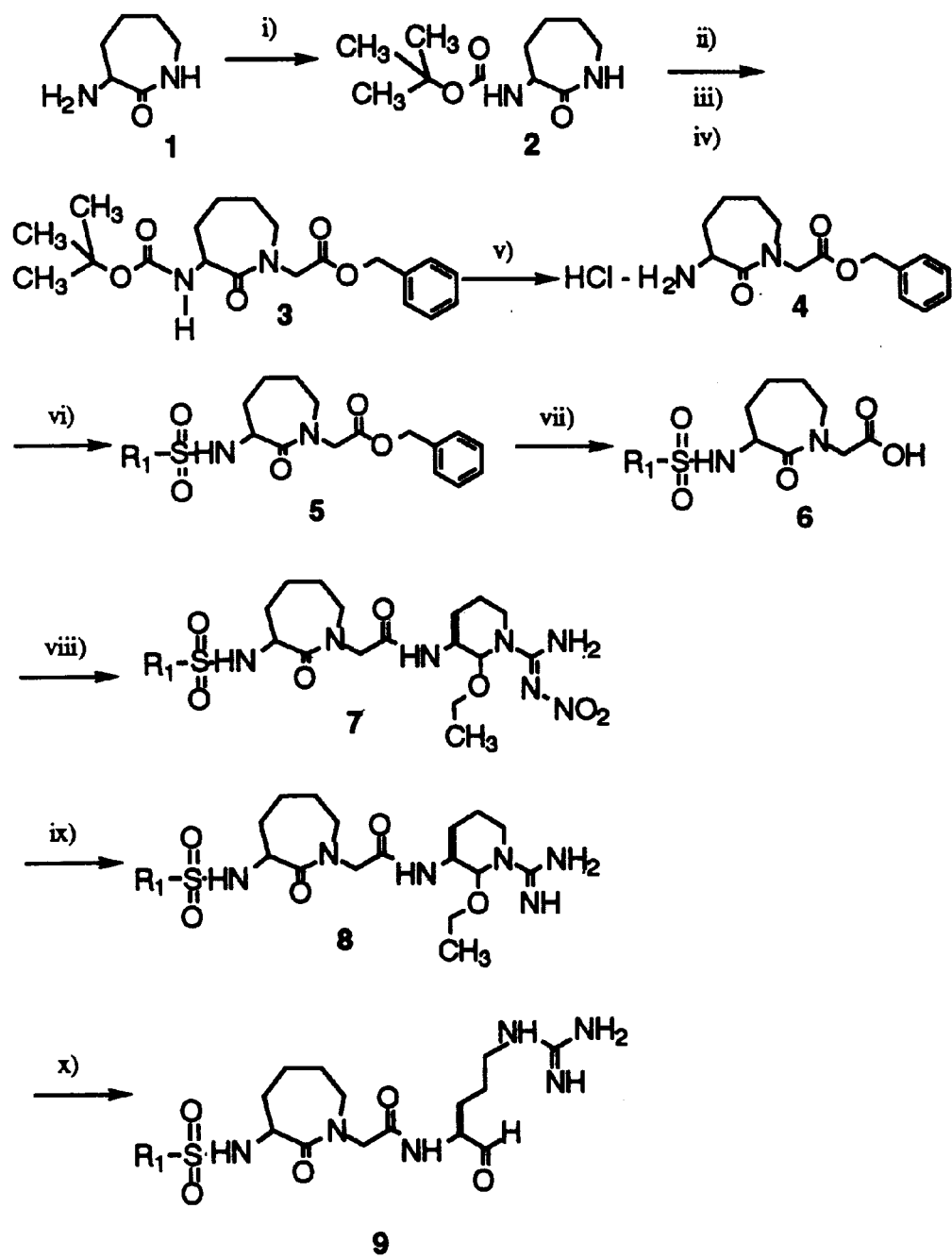
FIG. 6 depicts a preferred reaction scheme for the preparation of certain compounds of the present invention. In this figure, i)-x) are defined as: i) di-t-butyl dicarbonate, sodium bicarbonate in tetrahydrofuran and water; ii) lithium bis (trimethylsilyl)amide and tetrahydrofuran; iii) benzyl bromoacetate; iv) ammonium chloride; v) HCl and ethyl acetate; vi) triethylamine, acetonitrile and R$_1$—SO$_2$—Cl, where R$_1$ is as defined herein; vii) hydrogen, palladium on carbon and ethanol; viii) acetonitrile, N$^g$-nitro-L-argininal ethyl cyclol, hydrochloride salt, 1-hydroxybenzotriazole monohydrate, 1-ethyl-3-(3-dimethylaminopropyl) carbodiimide hydrochloride salt and N,N-diisopropylethylamine; ix) hydrogen gas, palladium on carbon, ethanol, acetic acid and water; and x) 3N HCl and HPLC purification.

The compounds of the present invention also may be prepared by the preferred reaction scheme depicted in FIG. 6. Examples 12 through 15 and 27 through 34 provide the details of this preferred scheme.

As shown in FIG. 6, the amine of D— (alpha)— or L—(—)—alpha-amino-epsilon-caprolactam 1.1 is protected by treatment with di-t-butyldicarbonate and sodium bicarbonate in THF and water to give 2.1, which is then reacted with lithium bis(trimethylsilyl)amide in THF, followed by benzyl bromoacetate. The reaction is quenched with a saturated ammonium chloride solution to give 3.1.

The Boc protecting group of 3.1 is then removed by treatment with 5 N HCl in ethyl acetate to provide the HCl salt 4.1, which is then reacted with triethylamine and $R_1SO_2Cl$ in acetonitrile to give the sulfonamide 5.1. 5.1 is 5 then hydrogenated with hydrogen gas and palladium on carbon in a Parr Shaker to give 6.1. 6.1 is coupled to N$^g$-nitro-L-argininal ethyl cyclol hydrochloride salt (prepared as described in Examples 12 through 15) by carbodiimide coupling to give 7.1.

The N$^g$-nitro group of 7.1 is then removed by hydrogenation with hydrogen gas and palladium on carbon in ethanol, water, and acetic acid to give 8.1. 8.1 is then reacted with 3 N HCl to provide 9.1.

Figure 8:
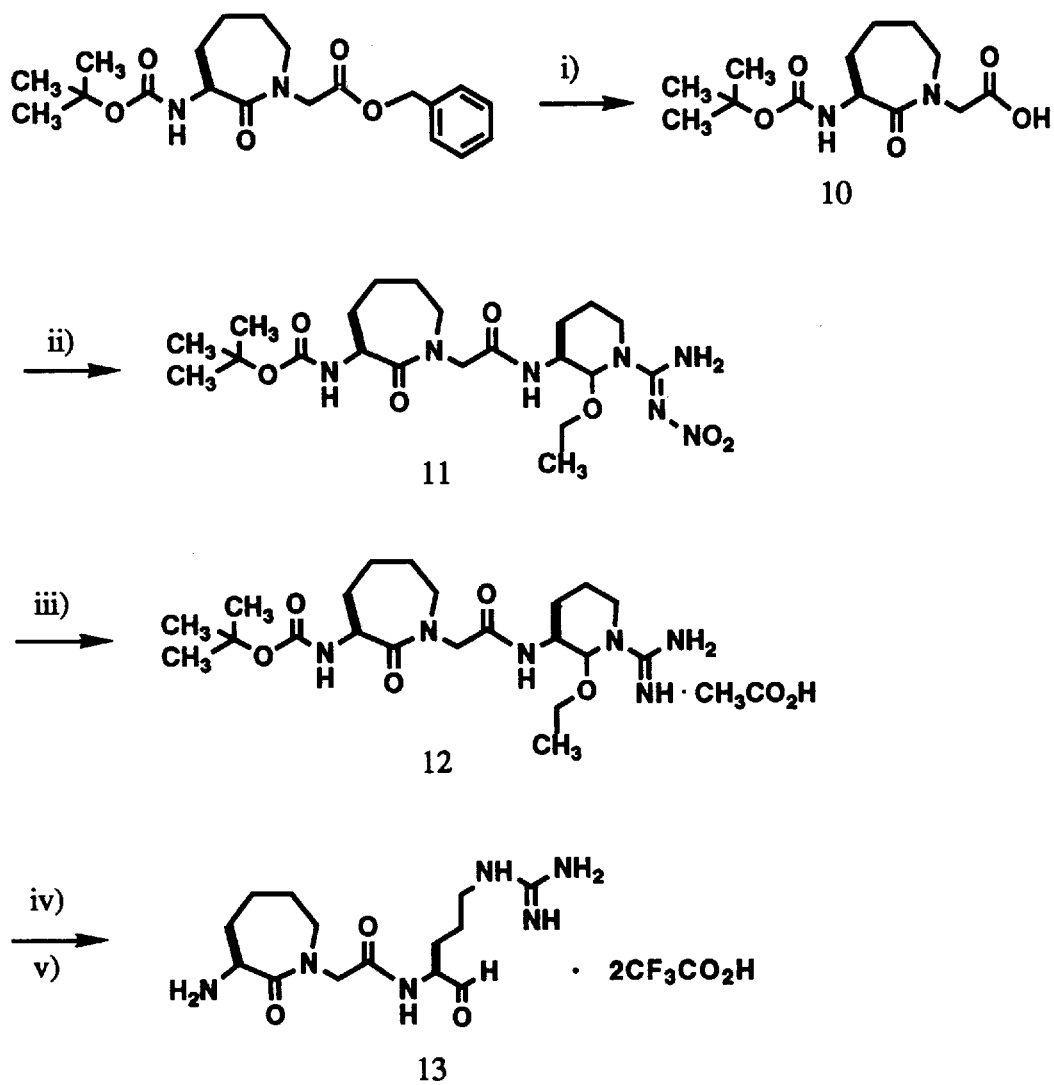
FIG. 8 depicts a preferred reaction scheme for the preparation of certain compounds of the present invention. In this figure, i)-v) are defined as: i) hydrogen gas and palladium on carbon; ii) N$^g$-nitro-L-argininal ethyl cyclol hydrochloride salt, 1-hydroxybenzotriazole monohydrate, 1-ethyl-3-(3-dimethylaminopropyl)carbodiimide hydrochloride salt, and N,N-diisopropylamine; iii) hydrogen gas and palladium on carbon in ethanol, acetic acid and water; iv) 3N HCl; and v) HPLC purification with 0.1% trifluoroacetic acid in acetonitrile and water.
Figure 9:
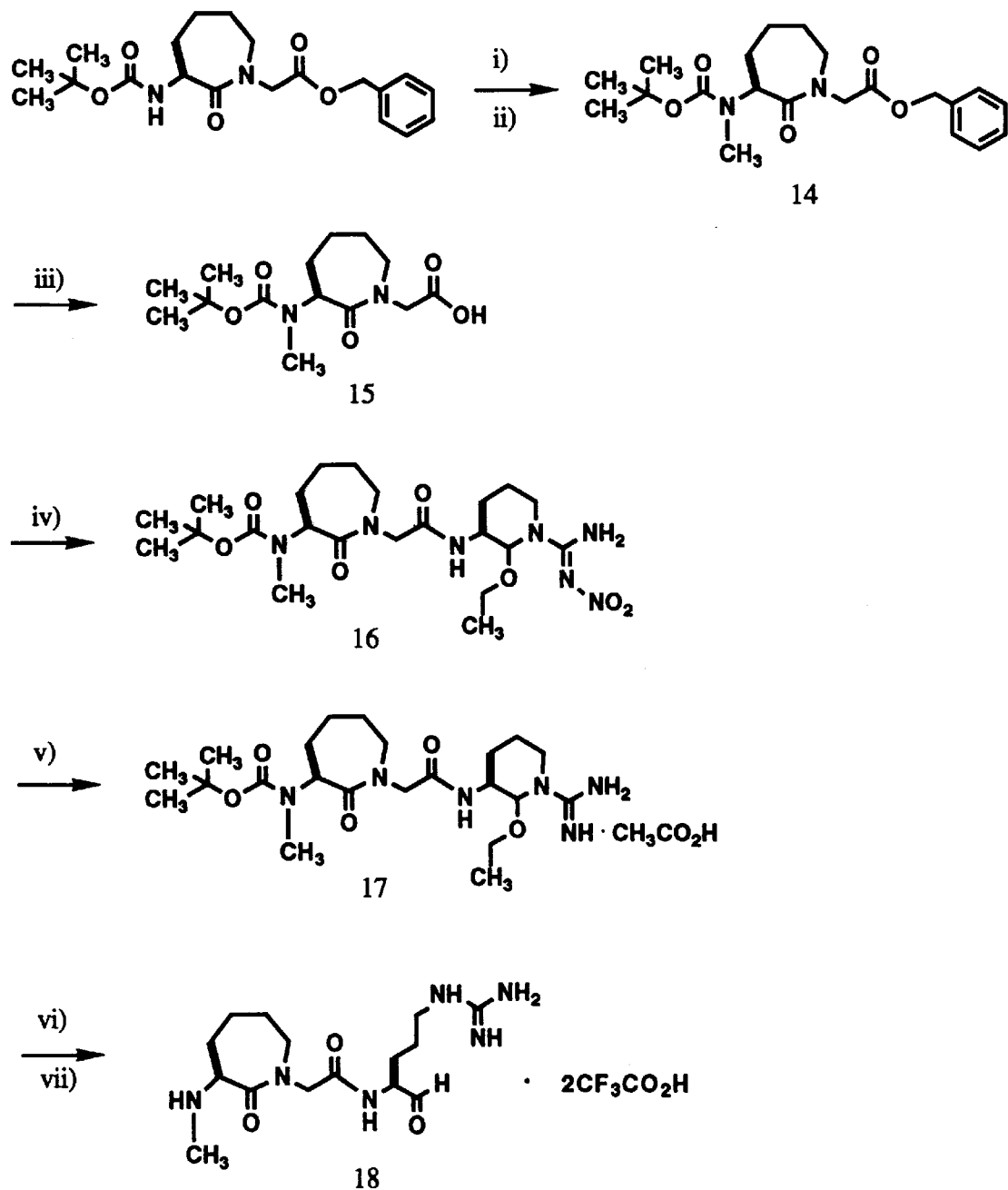
FIG. 9 depicts a preferred reaction scheme for the preparation of certain compounds of the present invention. In this figure, i)-vii) are defined as: i) sodium hydride; ii) methyl iodide; iii) hydrogen gas and palladium on carbon; iv) N$^g$-nitro-L-argininal ethyl cyclol hydrochloride salt, 1-hydroxybenzotriazole monohydrate, 1-ethyl-3-(3-dimethylaminopropyl)carbodiimide hydrochloride salt, and N,N-diisopropylamine; v) hydrogen gas and palladium on carbon in ethanol, acetic acid and water; vi) 3N HCl; and vii) HPLC purification with 0.1% trifluoroacetic acid in acetonitrile and water.

FIGS. 8 and 9 illustrate a preferred reaction scheme for the synthesis of compounds of the present invention in which X is a direct link such that $R^1$ is directly bonded to nitrogen in Formula II. As shown in FIG. 8, (S)-3-[(tert-butoxycarboxyl)amino]-2-oxo-hexahydro-1-azepine acetic acid, benzyl ester is deprotected to give the acid 10.1 by treatment with hydrogen gas and palladium on carbon in a Parr shaker at 40 psi. 10.1 is then coupled to N$^g$-nitro-L-argininal ethyl cyclol using 1-hydroxybenztriazole monohydrate, 1-ethyl-3-(3-dimethylaminopropyl) carbodiimide hydrochloride salt, and then N,N-diisopropylamine to give 11.1. The N$^g$-nitro group of 11 is removed by treatment with hydrogen gas and palladium on carbon in ethanol, water, and acetic acid at 50 psi. This reaction produces acetic acid salt 12.1. The ethyl cyclol group of 12.1 is hydrolyzed by treatment with 3N HCl, followed by HPLC purification with 30 0.1% trifluoroacetic acid in acetonitrile and water to produce 13.1. The scheme of FIG. 9 differs in that (S)-3-[(tert-butoxycarbonyl)amino]-2-oxo-hexahydro-1-azepine acetic acid, benzyl ester is first reacted with sodium hydride followed by methyl iodide to prepare the alkylated Boc protected amine 14.1. 14.1 is deprotected to form 15.1, which is treated to the same reactions as acid 10.1 in FIG. 8. The method used in FIG. 9 illustrates the reactions to make compounds in which X is a direct link to $R_1$, when $R_1$ is other than hydrogen.

Figure 10:
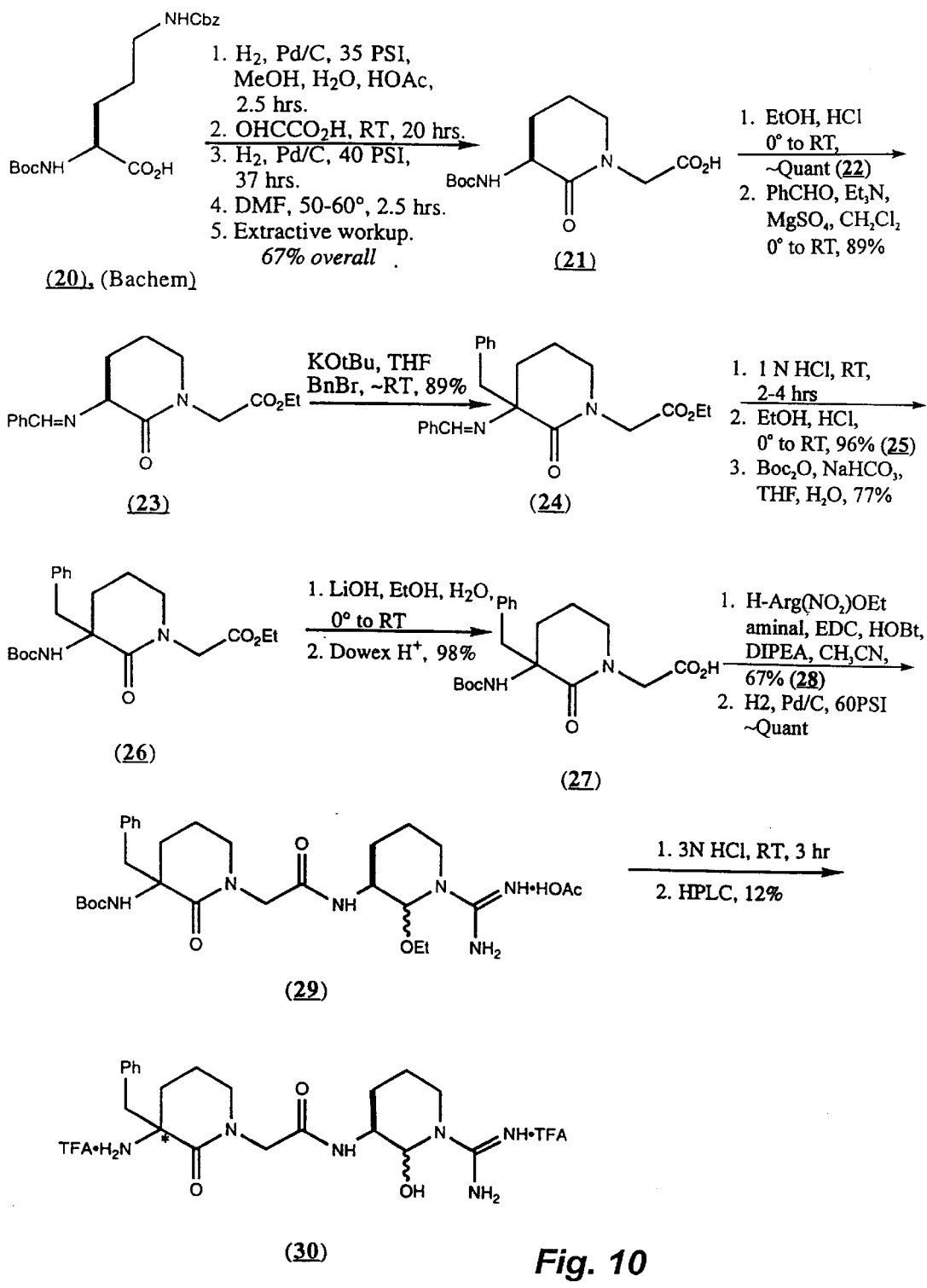
FIG. 10 depicts a preferred reaction scheme for preparation of compound 30, described in Examples 46 through 55. In this figure, the steps are defined as: synthesis of (21) from (20), 1. $H_2$, Pd/C, 35 PSI, MeOH, $H_2O$, HOAc, 2.5 hours; 2. $OHCCO_2H$, room temperature, 20 hours; 3. $H_2$, Pd/C, 40 PSi, 37 hours; 4. DMF, 50–60° C., 2.5 hours; 5. extractive workup, for a 67% overall yield. Synthesis of (23) from (21), 1. EtOH, HCl, 0° C. to room temperature, quantitative yield of (22); 2. PhCHO, $Et_3N$, $MgSO_4$, $CH_2Cl_2$, 0° C. to room temperature, 89% yield of (23). Synthesis of (24) from (23), KOtBu, THF, BnBr, at approximately room temperature, for 89% yield. Synthesis of (26) from (24), 1. 1 N HCL, room temperature for 2–4 hours,; 2. EtOH, HCl, 0° C. to room temperature, 96% yield of (25); 3. $Roc_2O$, $NaHCO_3$, THF, $H_2O$, 77% yield of (26). Synthesis of (27) from (26), 1. LiOH, EtOH, $H_2O$, 0° C. to room temperature; 2. Dowex $H_+$, 98% yield of (27). Synthesis of (29) from (27), 1. H-Arg($NO_2$)OEt aminal, EDC, HOBt, DIPEA, $CH_3CN$, 67% yield of (28); 2. $H_2$, Pd/C, 60PSI, quantitative yield of (29). Synthesis of (30) from (29), 1. 3N HCl, room temperature, 3 hours; 2. HPLC, 12% yield of (30).

FIG. 10 depicts the synthesis of a preferred species. Intermediate 20 is catalytically hydrogenated, condensed with glyoxylic acid, catalytically rehydrogenated and the resultant intermediate is thermally dehydrated in warm dimethylformamide to afford the lactam 21. Treatment of 21 with dry hydrogen chloride in ethanol simultaneously effects both deblocking of the Boc group as well as esterification of the carboxyl moiety and produces aminoester hydrochloride 22. Condensation of 22 with benzaldehyde in the presence of a base such as triethylamine employing a dehydrating agent such as magnesium sulfate affords the imine derivative 23. Deprotonation of intermediate 23 with a selective base such as potassium tert-butoxide, lithium N,N-diisopropylamide or lithium bis(trimethylsilyl)amide followed by reaction with benzyl bromide delivers the alkylated compound 24. Hydrolysis of 24 with dilute hydrochloric acid at ambient temperature for 2 to 4 hours and partial reesterification with anhydrous ethanol and dry hydrogen chloride gives 25. Reprotection of the free amino group of 25 with di-tert-butyl dicarbonate in the presence of saturated sodium bicarbonate in THF provides 26. Hydrolysis of 26 in an aqueous alcoholic solvent with a strong base like lithium, sodium or potassium hydroxide followed by protonation using a strongly acidic cation exchange resin such as Dowex(registered sign) 50WX8-400 affords the N-boc-protected lactam carboxylic acid intermediate 27. Standard peptide coupling of 27 and Ng-nitro-argininal ethyl cyclol using EDC, HOBt and N,N-diisopropylethylamine in an inert solvent such as acetonitrile at ambient temperature gives 28. Catalytic hydrogenation of 28 in ethanol, acetic acid and water using a palladium on charcoal catalyst affords the acetate salt precursor 29. Finally, hydrolysis with dilute hydrochloric acid at ambient temperature followed by HPLC purification produces the novel target 30.

Figure 11:
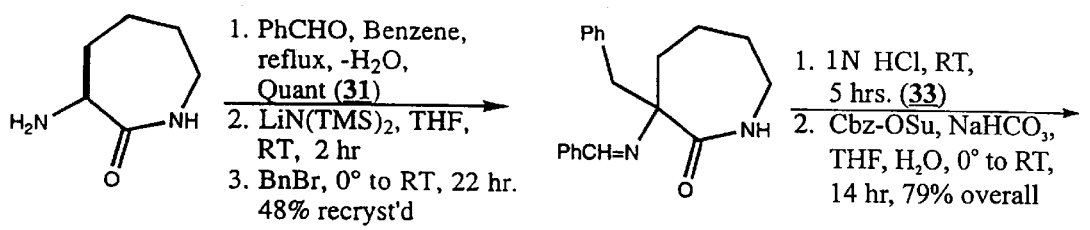
FIG. 11 depicts a preferred reaction scheme for preparation of compound 39, described in Examples 56 through 64. In this figure, the steps are defined as: synthesis of (32), 1. PhCHO, benzene, reflux, —$H_2O$, quantitative yield of (31); 2. $LiN(TMS)_2$, THF, room temperature, 2 hours; 3. BnBr, 0° C. to room temperature, 22 hours, 48 % recrystalized. Synthesis of (34) from (32), 1. 1N, HCl, room temperature, 5 hours to yield (33); 2. Cbz—OSu, $NaHCO_3$, THF, $H_2O$, 0° C. to room temperature, 14 hours, 79% overall yield. Synthesis of (35) from (34), 1. $LiN(TMS)_2$, THF, room temperature, 30 minutes; 2. $BrCH_2CO_2t$-Bu, room temperature, 20 hours; 3. $NH_4Cl$, $H_2O$, 60% yield of (35). Synthesis of (38) from (35), 1. TFA, $CH_2Cl_2$, 0° C. to room temperature, 80% yield; 2. HCl.Arg($NO_2$)OEt aminal, EDC, HOBT, DIPEA, room temperature, $CH_3CN$, 18 ours, 73% of (37); 3. H2, Pd/C, 55 PSI, EtOH, HOAc, $H_2O$, 99% yield of (38). Synthesis of (39) from (38), 1. 3N HCl, room temperature, 3 hours; 2. HPLC, 36% yield of (39).
Figure 11:
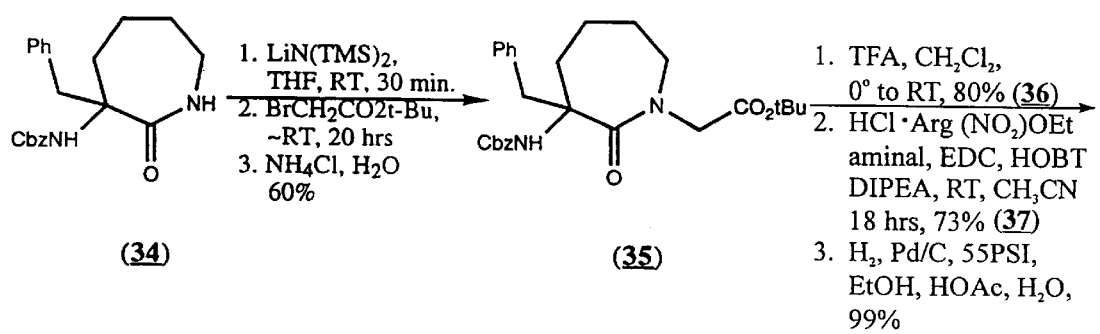
Figure 11:
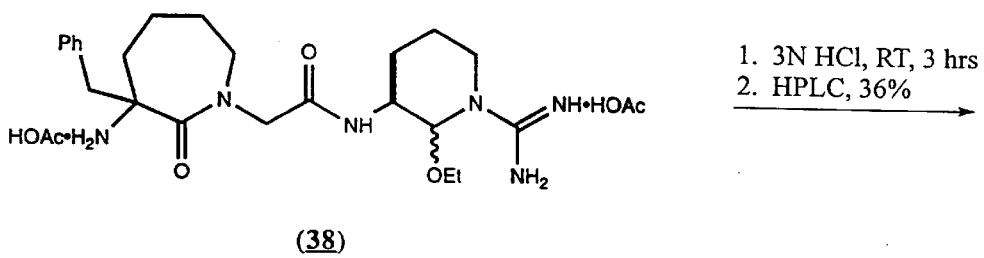
Figure 11:
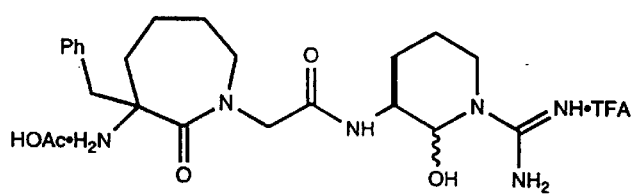

FIG. 11 depicts the synthesis of a preferred species which is the 7-membered ring homolog of target 30. α-Amino-ε-caprolactam is condensed with benzaldehyde in azeotropically refluxing benzene solution to afford imine 31. Deprotonation of 31 with a selective base such as potassium tert-butoxide, lithium N,N-diisopropylamide or lithium bis(trimethylsilyl)amide followed by reaction with benzyl bromide delivers the alkylated compound 32. Hydrolysis of 32 with dilute hydrochloric acid at ambient temperature affords the amine hydrochloride salt 33. Protection of the amino group by reaction of 33 with N-(benzyloxycarbonyloxy)-succinimide and sodium bicarbonate in aqueous THF provides N-Cbz-lactam intermediate 34. Selective deprotonation of 34 with a hindered base such as lithium bis-(trimethylsilyl)amide and addition of tert-butyl bromoacetate followed after 20 hours by quenching with ammonium chloride leads to product 35. Cleavage of the tert-butyl ester moiety of 35 is effected with trifluoroacetic acid in methylene chloride at about 0° to room temperature and affords the carboxylic acid derivative 36. Standard peptide coupling of 36 and $N^g$-nitro-argininal ethyl cyclol using EDC, HOBt and N,N-diisopropylethylamine in an inert solvent such as acetonitrile at ambient temperature gives 37. Catalytic hydrogenation of 37 in ethanol, acetic acid and water using a palladium on charcoal catalyst affords the acetate salt precursor 38. Finally, hydrolysis of 38 with dilute hydrochloric acid at ambient temperature followed by HPLC purification give the novel target 39.

Figure 12:
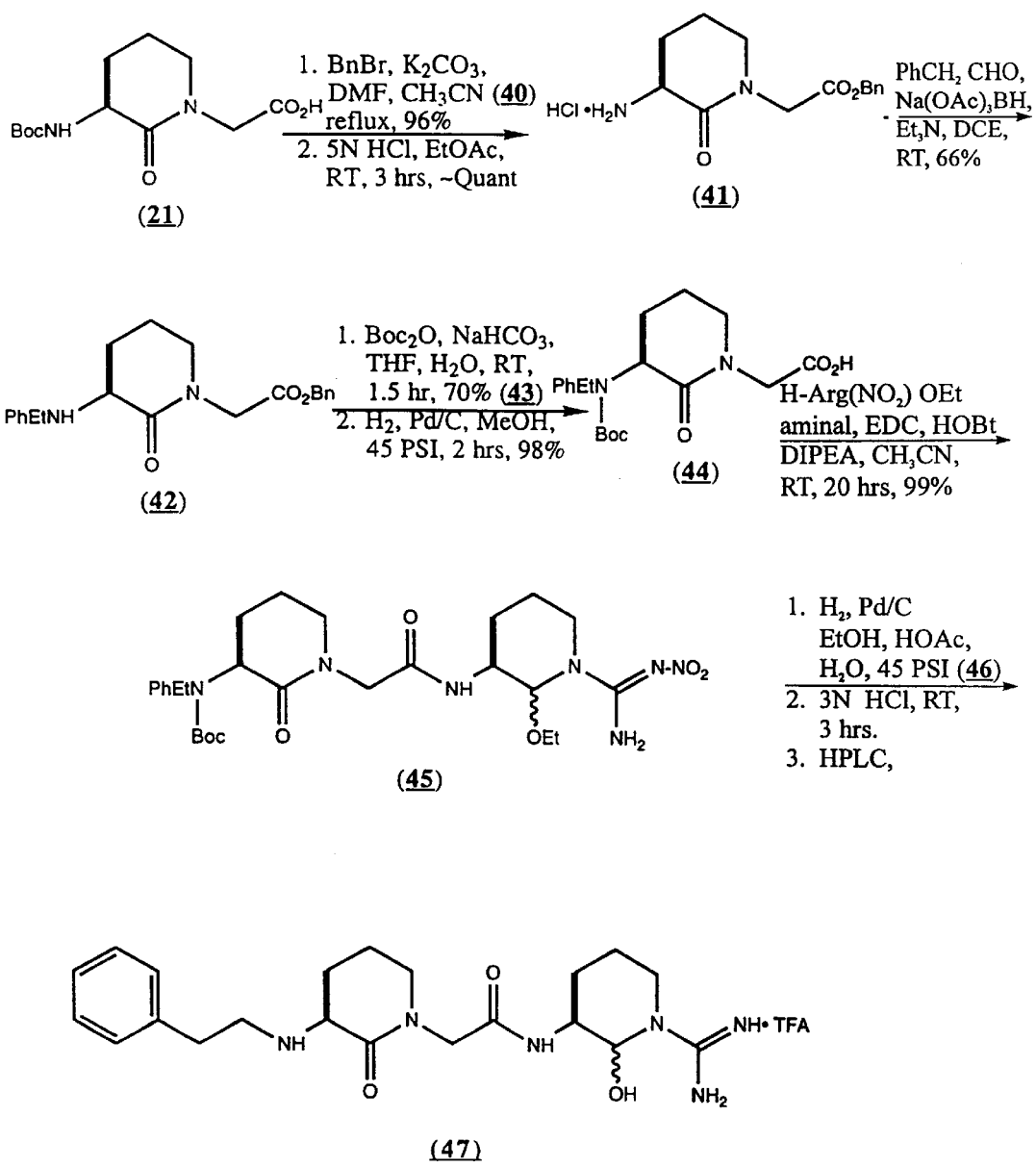
FIG. 12 depicts a preferred reaction scheme for preparation of compound 47, described in Examples 65 through 72. In this figure, the steps are defined as: synthesis of (41) from (21), 1. BnBr, $K_2CO_3$, DMF, $CH_3CN$, reflux, 96% yield; 2. 5N HCl, EtOAc, room temperature, 3 hours, quantitative yield of (41). Synthesis of (42) from (41), 1. $Boc_2O$, $NaHCO_3$, THF, $H_2O$, room temperature, 1.5 hours, 70% yield of (43); 2. $H_2$, Pd/C, MeOH, 45 PSi, 2 hours, 98% yield of (44). Synthesis of (45) from (44), H-Arg($NO_2$)OEt aminal, EDC, HOBt, DIPEA, $CH_3CN$, room temperature, 20 hours, 99% yield of (45). Synthesis of (47) from (45), 1. $H_2$, Pd/C, EtOH, HOAc, $H_2O$, 45 PSi to yield (46); 2. 3N, HCl, room temperature, 3 hours; 3. HPLC to yield (47).

The synthesis of an example of another structural class based on general formula I is shown in FIG. 12. Compound 21, prepared as described above, is esterified by treatment with anhydrous potassium carbonate and benzyl bromide in refluxing acetonitrile to give 40. The boc protecting group of 40 is selectively cleaved by treatment with anhydrous hydrogen chloride in ethyl acetate and provides the amine hydrochloride 41. Reductive amination of salt 41 with phenylacetaldehyde using sodium triacetoxyborohydride and triethylamine in an inert solvent such as 1,2-dichloroethane delivers the amine derivative 42. The amino group of 42 is protected by reaction with di-tert-butyl dicarbonate in the presence of saturated sodium bicarbonate in THF and provides 43. Catalytic hydrogenation of 43 using palladium on charcoal leads to the carboxylic acid 44. Standard peptide coupling of 44 and $N^g$-nitro-argininal ethyl cyclol using EDC, HOBt and N,N-diisopropylethylamine in an inert solvent such as acetonitrile at ambient temperature gives 45. Catalytic hydrogenation of 45 in ethanol, acetic acid and water using a palladium on charcoal catalyst affords the acetate salt precursor 46. Finally, hydrolysis of 46 with dilute hydrochloric acid at ambient temperature followed by HPLC purification gives the novel target 47.

Figure 13:
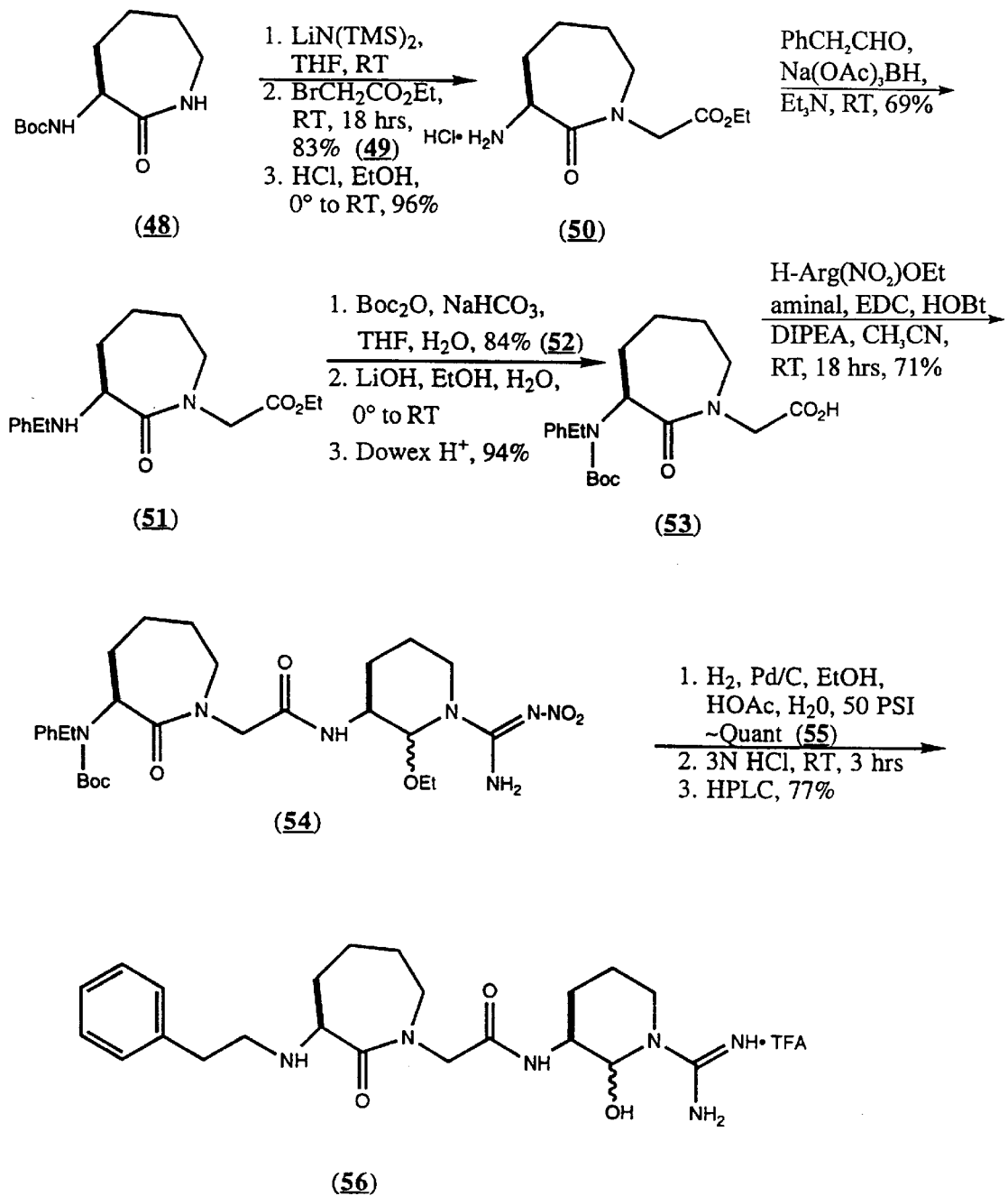
FIG. 13 depicts a preferred reaction scheme for preparation of compound 56, described in Examples 73 through 80. In this figure, the steps are defined as: synthesis of (50) from (48), 1. $LiN(TMS)_2$, THF, room temperature; 2. $BrCH_2CO_2Et$, room temperature, 18 hours, 83% yield of (49); 3. HCl, EtOH, 0° C. to room temperature, 96% yield of (50). Synthesis of (51) from (50), $PhCH_2CHO$, Na(OAc)$_3BH$, $Et_3N$, room temperature, 69% yield of (51). Synthesis of (53) from (51), 1. $Boc_2O$, $NaHCO_3$, THF, $H_2O$, 0° C. to room temperature; 3. Dowex $H^+$, 945 yield of (53). Synthesis of (54) from (53), H-Arg($NO_2$)OEt aminal, EDC, HOBt, DIPEA, $CH_3CN$, room temperature, 18 hours, 71% yield of (54). Synthesis of (56) from (54), 1. $H_2$, Pd/C, EtOH, HOAC, $H_2O$, 50PSI, quantitative yield of (55); 2. 3N HCl, room temperature, 3 hours; 3. HPLC, 77% yield of (56).

FIG. 13 depicts the synthesis of a preferred species which is the 7-membered ring homolog of target 47. Compound 48, prepared as described above (equivalent to compound 2 from FIG. 6), is treated with a hindered base such as lithium bis-(trimethylsilyl)amide and is alkylated with ethyl bromoacetate to afford 49. Cleavage of the boc group of 49 with hydrogen chloride in ethanol gives amine hydrochloride salt 50. Reductive amination of salt 50 with phenylacetaldehyde using sodium triacetoxyborohydride and triethylamine in an inert solvent such as 1,2-dichloroethane delivers the amine derivative 51. The amino group of 51 is protected by reaction with di-tert-butyl dicarbonate in the presence of saturated sodium bicarbonate in THF and provides 52. Hydrolysis of 52 in an aqueous alcoholic solvent with a strong base like lithium, sodium or potassium hydroxide followed by protonation using a strongly acidic cation exchange resin such as Dowex® 50WX8-400 affords the N-boc-protected lactam carboxylic acid intermediate 53. Standard peptide coupling of 53 and $N^g$-nitro-argininal ethyl cyclol using EDC, HOBt and N,N-diisopropylethylamine in an inert solvent such as acetonitrile at ambient temperature gives 54. Catalytic hydrogenation of 54 in ethanol, acetic acid and water using a palladium on charcoal catalyst affords the acetate salt precursor 55. Finally, hydrolysis of 55 with dilute hydrochloric acid at ambient temperature followed by HPLC purification give the novel target 56.

For compounds of the present invention containing alkenyl, heterocyclic, or aryl moieties substituted with halogen, cyano, nitro, or —S—$Z_1$, it is preferred to avoid the use of hydrogen gas with palladium on carbon. Instead, it is preferred to use boron tris(trifluoroacetate), $B(OCOCF_3)_3$, to cleave the $N^g$-nitro of the arginine group. The reagent is prepared by the reaction of $BBr_3$ and $CF_3COOH$ in dichloromethane at 0° C. The reagent is also commercially available. Generally, the $N^g$-nitro compound is treated with boron tris(trifluoroacetate) in trifluoroacetic acid at 0° C. Fieser, M. and Fieser, L. F., *Reagents for Organic Synthesis*, p. 46, John Wiley & Sons, New York (1974); Pless, J., and Bauer, W. *Anew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

An even more preferred method is to use the di-N-t-butoxycarbonyl protecting group for the L-argininal moiety for groups incompatible with hydrogenation with palladium on carbon. For example, alpha-N-benzyloxycarbonyl-omega, omega'-di-N-t-butoxycarbonylarginine is dissolved in acetonitrile and treated with hydroxybenzotriazole and 1-ethyl-3-(3-dimethylamino-propyl)carbodiimide HCl salt to form alpha-N-benzyloxycarbonyl-omega, omega'-di-N-t-butoxycarbonyl-L-arginine lactam. The lactam is reduced by treatment with $LiAlH_4$ in THF at −70° C. to provide alpha-N-benzyloxycarbonyl-omega, omega'-di-N-t-butoxycarbonyl-L-argininal. This aldehyde is protected as the diethyl acetal by treatment with ethanol and HCl. The N-benzyloxycarbonyl protecting group is removed by treatment with hydrogen gas and palladium on carbon to give omega, omega'-di-N-t-butoxycarbonyl-L-argininal diethyl acetal, HCl salt. This protected L-argininal moiety can then be coupled to a desired carboxylic acid by treatment with N-hydroxybenzotriazole and 1-ethyl-3-(3-dimethylamino-propyl)carbodiimide HCl salt. The diethyl acetal and the di-BOC protecting groups are removed by treatment with hexafluorophosphoric acid in acetonitrile at 0° C. The reaction is quenched with 2.5 M aqueous sodium acetate until pH 4 is reached. The mixture is filtered through a 2 micron filter. Preparative HPLC using 0.1% $CF_3COOH$ in 10–40% aqueous acetonitrile provides the trifluoroacetate salt of the desired substituted L-argininal compound.

3. Selection of Preferred Compounds

The compounds of the present invention are screened for their ability to inhibit thrombin, plasmin, recombinant tissue plasminogen activator (rt-PA), activated protein C (aPC), chymotrypsin, fXa and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and trypsin for a given compound is greater than or equal to its $IC_{50}$ (or $K_i$, respectively) for thrombin.

The compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. Ki is that concentration of test compound giving 50% inhibition of the rate of substrate turnover. Examples A and B provide an exemplar of the in vitro assays used to select the compounds of the present invention.

Certain of the preferred compounds of the present invention have a $K_i$ of about 0.001 to about 200 nm in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, rt-PA, aPC, chymotrypsin, and trypsin which is about 20 to about 100,000 times greater than its $IC_{50}$ for thrombin. More especially preferred compounds have an $IC_{50}$ for plasmin, rt-PA, aPC, chymotrypsin, and trypsin which is about 100 to about 1,000,000 times greater than its $IC_{50}$ for thrombin. In the event that a compound of the present invention has an $IC_{50}$ with respect to plasmin, rt-PA, aPC, chymotrypsin, or trypsin which is greater than the highest concentration of compound tested, the $IC_{50}$ is taken to be that highest concentration of compound.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Reminaton's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixers for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutcial compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of (S)-3-[(tert-butoxycarbonyl)amino]-2-oxo-1-piperidineacetic acid

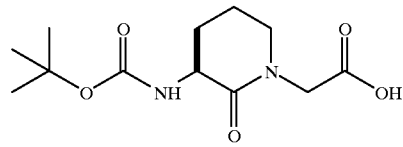

This compound was made in 4 steps by a modification of the literature procedure of D. F. Veber and R. M. Freidinger, U.S. Pat. No. 4,192,875 (Mar. 11, 1980); and R. M. Freidinger, et. al., J. Org. Chem.,47: 104–109 (1982). The new method disclosed below proceeds through cleaner intermediates and thus allows for the preparation of large quantitites of material in a high state of purity.

N-alpha-Boc-N-delta-benzyloxycarbonyl-L-ornithine (100.3 g, 0.27 mole) was dissolved in a solution of methanol (450 mL), water (320 mL) and acetic acid (46.5 mL). 10% alladium on carbon catalyst (10.0 g) was added and the mixture was hydrogenated on a Parr apparatus at 35 psi for 2.5 hours. Thin-layer chromatography (silica gel; 20:10:3 dichloromethane/methanol/acetic acid; ninhydrin) showed clean conversion to N-alpha-Boc-L-ornithine.

After purging with nitrogen, glyoxylic acid (27.72 g, 0.30 mole) was added, the mixture was stirred at ambient temperature for 50 hours, hydrogenated at 35 psi for 17 hours, and the catalyst was filtered off. A fresh portion of 10% palladium on carbon catalyst (5 g) was added and the mixture was hydrogenated for a further 20 hours on the Parr Shaker at 40 psi. The catalyst was removed by filtration and the filtrate was concentrated to dryness under vacuum. The residue was taken up in methanol and reevaporated. This process was repeated and the residue was pumped at <1 mm Hg overnight to afford a yellow foam.

The crude intermediate was dissolved in dry dimethylformamide (625 mL) and heated to 50–60° C. for 2.5 hours. The solvent was removed under vacuum at 80° C. The resultant oil was dissolved in 500 mL of dichloromethane and extracted with 500 mL of 1M sodium hydroxide solution. The aqueous solution was extracted with 500 mL of dichloromethane, acidified with cooling with 550 mL of 1M HCl, re-extracted with 5×500 mL dichloromethane and 2×500 mL 9:1 dichloromethane/isopropanol. The combined organic layers were dried over anhydrous magnesium sulfate and evaporated to afford 50 g (67% yield) of the title compound as a solidifying oil, judged pure (single spot with Rf=0.30) by thin-layer chromatography (silica gel; 27:3:1 dichloromethane/methanol/acetic acid).

Example 2

Preparation of (S)-N-alpha-Boc-$N^g$-nitroargininol

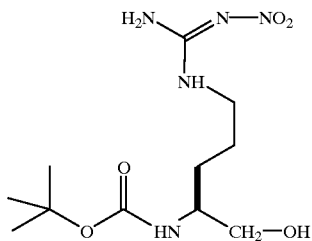

To a suspension of (S)-N-alpha-Boc-$N^g$-nitro-arginine (370 g, 1.15 moles) in 6 liters of dry tetrahydrofuran at −78° C., borane.tetrahydrofuran complex 1.0 M (2.6 liters) was slowly added. The reaction temperature was controlled so that it did not exceed −60° C. After the addition was complete, the reaction was placed in a freezer at −20° C. overnight.

The following day, the greenish-yellow reaction mixture was cooled to −78° C. and slowly quenched with 3 liters of anhydrous methanol. Two hours after this quenching, the mixture was warmed to 25° C. and stirred for an additional 2 hours. The solvent is removed under vacuum to yield the title compound (360 g). Thin-layer chromatography gave an Rf=0.28 (silica, 90:10 dichloromethane/methanol).

Example 3

Preparation of (S)-$N^g$-nitroargininol hydrochloride

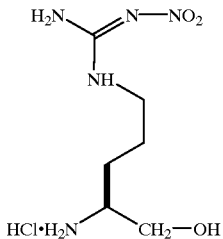

To a solution of the compound of Example 2 (34 g, 0.1117 mole) in 500 mL of methanol at 0° C., 1.2 liters of saturated HCl/methanol solution was added. After 30 minutes, the ice bath was removed and the reaction mixture was allowed to stir for 2 hours. After this time, the solvent was removed under vacuum and the resulting solid was used without further purification.

Example 4

Preparation of Boc-norVal(cyclo)-Gly-$N^g$-nitro-L-argininol

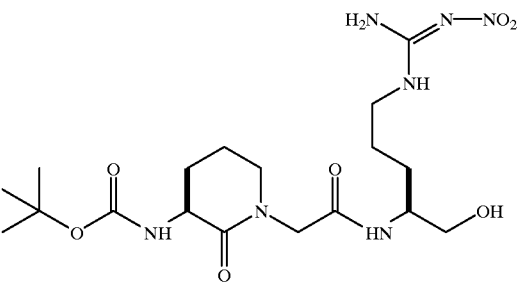

To a solution of the compound of Example 1 (7.49 g, 0.0275 mole) and HOBt (4.43 g, 0.0289 mole) in 75 mL of dry acetonitrile was added 4-methylmorpholine (8.35 g, 0.0825 mole, 9.06 mL) and the mixture was cooled to 0° C. A solution of the compound of Example 3 (7.55 g, 0.0275 mole) in 25 mL dry dimethylformamide was treated with 4-methylmorpholine (5.56 g, 0.055 mole, 6.05 mL), stirred for 5 minutes, and added to the above solution. To this mixture at 0° C. was added EDC (5.26 g, 0.0275 mole) portion-wise over 2 minutes. The reaction was stirred from 0° C. to ambient temperature over 17 hours, and the solvents were removed under vacuum. The residue was pre-purified by filtration through a short silica gel flash column using a gradient of ranging from 5–20% methanol-dichloromethane to afford a yellow foam. Recrystallization from ethyl acetate/methanol afforded 7.70 g (61% yield) of the title compound as a colorless solid, with mp=160–162° C. Thin-layer chromatography gave an Rf=0.45 (silica gel; 4:1 dichloromethane/methanol).

Example 5

Preparation of norVal(cyclo)-Gly-$N^g$-nitro-L-argininol hydrochloride salt

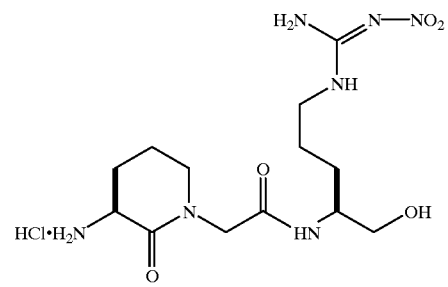

To a suspension of the compound of Example 4 (3.86 g, 8.40 mmole) in 100 mL of ethyl acetate at 0° C. under $N_2$ was added 1N HCl/ethyl acetate solution (42 mL, 5 equivalents). The resultant pasty suspension was stirred at 0° C. for 45 minutes and allowed to stir at ambient temperature overnight. The product was collected by suction filtration under a $N_2$ atmosphere, dissolved in dry methanol and evaporated to dryness under vacuum. This process was repeated and after vacuum drying afforded 3.38 g (100% crude yield) of the title compound as an amorphous, hygroscopic solid which was judged about 95% pure by NMR and thin-layer chromatography and was utilized immediately in

Example 6

Preparation of N-benzylsulfonyl-norVal(cyclo)-Gly-N^g-nitro-L-argininol

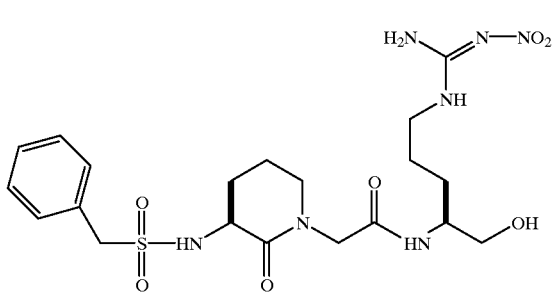

To a solution of the compound of Example 5 (395.8 mg, 1.0 mmole) in 10 mL dry dimethylformamide was added anhydrous potassium carbonate powder (276.4 mg, 2.0 mmole). After stirring at ambient temperature for 30 minutes, benzylsulfonyl chloride (190.7 mg, 1.0 mmole) was added. After 24 hours, the mixture was diluted with dichloromethane, the solids were filtered off, and the solvent was removed under vacuum to give a residue. The residue was purified by flash chromatography on silica gel, eluting with a gradient ranging from 10–20% methanol-dichloromethane to afford 220 mg (43% yield) of the title compound as a colorless foam. Thin-layer chromatography gave an Rf=0.5 (silica gel; 4:1 dichloromethane/methanol).

Example 7

Preparation of N-benzylsulfonyl-norVal(cyclo)-Gly-L-argininol, acetate salt

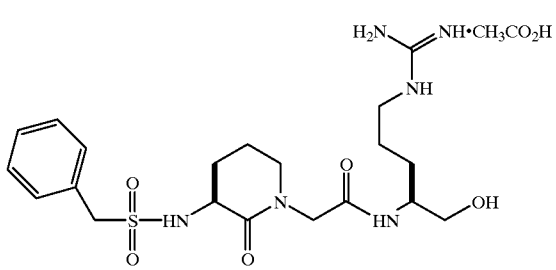

To a solution of the compound of Example 6 (965.3 mg, 1.88 mole) in 125 mL methanol was added acetic acid (903.2 mg, 15.0 mmole, 0.86 mL) followed by 10% palladium on carbon catalyst (386 mg). The mixture was hydrogenated on the Parr shaker at 35 psi for 17 hours, filtered and solvents were removed under vacuum. The residue was pumped at <1 mm Hg with occasional gentle heating over a 2 day period and afforded 1.02 g (100% crude yield) of the title compound as a foam. Thin-layer chromatography gave an Rf=0.32 (silica gel; 20:10:2 dichloromethane/methanol/concentrated ammonium hydroxide). Fast atom bombardment mass spectrometry confirmed the theoretical molecular weight of 468.

Example 8

Preparation of N-benzylsulfonyl-norVal(cyclo)-Gly-L-argininal, trifluoroacetate salt

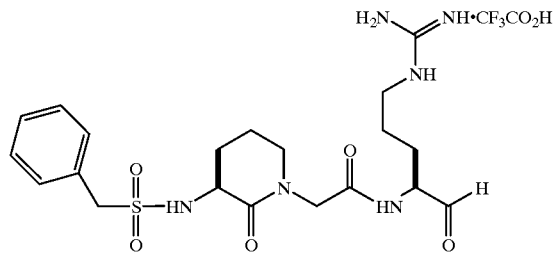

To a solution of compound of Example 7 (218.0 mg, 0.412 mmole) in 3 mL of dry dimethylsulfoxide and 3 mL of dry toluene at about 5° C. was added dichloroacetic acid (265.9 mg, 2.06 mmole, 170.1 mL) followed after 1 minute by EDC (790.6 mg, 4.12 mmole). The mixture was stirred at 5° C. for 5 minutes and then allowed to stir at ambient temperature for 90 minutes. The reaction was quenched by the addition of 35 ML water, extracted with 3×25 mL diethyl ether, and diluted with water to give a total volume of 50 mL. The aqueous solution was briefly placed on the rotary evaporator to remove any volatiles. The mixture was purified by reverse-phase HPLC using a standard C18 50×300 mm cartridge employing a 10–30% gradient system of acetonitrile-water (containing 0.1% trifluoroacetic acid) over 1 hour. Pooled fractions of interest were lyophilized and afforded 151 mg (63% yield) of the title compound as a colorless, amorphous solid. HPLC (on C18 reverse phase) analysis revealed 3 product forms. Fast atom bombardment mass spectrometry confirmed the theoretical molecular weight of 466.

Example 9

Preparation of norVal(cyclo)-Gly-O-methyl ester, hydrochloride salt

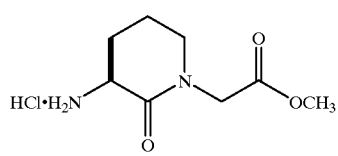

The compound of Example 1 (43.5 g, 0.160 mole) was dissolved in 150 mL of absolute methanol, cooled to 0° C., and treated dropwise with saturated HCl in methanol (400 mL). The solution was stirred at 0° C. for 1 hour and then warmed to ambient temperature and stirred for 14 hours. The solution was concentrated under vacuum to afford the title compound as a clear oil which was used directly in the next example. Thin-layer chromatography gave an Rf=0.25 (silica gel; 27:3:1 dichloromethane/methanol/concentrated ammonium hydroxide).

Example 10

Preparation of N-benzylsulfonyl-norVal(cyclo)-Gly-O-methyl ester

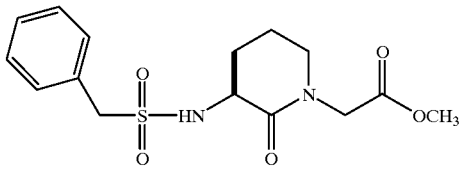

The compound of Example 8 (19.1 g, 85.8 mmole) was slurried in 850 mL of dry acetonitrile and was treated with benzylsulfonyl chloride (32.7 g, 0.172 mole). The solution was cooled to 0° C. and treated dropwise with triethylamine (60.0 mL, 0.428 mole). After 2 hours, an additional portion of benzylsulfonyl chloride (16.4 g, 85.8 mmole) was added. The solution gradually warmed to ambient temperature and was stirred for 16 hours. The solids were filtered and the filtrate was concentrated under vacuum to give an oil. The oil was purified by flash column chromatography (silica gel; eluting with a gradient of 10–50% diethyl ether in dichloromethane) to give 19.8 g (68% yield) of the title compound as a white foam. Thin-layer chromatography gave an Rf=0.55 (silica gel; 27:3:1 dichloromethane/methanol/acetic acid).

Example 11

Preparation of N-benzylsulfonyl-norVal(cyclo)-Gly

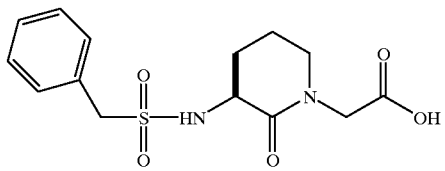

The compound of Example 9 (17.2 g, 52.7 mmole) was dissolved in 350 mL of methanol, cooled to 0° C., and treated with 1.0M lithium hydroxide in water (116 mL) dropwise. After 1 hour, the reaction mixture was allowed to warm to ambient temperature and was stirred for 18 hours. Dowex 50X8-400 ion-exchange resin (H$^+$ form, 49 g) was added to the slurry to adjust the pH to 3. After stirring for 30 minutes, the slurry was filtered and the resin was washed with several portions of water/methanol. The filtrate was concentrated under vacuum. The resulting residue was taken up in acetonitrile and concentrated under vacuum. This was repeated one more time to give 17.2 g (100% yield) of the title compound as a colorless, amorphous solid. Thin-layer chromatography gave an Rf=0.30 (silica gel; 27:3:1 dichloromethane/methanol/acetic acid).

Example 12

Preparation of N-alpha-t-butoxycarbonyl-N$^g$-nitro-L-arginine lactam

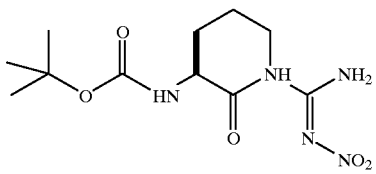

Alpha-N-t-butoxycarbonyl-N$^g$-nitroarginine (2.00 g, 6.3 mmole) was dissolved in tetrahydrofuran (100 mL) by heating the solution to 50° C. The solution was allowed to cool to room temperature. N-methyl piperidine (0.84 mL, 6.9 mmole) was added, and the solution was cooled in an ice bath. Isobutylchloroformate (0.83 mL, 6.3 mmole) was added, and the reaction mixture was stirred at 0° C. for 6 hours. The reaction mixture was stirred for 18 hours while the ice in the dewar was allowed to melt overnight. The solvent was removed under vacuum. The crude product was dissolved in 20% ethyl acetate/dichloromethane (10 mL), and was purified by flash chromatography through a 3×5 cm column of silica gel using 20% ethyl acetate/dichloromethane as eluent. 125 mL of eluent was collected. The solvent was removed under vacuum to afford 1.39 g (74% crude yield) of the title compound as white foam. R$_f$=0.44 (silica gel; 5% isopropanol in dichloromethane). Isobutanol was present as an impurity. This compound may be further purified by recrystallization from dichloromethane/hexanes or ethanol/water.

Example 13

Preparation of N-alpha-t-butoxycarbonyl-N$^g$-nitro-L-argininal

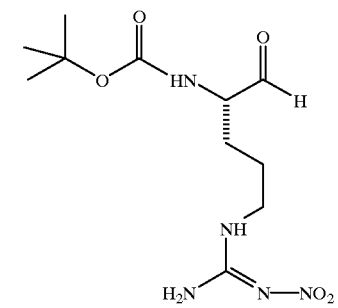

(a) Procedure 1

To a stirred solution of LiAlH$_4$ in tetrahydrofuran (3.8 mL of a 1.0M solution, 3.8 mmole), cooled in an ice bath, was added dropwise ethyl acetate (0.43 mL, 3.8 mmole) in tetrahydrofuran (5 mL). The solution was stirred for 30 minutes at 0° C. to preform LiAlH$_2$(OEt)$_2$.

The solution of this LiAlH$_2$(OEt)$_2$ was added dropwise to a stirred solution of compound of Example 12 (0.92 g, 3.1 mmole) in tetrahydrofuran (5 mL). After 30 minutes, the reaction is quenched with 1.0N HCl/tetrahydrofuran (2 mL of a 1:1 mixture). 1.0N HCl (20 mL) was added, and the solution was extracted three times with ethyl acetate (20 mL each). The combined organic layers were washed with water (5 mL), saturated sodium bicarbonate (5 mL) and twice with brine(5 mL each), dried over anhydrous magnesium sulfate, filtered and the solvent was removed under vacuum to give 0.94 g (100% yield) of the title compound as an off-white solid.

(b) Procedure 2

Alternatively, the title compound was made by the procedures which follows.

A 12 liter four-necked round bottom flask equipped with an overhead stirring apparatus was flame dried under a strong stream of nitrogen. After the flask had cooled, 120.0 g of alpha-N-t-butoxycarbonyl-N$^g$-nitro-L-arginine (376 mmole, 1 equivalent) was added under a blanket of nitrogen followed by the addition of 6 liters of anhydrous tetrahydrofuran (Aldrich sure-seal) via canula. The flask was then fitted with a thermometer and the resulting suspension was warmed to 50° C. with a heat gun while stirring. The reaction mixture was cooled to 5° C. with an ice bath and further cooled to −5° C. with an ice/acetone bath.

During the time it took for this solution to reach −5° C., 36.66 g of N-methyl-O-methylhydroxyamine hydrochloride (376 mmole, 1.0 equivalent) was weighed out in a 500 mL flask and suspended in 300 mL of dichloromethane. This suspension was sparged with nitrogen for 5 minutes, cooled to 0° C. and 46 mL of N-methylpiperidine (1.0 equivalent) was added via syringe under nitrogen. The mixture was sonicated briefly to insure complete dissolution/free base formation and recooled to 0° C. in an ice bath while still under nitrogen. The resulting solution of free base was used later.

When the above arginine solution had reached −5° C., 45 mL of N-methylpiperidine was added via syringe followed 5 minutes later by the addition of 46 mL of isobutyl chloroformate (0.95 equivalent) via syringe. The resulting solution was stirred for 15 minutes at −5° C. After this time, the free base solution of N-methyl-O-methyl hydroxylamine generated above was added via canula over about 15 minutes. Stirring was continued at −5° C. for another 1.5 hours at which time thin-layerchromatography (silica gel; 1:10:90 acetic acid/methanol/dichloromethane) indicated that the reaction was complete. The reaction mixture was filtered while still cold, the salts washed with 400 mL of cold tetrahydrofuran and the filtrate concentrated under vacuum on a rotary evaporator to yield a yellow foam.

The crude intermediate was taken up in 300 mL of dichloromethane and applied to a column of silica gel (70–230 mesh, 7×50 cm). The column was first eluted with 2 liters of dichloromethane followed by 2 liters of 2% methanol in dichloromethane. This was followed by elution with 5% methanol in dichloromethane until all of the product had been eluted (the eluant was checked for UV activity and five one-liter fractions were collected once this UV activity was apparent). Fractions containing pure product were pooled and concentrated under vacuum and pumped on overnight to yield 120.1 g (88% yield) of alpha-N-t-butoxycarbonyl-N$^g$-nitroarginine-N-methyl, N-methoxycarboxamide as light yellow foam. This foam was taken up in 300 mL of dichloromethane, 300 mL of toluene, and the volatiles were once again removed under vacuum to remove any residual water or methanol.

120.1 g of N-alpha-t-butoxycarbonyl-N$^g$-nitro-L-arginine-N-methyl, N-methoxycarboxamide (331.4 mmole) was taken up in 2.8 liters of dry (Aldrich sure-seal) tetrahydrofuran and transfered to a dry 5 liter 4-necked round bottom flask equipped with a mechanical stirrer and a low temperature thermometer. The solution was cooled to −70° C. with a dry ice/acetone bath and 300 mL of 1M LiAlH$_4$ in tetrahydrofuran was added by canula transfer directly from 100 mL Aldrich sure-seal bottles. An additional 50 mL of 1M LiAlH$_4$ in tetrahydrofuran was added via syringe (total 331 mL). During the additions, the reaction temperature was kept below −60° C. The reaction was stirred for 0.5 hours at −70° C., the cooling bath removed, and the reaction was slowly allowed to warm to 0° C. (about 2.5 hours). Between −30° C. and −20° C. a thick slurry resulted. When the reaction mixture obtained 0° C., a small aliquot was removed and partitioned between ethyl acetate/2M potassium bisulfate. The organic layer analyzed by thin-layerchromatography (silica gel; ethyl acetate).

When the reaction was judged to be complete, it was cooled to −70° C. and 503 mL of 2M potassium bisulfate was added via dropping funnel at a slow enough rate to keep the reaction temperature below −30° C. The cooling bath was removed and the reaction mixture was allowed to come to 0° C. over the course of 2 hours at which time a white precipitate was filtered off. The solids were washed with 500 mL of cold tetrahydrofuran. The filtrate was concentrated under vacuum on a rotary evaporator until most of the tetrahydrofuran was removed and the remaining white sludge was mostly aqueous. The crude product was taken up in 1.5 liters of ethyl acetate and washed with 0.2 M HCl (2×200 mL). The HCl extracts were back-extracted with 400 mL of ethyl acetate and the organics were combined and extracted with saturated sodium bicarbonate (2×200 mL). The bicarbonate extracts were also back-extracted with 400 ml of ethyl acetate. The organics were then combined and washed with brine (200 mL) followed by drying over anhydrous sodium sulfate. The solution was filtered, concentrated under vacuum on a rotary evaporator and pumped on overnight to yield a white solid (89.0 g) of crude title compound. This was chromatographed on silica gel and eluted with a gradient of 0 to 10% methanol in dichloromethane. The pure fractions were combined and evaporated to yield the title compound as a white solid (75 g, 74%).

Example 14

Preparation of N-alpha-t-butoxycarbonyl-N$^g$-nitro-L-argininal ethyl cyclol

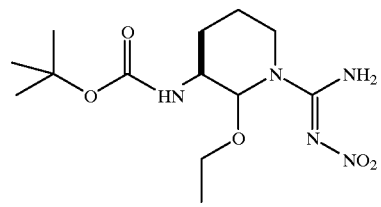

The compound of Example 13 (41.60 g, 0.137 mole) was dissolved in ethanol (200 mL) and concentrated HCl (1 mL) was added. After the reaction was complete by thin-layer chromatography (silica gel; 10% methanol in dichloromethane), the solvent was removed under vacuum. The crude product was purified by flash chromatography through a column of silica gel (230–400 mesh) using 0–10% ethyl acetate/dichloromethane as eluent. The combined fractions yielded 36.88 g (81%) of the title compound as pale yellow foam. Thin-layer chromatography gave an Rf=0.62 (silica gel; 5% methanol in dichloromethane).

Example 15

Preparation of N$^g$-nitro-L-argininal ethyl cyclol, hydrochloride salt

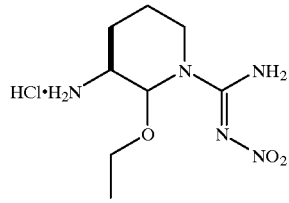

To a solution of the compound of Example 14 (35 g) in 500 mL of absolute ethanol at 0° C. was added slowly 500 mL of absolute ethanol saturated with HCl (g). This mixture was allowed to warm to 25° C. and checked by thin-layer chromatography. The appearance of a very polar product was the desired compound. Most of the HCl was removed with a stream of dry nitrogen and the resulting organic solvent was removed under vacuum. The resulting 33 g of the title compound as a yellow-white solid was used without further purification.

Example 16

Preparation of N-benzylsulfonyl-norVal(cyclo)-Gly-N$^g$-nitro-L-argininal ethyl cyclol

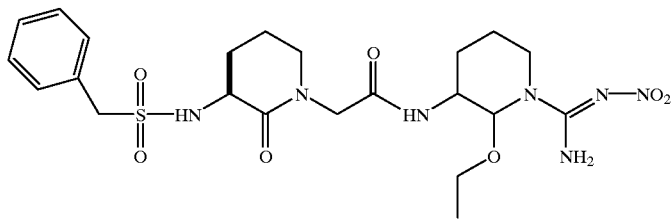

The compound of Example 11 (17.2 g, 52.7 mmole) was dissolved in 215 mL of acetonitrile and was treated with the compound of Example 15 (14.2 g, 53.0 mmole), EDC (15.2 g, 79.1 mmole), and HOBt (7.12 g, 52.7 mmole). The solution was stirred for 15 minutes at ambient temperature, cooled to 0°, and was then treated with N,N-diisopropylethylamine (45.9 mL, 0.264 mole). The reaction was warmed to ambient temperature and was stirred for 48 hours. The solution was concentrated under vacuum and the residue dissolved in 1.5 L ethyl acetate and washed with 2×150 mL each of 1N HCl, saturated sodium bicarbonate, and Brine. The organic layer was dried over anhydrous magnesium sulfate, filtered, and concentrated under vacuum to give a yellow foam. The foam was purified by flash column chromatography (silica gel; eluting with a gradient ranging from 3–5% ethanol in dichloromethane) to yield 11.5 g (40% yield) of the title compound as a white solid. Thin-layer chromatography gave an Rf=0.40 (silica gel; 9:1 dichloromethane/methanol).

Example 17

Preparation of N-benzylsulfonyl-norVal(cyclo)-Gly-L-argininal ethyl cyclol, acetate salt

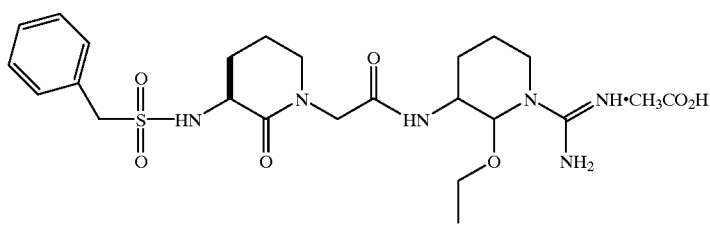

The compound of Example 16 (9.50 g, 17.6 mmole) was dissolved in ethanol (133 mL), water (33 mL), and acetic acid (33 mL). 10% palladium on carbon catalyst (4.0 g) was added and the solution was shaken on a Parr apparatus under 50 psi H$_2$ for 19 hours. The solids were filtered off and the filtrate was concentrated under vacuum to give a light brown oil of the title compound which was used directly in the following reaction. Thin-layer chromatography gave an Rf=0.35 (silica gel; 20:5:2 dichloromethane/methanol/concentrated ammonium hydroxide).

Example 18

Preparation of N-benzylsulfonyl-norVal(cyclo)-Gly-L-argininal, trifluoroacetate salt

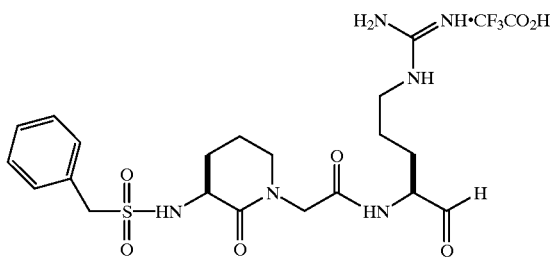

The compound of Example 17 (4.5 g, 8.1 mmole) was dissolved in 1N HCl (150 mL) and stirred at ambient temperature for 15 hours. 12N HCl (25.5 mL) was added to the solution and the reaction continued another 3.5 hours. Purification by reverse phase HPLC on a 50×300 mm C18 column using a gradient ranging from 10–30% of acetonitrile-water (containing 0.1% trifluoroacetic acid) over 1 hour yielded 3.8 g (81 % yield) of the title compound as a white solid. HPLC (on C18 reverse phase) analysis showed three peaks for the product. Fast atom bombardment mass spectrometry confirmed the theoretical molecular weight of 466.

Example 19

Preparation of N-Boc-L-methionyl-glycine methyl ester

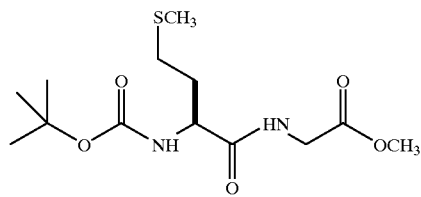

N-Alpha-Boc-methionine (24.9 g, 0.1 mole) and glycine methyl ester hydrochloride (12.6 g, 0.1 mole) were mixed in degassed dimethylformamide (150 mL). Triethylamine (13.9 mL, 0.1 mole) and HOBt (15.3 g, 0.1 mole) were dissolved in the mixture, and DCC (20.6 g, 0.1 mole) was added. The mixture was stirred at room temperature overnight and filtered. The filtrate was concentrated under vacuum, and the residue was redissolved in dichloromethane (150 mL). This solution was washed with 0.5M citric acid (3×50 mL) and 2N aqueous sodium bicarbonate (3×50 mL) and dried over anhydrous sodium sulfate. The solution was filtered, concentrated under vacuum, and recrystallized ethyl acetate/hexanes to give 24.1 g (75% yield) of the title product.

Example 20

Preparation of N-Boc-L-methionyl-glycine methyl ester methylsulfonium iodide

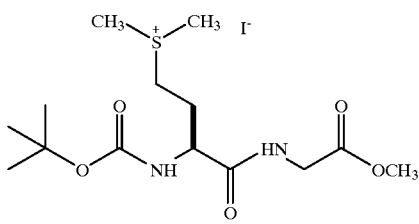

The compound of Example 19 (960 mg, 3 mmole) was dissolved with stirring in 6 mL of methyl iodide at room temperature. The reaction mixture was stirred for 6.5 hours over which time a gummy solid had separated. The supernatant was drawn off and the residue was dried under vacuum to give 1.41 g (100%) of the title compound as a hygroscopic foam.

Example 21

Preparation of (S)-3-Boc-amino-2-oxo-1-pyrrolidineacetic acid

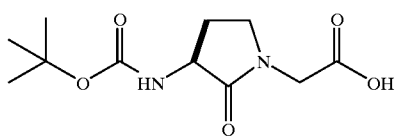

The compound of Example 20 (7.3 g, 15.6 mmole) was dissolved in 312 mL of 1:1 dimethylformamide/dichloromethane under nitrogen and cooled to 0° C. Sodium hydride (1.5 g of a 50% mineral oil suspension, 31.5 mmole) was added all at once, and the mixture was stirred at 0° C. for 2.5 hours. Ethyl acetate (104 mL) followed by water (24 mL) was added, and the resultant solution was left overnight at room temperature. The solution was concentrated under vacuum to a small volume and partitioned between water (50 mL) and dichloromethane (50 mL). The phases were separated, and the aqueous phase at pH 8 was acidified to pH 4 with 0.5M citric acid. Continuous extraction with dichloromethane, followed by concentration under vacuum, gave 2.06 g (51%) of the title compound as a crystalline solid.

Example 22

Preparation of (S)-3-Boc-amino-2-oxo-1-pyrrolidineacetic acid-N^g-L-nitroargininol

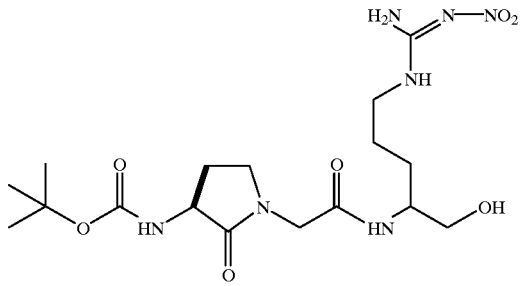

The compound of Example 21 (5.16 g, 0.02 mole), the compound of Example 3 (5.83 g, 0.022 mole), HBTU (8.34 g, 0.022 mole), HOBt (2.97, 0.02 mole) was dissolved in 500 mL of acetonitrile. To this solution was added N-methylmorpholine (10 mL, 0.09 mole) slowly. The reaction was stirred for 12 hours at 25° C. and. The solvent was removed under vacuum to yield a residue. The residue was dissolved in 500 mL of ethyl acetate and washed with water (100 mL), 10% HCL (3×100 mL), saturated sodium bicarbonate (3×100 mL) and Brine (100 mL). The organic phase was dried over anhydrous magnesium sulfate, filtered and the solvent evaporated under vacuum to yield a residue. The residue was chromatographed on silica gel (300 g), eluting with a gradient ranging from 2–10% methanol in dichloromethane to give 3.3 g (37%) of the title compound. Thin-layer chromatography gave an Rf=0.66 (silica gel; 95:5 dichloromethane/methanol).

Example 23

Preparation of (S)-3-amino-2-oxo-1-pyrrolidineacetic acid-N^g-L-nitroargininol, hydrochloride salt

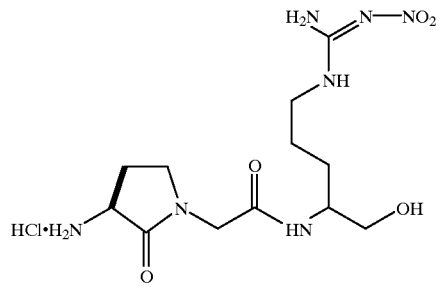

The compound of Example 22 (3.3 g, 74 mmole) was dissolved in 200 mL of ethyl acetate and 50 mL of methanol. To this solution at 0° C. was added 50 mL of ethyl acetate saturated with HCl gas. This mixtured was stirred for 30 minutes. The solvents were removed under vacuum to yield 3.1 g (100%) of the title compound as a white solid.

Example 24

Preparation of N-benzylsulfonyl-(S)-3-amino-2-oxo-1-pyrrolidineacetic acid-N^g-L-nitroargininol

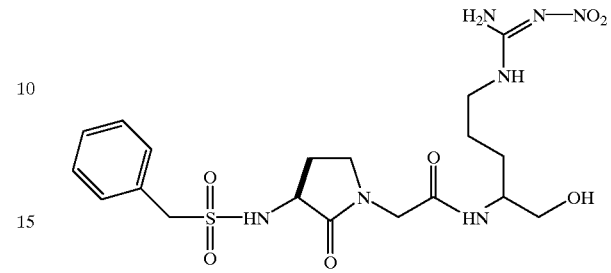

Benzylsulfonyl chloride (0.60 g 3.1 mmole), the compound of Example 23 (1 g, 2.6 mmole), 25 mL of DMF and 25 mL of acetonitrile was stirred at 25° C. To this solution was added triethylamine (1.48 mL, 10.4 mmole). The mixture was stirred for 12 hours at 25° C. and the solvent was removed under vacuum to yield a residue. This was dissolved in 100 mL of ethyl acetate and washed with water (100 mL), 10% HCl (3×100 mL), NaHCO3 (3×100mL) and Brine (100 mL). The organic phase was dried over anhydrous magnesium sulfate, filtered and evaporated under vacuum to yield a residue. This was chromatographed on silica gel (100 g), eluting with a gradient ranging from 5–15% methanol in dichloromethane to give 1.1 g (85%) of the title compound. Thin-layer chromatography gave an Rf=0.53 (silica gel; 95:5 dichloromethane/methanol).

Example 25

Preparation of N-benzylsulfonyl-(S)-3-amino-2-oxo-1-pyrrolidineacetic acid-L-argininol

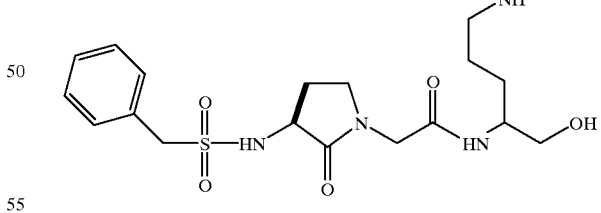

The compound of Example 24 (1.1 g, 2.2 mmole), 100 mL of methanol, 3 mL of glacial acetic acid, and 200 mg of 10% palladium on carbon was hydrogenated at 45 psi in a Parr hydrogenator for 24 hours. The organic layer was filtered through celite and washed with 100 mL of methanol. The organic layer was evaporated under vacuum to yield 1.2 g (100%) of the title compound. Thin-layer chromatography gave an Rf=0.82 (silica gel; 80:20 dichloromethane/methanol).

Example 26

Preparation of N-benzylsulfonyl-(S)-3-amino-2-oxo-1-pyrrolidineacetic acid-L-argininal

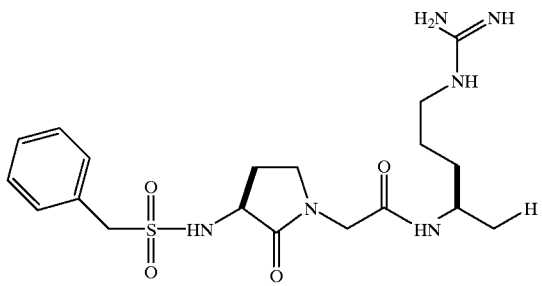

The compound of Example 25 (200 mg, 0.3 mmole), EDC (0.76 g, 3.0 mmole) and 4 mL of dimethylsulfoxide were stirred at 25° C. To this solution was added dichloroacetic acid (170 microliters, 1.5 mmole). The reaction mixture was stirred for 30 minutes. The reaction was poured into 80 mL of water, filtered and processed on an HPLC C18 50×300 mm cartridge employing a 10–40% gradient system of acetonitrile-water (containing 0.1% trifluoroacetic acid) over 20 minutes. The pure fractions were combined and lyopholized to give 130 mg of the title compound. Fast atom bombardment mass spectrometry confirmed the theoretical molecular weight of 452.

Example 27

Preparation of (S)-3-[(tert-butoxycarbonyl)amino]-hexahydro-1-azepine-2-one.

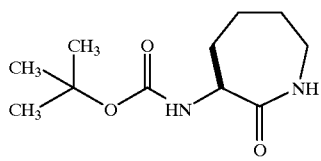

To a solution of L-(−)-alpha-amino-epsilon-caprolactam (24.36 g, 0.19 mole), obtained from Sigma, in 200 mL tetrahydrofuran and 200 mL of saturated sodium bicarbonate solution at 0° C. was added di-t-butyl dicarbonate (43.54 g, 0.20 mol) rapidly over 2 minutes. The mixture was stirred rapidly and was allowed to slowly warm to room temperature. After stirring was continued for 3 days, the volatiles were removed in vacuo, solid sodium chloride was added to saturate the aqueous phase, and it was extracted with 3×200 ml portions of ethyl acetate. The combined organic phase was washed with 2×50 mL water, 1×50 mL brine, dried over anhydrous magnesium sulfate, and evaporated to afford 37.92 g of crude product as a pale yellow solid. The combined aqueous layer was back-extracted with 200 mL of ethyl acetate, 200 mL of 20% isopropanol in dichloromethane, and dried to afford an additional 4.64 g of crude product, combined crude yield, 98%. The materials thus obtained were judged pure by TLC (Silica Gel; ethyl acetate, Rf=0.4) These were combined and recrystallized from ethyl acetate/hexanes to afford the product as a pale yellow crystalline solid, m.p. 148–150° C.

Example 28

Preparation of (S)-3-[(tert-butoxycarbonyl)amino]-hexahydro-2-oxo-1-azepineacetic acid, benzyl ester.

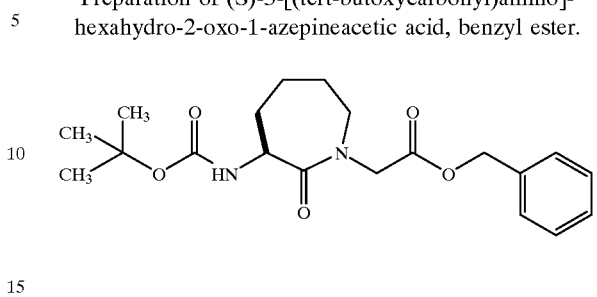

To a solution of the compound of Example 27 (12.28 g, 0.054 mol) in 215 mL dry tetrahydrofuran at ambient temperature under a $N_2$ atmosphere was added lithium is(trimethylsilyl)amide (70.0 mL of 1M solution in tetrahydrofuran, Aldrich, 0.070 mole) dropwise rapidly so as to maintain ~30° C. The addition required about 20 minutes. The solution was stirred for 15 minutes and then a solution of benzyl bromoacetate (24.65 g, 0.108 mole, 17.1 mL) in 35 mL tetrahydrofuran was added rapidly so as to maintain ~32° C. After 18 hours reaction time, the mixture was quenched with 100 mL saturated ammonium chloride solution, diluted with 600 mL of ethyl acetate, and extracted with 2×50 mL water, 1×50 mL brine, dried over anhydrous magnesium sulfate and evaporated. The crude product was purified by flash chromatography on silica gel eluting with a gradient system of 4:1 to 2:1 hexane/ethyl acetate to afford 17.41 g (86% yield) of product as a viscous yellow oil; TLC (silica gel; 1:1 ethyl acetate/hexane): Rf=0.4.

Example 29

Preparation of (S)-3-amino-hexahydro-2-oxo-1-azepineacetic acid, benzyl ester hydrochloride.

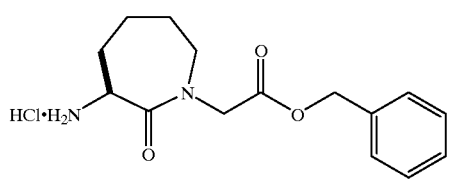

A solution of compound of Example 28 (17.04 g, 0.0453 mole) in 50 mL of ethyl acetate at 0° C. was treated with 5 N HCl in ethyl acetate (117 mL, freshly prepared, 0.585 mole) in one portion. The solution was stirred at 0° for 10 minutes and then allowed to stir at ambient temperature for 1.5 hours. The solvent was removed in vacuo, dry acetonitrile (200 mL) was added and the solvents were reevaporated. The residue was pumped at <1 mm Hg on a vacuum pump for several hours to afford 14.06 g (99.3% yield) of product as a pale yellow foam, judged pure by TLC (silica gel; 27:3:1 dichloromethane/methanol/concentrated ammonium hydroxide): Rf=0.4.

Example 30

Preparation of (S)-3-benzylsulfonylamido-hexahydro-2-oxo-1-azepineacetic acid, benzyl ester.

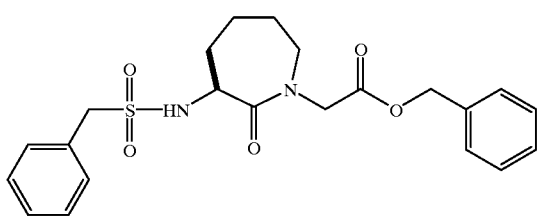

To a solution of compound of Example 29 (9.38 g, 0.030 mole) in 300 mL dry acetonitrile was added benzylsulfonyl chloride (6.29 g, 0.033 mole) and the solution was cooled to 0° C. under $N_2$. A solution of triethylamine (6.68 g, 0.066 mole, 9.20 mL) dissolved in 25 mL dry acetonitrile was added dropwise so as to maintain <5° C. The resultant mixture was stirred at 0° C. for 1 hour and then allowed to stir at ambient temperature for 9 hours. Additional portions of benzylsulfonyl chloride (572.0 mg, 3.0 mmole) and triethylamine (0.92 g, 9.0 mmole, 1.27 mL) were added, the mixture was stirred for 14 hours, filtered, and evaporated. The residue was purified by flash chromatography on silica gel using a gradient system of dichloromethane to 10% ethyl acetate in dichloromethane to afford 11.10 g (86% yield) of product as a stiff yellow oil, judged pure by TLC (silica gel; 9:1 dichloromethane/ethyl acetate): Rf=0.4.

Example 31

Preparation of (S)-3-benzylsulfonylamido-hexahydro-2-oxo-1-azepineacetic acid ("BnSO$_2$-norLeu(cyclo)-Gly").

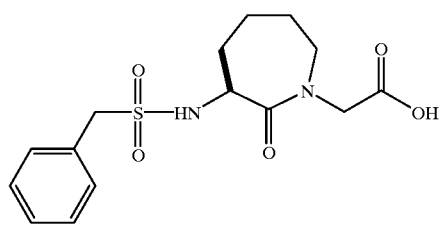

To a solution of Example 30 (11.06 g, 0.0257 mole) in 200 mL ethanol was added 10% Pd/C (1.11 g) and the mixture was hydrogenated at 40 psi on the Parr Shaker for 5 hours. The catalyst was filtered off and the solvents were removed to afford 8.81 g (~quantitative yield) of product as a colorless foam, judged pure by TLC (silica gel: 27:3:1 dichloromethane/methanol/acetic acid): Rf=0.5.

Example 32

Preparation of N-(BnSO$_2$-norLeu(cyclo)-Gly) N$^g$-nitro-L-argininal ethyl cyclol.

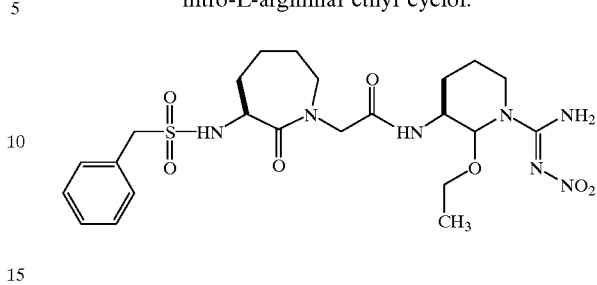

The compound of Example 31 (6.81 g, 0.020 mole) was dissolved in 80 mL of acetonitrile and treated with the compound of Example 15 (Ng-nitro-L-argininal ethyl cyclol, hydrochloride salt) (5.89 g, 0.022 mole), 1-hydroxybenzotriazole monohydrate (3.06 g, 0.020 mol) and 1-ethyl-3-(3-dimethylamino-propyl)carbodiimide hydrochloride salt (5.75 g, 0.030 mole). The solution was stirred for 20 minutes at ambient temperature, and was then treated with N,N-diisopropylethylamine (12.83 g, 0.10 mole, 17.3 mL). The reaction was stirred for 20 hours, diluted with 700 mL ethyl acetate and washed with 2×50 mL each of 1N HCl, saturated sodium bicarbonate, and brine. The organic layer was dried over anhydrous magnesium sulfate, filtered, and concentrated in vacuo to provide a yellow foam which was purified by flash chromatography on silica gel using 95:5 dichloromethane/ethanol as eluent to afford 7.54 g (68% yield) of product as a colorless foam, judged pure by TLC (silica gel; 9:1 dichloromethane/ethanol): Rf=0.40.

Example 33

Preparation of N-(BnSO$_2$-norLeu(cyclo)-Gly)-L-argininal ethyl cyclol.

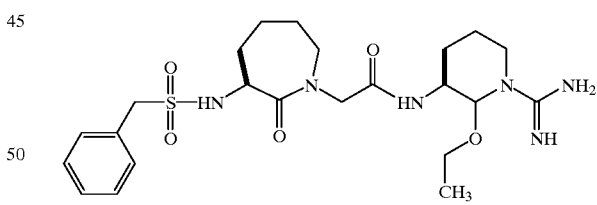

The compound of Example 32 (7.54 g, 0.0136 mole) was dissolved in 200 mL of 4:1:1: ethanol/water/acetic acid and 10% Pd/C catalyst (3.8 g) was added. This mixture was hydrogenated on a Parr shaker at 50 psi for 19 hours. The catalyst was filtered off and the filtrate was evaporated. The residue was dissolved in a mixture of 1:1 ethanol/acetonitrile, reevaporated, and pumped at <1 mm Hg on a vacuum pump for 3 days to afford 8.20 g (~Quantitative crude yield) of product as a colorless, amorphous solid which was judged to be about 95 % pure by TLC (silica gel; 20:10:2 dichloromethane/methanol/concentrated ammonium hydroxide); Rf=0.48 and 0.43.

Example 34

Preparation of N-(BnSO$_2$-norLeu(cyclo)-Gly)-L-argininal.

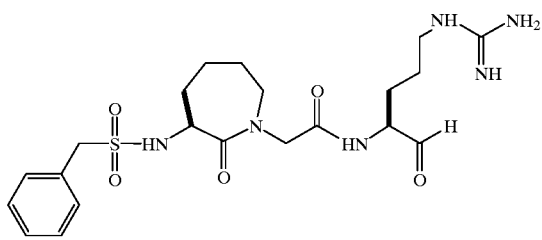

The compound of Example 33 (2.84 g, 5.0 mmole) was dissolved in 3N HCL (80 mL) and stirred at ambient temperature for 2.5 hours. Purification via reverse phase HPLC on a 50×300 mm C18 column using a 10–30% gradient of acetonitrile/water (containing 0.1% trifluoroacetic acid) over 1 hour yielded 2.18 g (74% yield) of product as a colorless, amorphous solid. RP/HPLC analysis showed three peaks for the product. Fast atom bombardment mass spectrometry confirmed the theoretical molecular weight of 480.

Example 35

General Procedure for Reaction of (S)-3-amino-2-oxo-hexahydro-1-azepineacetic acid, benzyl ester hydrochloride with Sulfonyl or Sulfamoyl Chlorides.

To a solution of the compound of Example 29 (9.38 g, 0.030 mole) in 300 mL dry acetonitrile is added the appropriate sulfonyl or sulfamoyl chloride listed below (0.033 mole) and the solution is cooled to 0° C. under N$_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed below, intermediates having the formula given below are made:

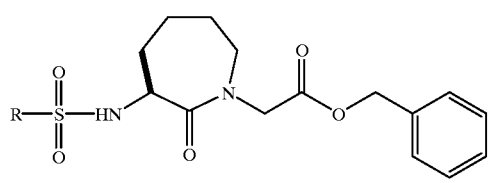

| R = | Starting material (amount needed) |
|---|---|
| phenyl | benzenesulfonyl chloride (5.83 g) |
| 1-naphthyl | 1-naphthylsulfonyl chloride (7.48 g) |
| 2-naphthyl | 2-naphthylsulfonyl chloride (7.48 g) |
| 2-carbomethoxyphenyl | 2-carbomethoxybenzenesulfonyl chloride (7.74 g) |
| 2-carbomethoxybenzyl | 2-carbomethoxybenzylsulfonyl chloride (8.21 g) |
| 2-trifluoromethylphenyl | 2-trifluoromethylbenzenesulfonyl chloride (8.07 g) |
| 2-trifluoromethylbenzyl | 2-trifluoromethylbenzylsulfonyl chloride (8.54 g) |
| 2-phenylethyl | 2-phenylethylsulfonyl chloride (6.75 g) |
| cyclohexylmethyl | cyclohexylmethylsulfonyl chloride (6.49 g) |
| cyclohexylamino | cyclohexylsulfamoyl chloride (6.52 g) |
| 2-thiophenemethyl | 2-Thiophenemethylsulfonyl chloride (6.49 g) This intermediate is prepared by reaction of 2-chloromethylthiophene (K. B. Wiberg, Org. Syntheses, 29, 31, 1949) with Na$_2$SO$_3$ to afford the corresponding sodium sulfonate salt (cf. S. Zuffanti, J. Am. Chem. Soc., 62, 1044, 1940), followed by standard treatment with PCl$_5$. |
| Perfluorobutyl | Perfluoro-1-butanesulfonyl fluoride (9.97 g) |
| Pentafluorobenzyl | Pentafluorobenzylsulfonyl chloride (9.26 g) |
| Phenylamino | Phenylsulfamoyl chloride (6.32 g) |
| 3-Carbomethoxybenzyl | 3-Carbomethoxybenzylsulfonyl chloride (8.21 g) |
| 3-Trifluoromethylbenzyl | 3-Trifluoromethylbenzylsulfonyl chloride (8.54 g) |
| 2-Methylbenzyl- | 2-Methylbenzylsulfonyl chloride (6.75 .g) |
| 3-Methylbenzyl- | 3-Methylbenlylsulfonyl chloride (6.75 g) |
| 2-Methoxybenzyl- | 2-Methoxybenzylsulfonyl chloride (7.28 g) |
| 3-Methoxybenzyl- | 3-Methoxybenzylsulfonyl chloride (7.28 g) |
| 2-Chlorobenzyl- | 2-Chlorobenzylsulfonyl chloride (7.43 g) |
| 3-Chlorobenzyl- | 3-Chlorobenzylsulfonyl chloride (7.43 g) |
| 2-Methyl-5-fluoro-benzyl- | 2-Methyl-5-fluorobenzyl-sulfonyl chloride (7.35 g) |
| 2-Methyl-5-methoxy-benzyl- | 2-Methyl-5-methoxybenzyl-sulfonyl chloride (7.75 g) |
| 3-Carbomethoxy-5-methoxy-6-trifluoromethyl benzyl- | 3-Carbomethoxy-5-methoxy-6-trifluoromethylbenzyl sulfonyl chloride (11.44 g) |

Example 36

General Procedure for Preparation of Compounds of the Present Invention.

Following the four-step protocol outlined in Examples 31 through 34 (hydrogenation, coupling, hydrogenation and hydrolysis), the intermediates of Example 35 are used to synthesize the following compounds of the present invention (as their trifluoroacetic acid salts):

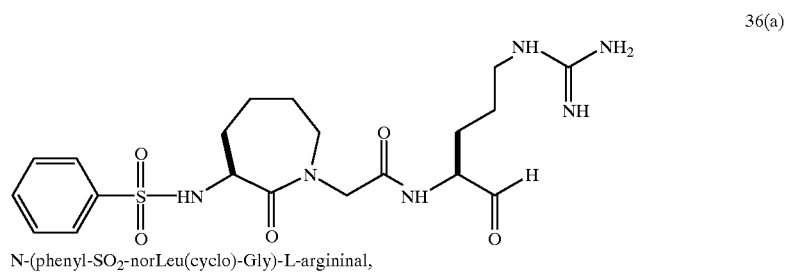
N-(phenyl-SO$_2$-norLeu(cyclo)-Gly)-L-argininal,
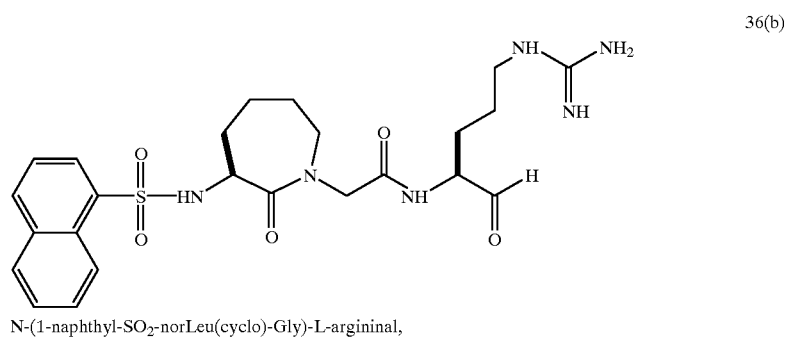
N-(1-naphthyl-SO$_2$-norLeu(cyclo)-Gly)-L-argininal,
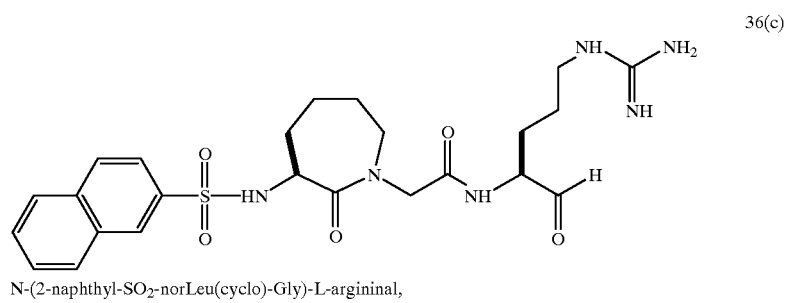
N-(2-naphthyl-SO$_2$-norLeu(cyclo)-Gly)-L-argininal,
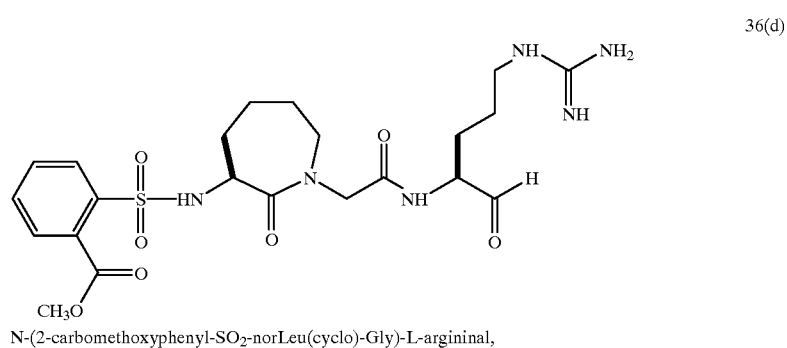
N-(2-carbomethoxyphenyl-SO$_2$-norLeu(cyclo)-Gly)-L-argininal,
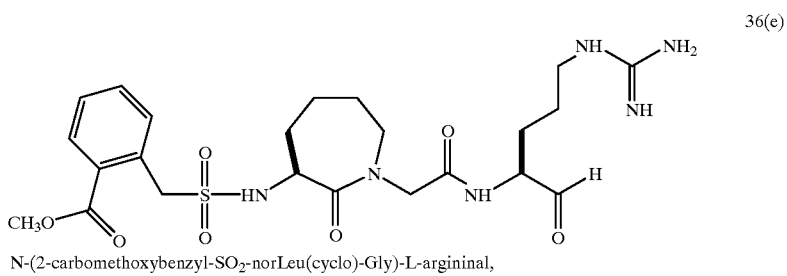
N-(2-carbomethoxybenzyl-SO$_2$-norLeu(cyclo)-Gly)-L-argininal,

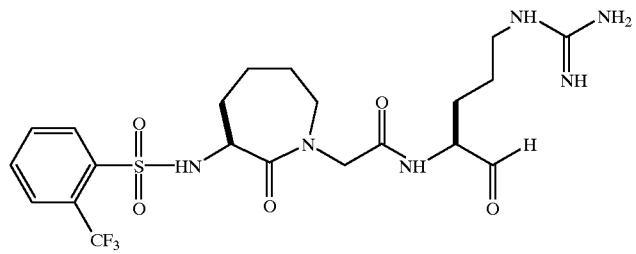
N-(2-trifluoromethylphenyl-SO$_2$-norLeu(cyclo)-Gly)-L-argininal,
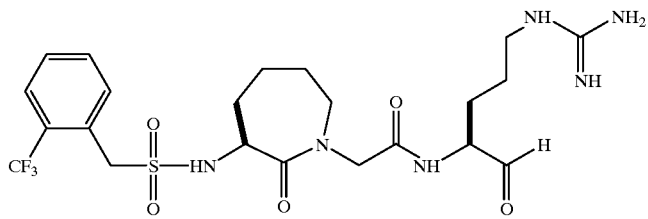
N-(2-trifluoromethylbenzyl-SO$_2$-norLeu(cyclo)-Gly)-L-argininal,
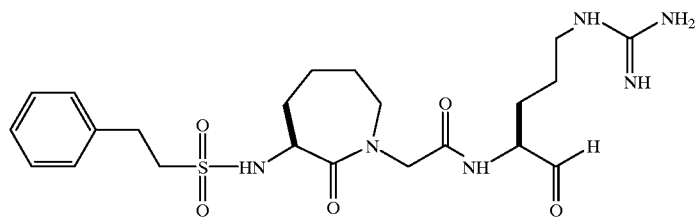
N-(phenylethyl-SO$_2$-norLeu(cyclo)-Gly)-L-argininal,
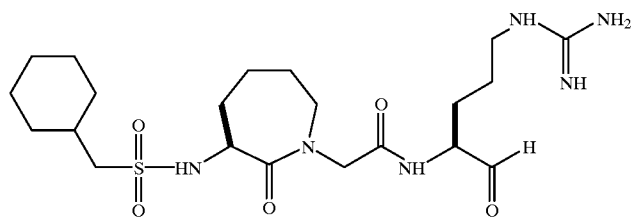
N-(cyclohexmethyl-SO$_2$-norLeu(cyclo)-Gly)-L-argininal,
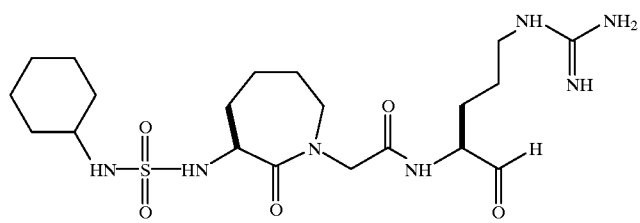
N-(cyclohexlamino-SO$_2$-norLeu(cyclo)-Gly)-L-argininal,
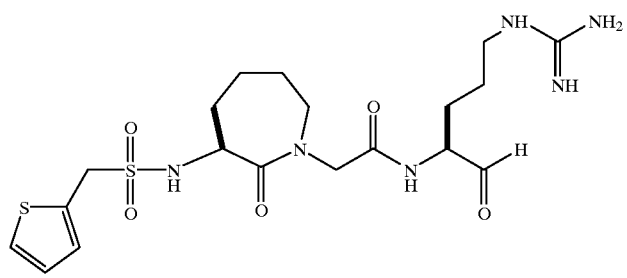
N-(2-thiophenemethyl-SO$_2$-norLeu(cyclo)-Gly)-L-argininal, -continued
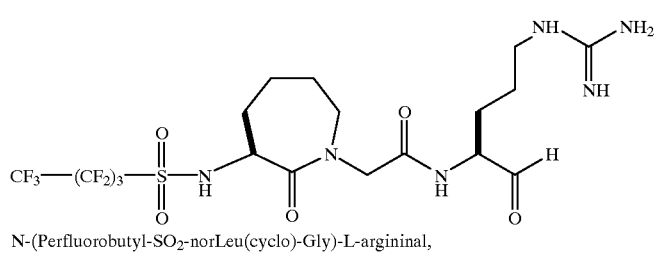
N-(Perfluorobutyl-SO$_2$-norLeu(cyclo)-Gly)-L-argininal,   36(l)
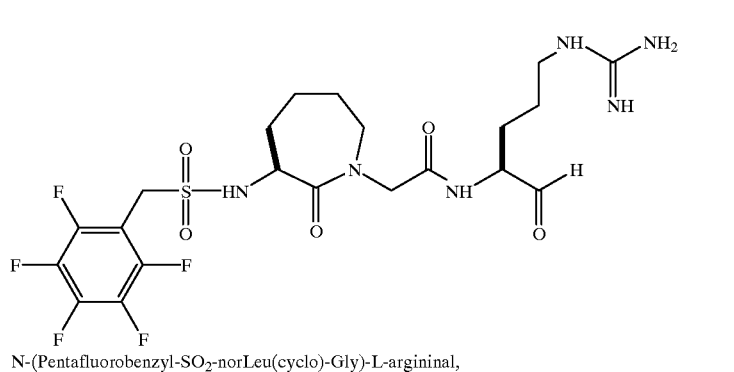
N-(Pentafluorobenzyl-SO$_2$-norLeu(cyclo)-Gly)-L-argininal,   36(m)
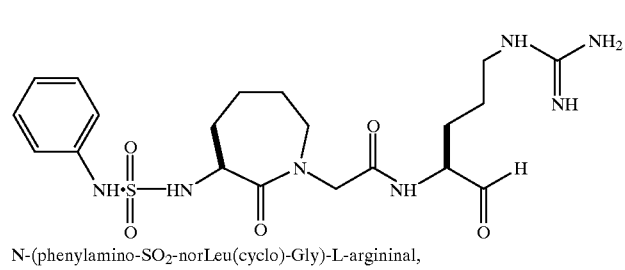
N-(phenylamino-SO$_2$-norLeu(cyclo)-Gly)-L-argininal,   36(n)
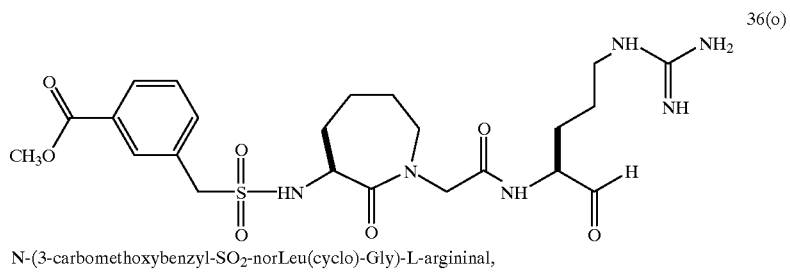
N-(3-carbomethoxybenzyl-SO$_2$-norLeu(cyclo)-Gly)-L-argininal,   36(o)
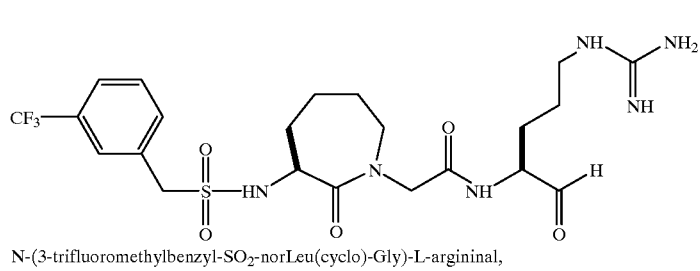
N-(3-trifluoromethylbenzyl-SO$_2$-norLeu(cyclo)-Gly)-L-argininal,   36(p)

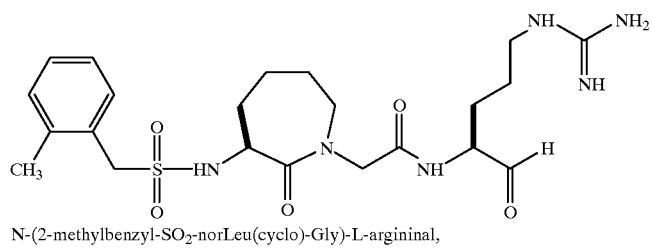
N-(2-methylbenzyl-SO$_2$-norLeu(cyclo)-Gly)-L-argininal,
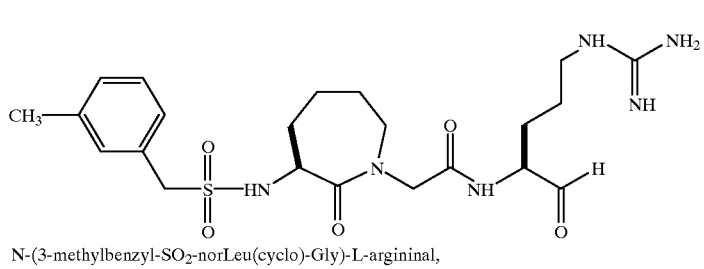
N-(3-methylbenzyl-SO$_2$-norLeu(cyclo)-Gly)-L-argininal,
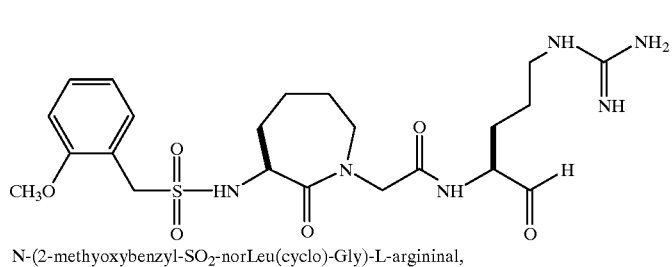
N-(2-methyoxybenzyl-SO$_2$-norLeu(cyclo)-Gly)-L-argininal,
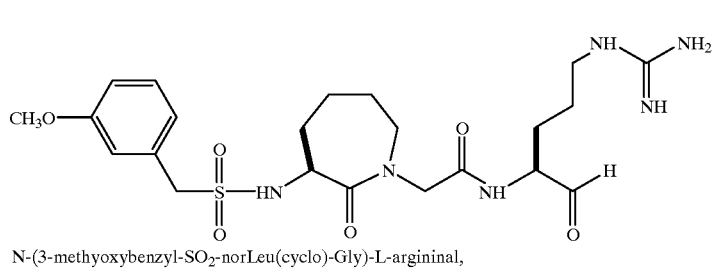
N-(3-methyoxybenzyl-SO$_2$-norLeu(cyclo)-Gly)-L-argininal,
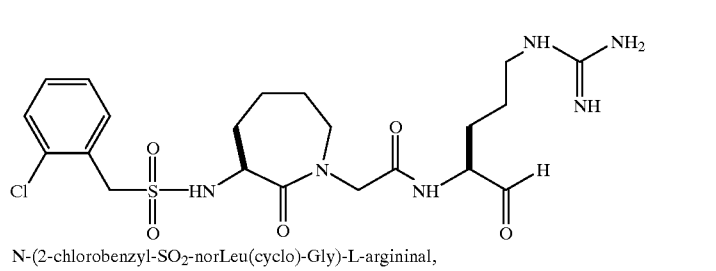
N-(2-chlorobenzyl-SO$_2$-norLeu(cyclo)-Gly)-L-argininal,
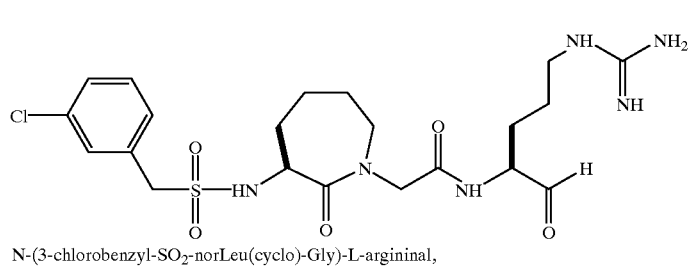
N-(3-chlorobenzyl-SO$_2$-norLeu(cyclo)-Gly)-L-argininal,

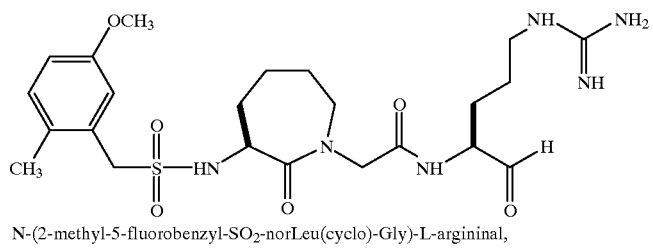

N-(2-methyl-5-fluorobenzyl-SO$_2$-norLeu(cyclo)-Gly)-L-argininal, 36(w)

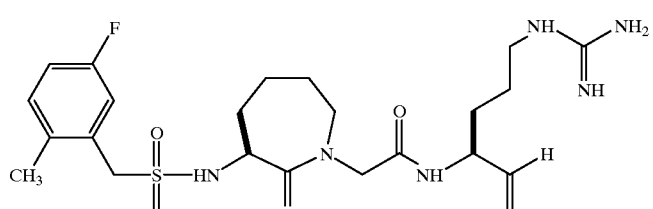

N-(2-methyl-5-methoxybenzyl-SO$_2$-norLeu(cyclo)-Gly)-L-argininal, 36(x)

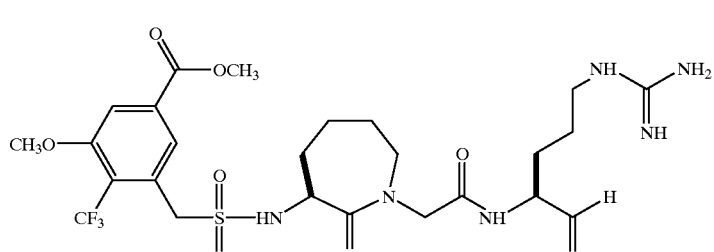

N-(3-carbomethoxy-5-methoxy-6-trifluoro-methylbenzyl-SO$_2$-norLeu(cyclo)-Gly)-L-argininal, 36(y)

Example 37

Preparation of (S)-3-[(tert-butoxycarbonyl) amino]-2-oxo-1-azepineacetic acid ("Boc-norLeu(cyclo)-Gly").

To a solution of the compound of Example 28 (3.76 g, 0.010 mol) in 50 mL EtOH was added 10% Pd/C (0.76 g) and the mixture was hydrogenated at 40 PSI on the Parr Shaker for 2 hours. The catalyst was filtered off and the solvents were removed to afford 2.77 g (97% yield) of product as a colorless foam. TLC (silica gel: CH$_2$Cl$_2$, MeOH, HOAc: 27, 3, 1).R$_f$=0.45.

Example 38

Preparation of N-(Boc-norLeu(cyclo)-Gly)-N$^g$-nitro-L-argininal ethyl cyclol.

The compound of Example 37 (5.73 g, 0.020 mol) is dissolved in 80 mL of CH$_3$CN and treated with the compound of Example 15 (N$^g$-nitro-L-argininal ethyl cyclol, hydrochloride salt) (5.89 g, 0.022 mol), 1-Hydroxybenzotriazole monohydrate (3.06 g, 0.020 mol) and 1-ethyl-3-(3-dimethylamino-propyl)carbodiimide hydrochloride salt (5.75 g, 0.030 mol). The solution is stirred for 20 minutes at ambient temperature, and is then treated with N,N-diisopropylethyl amine (12.83 g, 0.10 mol, 17.3 mL). The reaction is stirred for 24 hours, diluted with 700 mL EtOAc and washed with 2×50 mL each of 1N HCl, saturated NaHCO$_3$, and brine. The organic layer is dried over MgSO$_4$, filtered, and concentrated in vacuo to provide a yellow foam which is purified by flash chromatography on silica gel using CH$_2$Cl$_2$, EtOH: 95, 5 as eluent to afford the product as a colorless foam, judged pure by TLC (silica gel; CH$_2$Cl$_2$, EtOH: 9, 1).

Example 39

Preparation of N-(Boc-norLeu(cyclo)-Gly)-L-argininal ethyl cyclol.

The compound of Example 38 (6.79 g, 0.0136 mol) is dissolved in 200 mL of EtOH, H$_2$O, HOAc: 4, 1, 1. Pd/C catalyst (3.4 g of 10%) is added and the mixture is hydrogenated on a Parr shaker at 50 PSI for 22 hours. The catalyst is filtered off and the filtrate evaporated. The residue is dissolved in a mixture of EtOH, CH$_3$CN: 1,1; reevaporated, and pumped at <1 mm Hg on a vacuum pump for 3 days to afford ~Quantitative crude yield of product as a colorless, amorphous solid which is judged ca. 95% pure by TLC (silica gel; CH$_2$Cl$_2$, MeOH, NH$_4$OH: 20, 10, 2).

Example 40(a)

Preparation of N-(norLeu(cyclo)-Gly)-L-argininal.

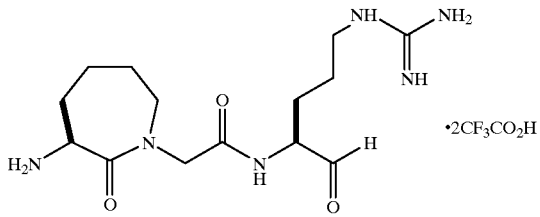

The compound of Example 39 (2.57 g, 5.0 mmol) is dissolved in 3N HCL (80 mL) and stirred at ambient temperature for 2.5 hours. Purification via reverse phase HPLC on a 50×300 mm C18 column using a 0–20% gradient of acetonitrile/water/0.1% TFA over 1 hour yields the title compound as a colorless, amorphous solid. RP/HPLC analysis shows three peaks for the product.

Example 40(b)

Preparation of N-(norVal(cyclo)-Gly)-L-argininal

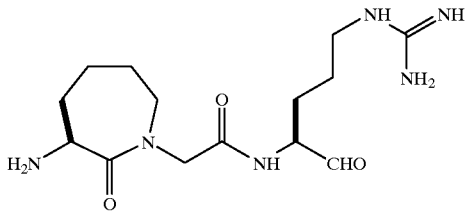

Starting with the compound of Example 1, and following the three step procedure described in Examples 38, 39, and 40 (coupling, hydrogenation, hydrolysis), the title compound was prepared as a colorless, amorphous solid. RP/HPLC analysis showed three peaks for the product. Fast atom bombardment mass spectrometry comfirmed the theoretical molecular weight of 312.

Example 41

Preparation of (S)-3-[(tert-butoxycarbonyl)-N-methylamino]-2-oxo-1-azepineacetic acid, benzyl ester.

To a suspension of sodium hydride (1.26 g of 60% oil dispersion washed 3× with dry hexane, 0.0315 mol) in 60 mL dry THF and 6 mL dry DMF at 0° under $N_2$ is added a solution of the compound of Example 28 (11.29 g, 0.030 mol) in 30 mL dry THF rapidly dropwise so as to maintain 5–10°. After a further 10 minutes, the mixture is allowed to warm to ambient temperature, stirred for 1 hour, and recooled to 0°. A solution of iodomethane (4.68 g, 0.033 mol, 2.05 mL) in 5 mL dry THF is added dropwise so as to maintain <5°, and after 1 hour the ice bath is removed and the mixture is stirred at ambient temperature for 24 hours. The solution is diluted with 400 mL $Et_2O$, extracted with 2×50 mL each of water and brine. The organic layer is dried over $MgSO_4$, filtered, and concentrated in vacuo to provide a crude product which is purified by flash chromatography on silica gel, eluting with an ethyl acetate, hexane gradient to afford the product as a stiff yellow oil, judged pure by TLC (silica gel; EtOAc, Hex:1,1).

Example 42

Preparation of (S)-3-[(tert-butoxycarbonyl)-N-methylamino]-2-oxo-1-azepineacetic acid ("Boc-N-Me-norLeu(cyclo)-Gly").

To a solution of the compound of Example 41 (11.71 g, 0.030 mol) in 200 mL EtOH is added Pd/C catalyst (1.17 g of 10%) and the mixture is hydrogenated at 40 PSI on the Parr Shaker for 6 hours. The catalyst is filtered off and the solvents are removed to afford a quantitative yield of product as a colorless foam, pure by TLC (silica gel: $CH_2Cl_2$, MeOH, HOAc: 27, 3, 1).

Example 43

Preparation of N-(Boc-N-Me-norLeu(cyclo)-Gly)-$N^g$-nitro-L-argininal ethyl cyclol.

The compound of Example 42 (6.01 g, 0.020 mol) is dissolved in 80 mL of $CH_3CN$ and treated with the compound of Example 15 ($N^g$-nitro-L-argininal ethyl cyclol, hydrochloride salt) (5.89 g, 0.022 mol), 1-Hydroxybenzotriazole monohydrate (3.06 g, 0.020 mol) and 1-ethyl-3-(3-dimethylamino-propyl) carbodiimide hydrochloride salt (5.75 g, 0.030 mol). The solution is stirred for 20 minutes at ambient temperature, and is then treated with N,N-diisopropylethyl amine (12.83 g, 0.10 mol, 17.3 mL). The reaction is stirred for 22 hours, diluted with 700 mL EtOAc and washed with 2×50 mL each of 1N HCl, saturated $NaHCO_3$, and brine. The organic layer is dried over $MgSO_4$, filtered, and concentrated in vacuo to provide a yellow foam which is purified by flash chromatography on silica gel using $CH_2Cl_2$, EtOH: 95, 5 as eluent to afford the product as a colorless foam, judged pure by TLC (silica gel; $CH_2Cl_2$, EtOH: 9, 1).

Example 44

Preparation of N-(Boc-N-Me-norLeu(cyclo)-Gly)-L-argininal ethyl cyclol.

The compound of Example 43 (6.99 g, 0.0136 mol) is dissolved in 200 mL of EtOH, $H_2O$, HOAc: 4, 1, 1. Pd/C catalyst (3.5 g of 10%) is added and the mixture is hydrogenated on a Parr shaker at 50 PSI for 26 hours. The catalyst is filtered off and the filtrate evaporated. The residue is dissolved in a mixture of EtOH, $CH_3CN$: 1,1; reevaporated, and pumped at <1 mm Hg on a vacuum pump for 3 days to afford ~Quantitative crude yield of product as a colorless, amorphous solid which is judged ca. 95% pure by TLC (silica gel; $CH_2Cl_2$, MeOH, $NH_4OH$: 20, 10, 2).

Example 45

Preparation of N-(N-Me-norLeu(cyclo)-Gly)-L-argininal.

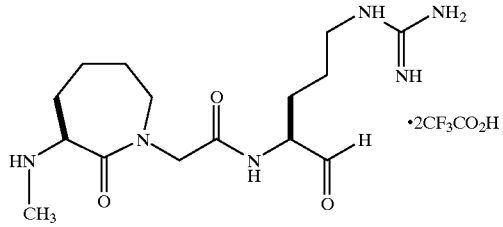

The compound of Example 44 (2.64 g, 5.0 mmol) is dissolved in 3N HCL (80 mL) and stirred at ambient temperature for 2.5 hours. Purification via reverse phase HPLC on a 50×300 mm C18 column using a 0–20% gradient of acetonitrile/water/0.1% TFA over 1 hour yields the title compound as a colorless, amorphous solid. RP/HPLC analysis shows three peaks for the product.

Examples 46 through 55 describe synthesis of N-[D,L-3-Amino-3-benzyl-2-oxo-1-piperidineacetyl]-L-argininal bis-trifluoroacetate salt (30), or D,L-α-Benzyl-norVal(cyclo)Gly-L-argininal bis-trifluoroacetate salt (30). The synthesis scheme is shown in FIG. 10.

Example 46

Preparation of (S)-3-[(tert-butoxycarbonyl)amino]-2-oxo-1-piperidineacetic acid (21)

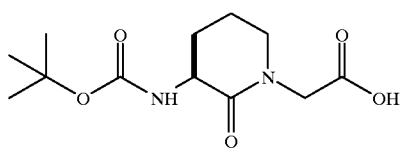

Compound 21 was made according to the protocol of Example 1.

Example 47

Preparation of (S)-3-Amino-2-oxo-1-piperidineacetic acid, Ethyl ester (22): OR norVal (cyclo)Gly-O-ethyl ester (22)

To a solution of compound 21 (5.45 g, 0.020 mol) in 20 mL of dry ethanol at 0° was added ethanolic 12N HCl (50.0 mL, 0.60 mol). The solution was stirred at 0° for one hr and then allowed to stir at ambient temperature for 3 hrs. The solvent was evaporated, the residue was twice redissolved in a mixture of ethanol, acetonitrile: 1,1 and reevaporated. After vacuum pumping at <1mm Hg for 24 hrs, 4.84 g (~quantitative crude yield) of product 22 was obtained as a sticky light brown foam. TLC (silica; $CH_2Cl_2$, methanol, conc $NH_4OH$: 27, 3, 1): Rf=0.35.

Example 48

Preparation of (S)-3-Benzylideneamino-2-oxo-1-piperidineacetic acid. Ethyl ester (23); OR N-Benzylidene-norVal(cyclo)Gly-O-ethyl ester (23)

To a solution of 22 (4.7586 g, 0.0200 mol) and benzaldehyde (2.1224 g, 0.0200 mol, 2.03 mL) in 50 mL $CH_2Cl2$ at 0° under $N_2$ was added anhydrous $MgSO_4$ (5.0 g) and $Et_3N$ (4.05 g, 0.040 mol, 5.58 mL). The mixture was stirred from 0° to ambient temperature over 21 hrs, filtered under $N_2$, and the solvent was evaporated. The residue was dissolved in 300 mL of diethyl ether, extracted with 50 mL portions of water (3×), brine, dried over $MgSO_4$, filtered under $N_2$ and evaporated to afford 5.13 g (89% yield) of product 23 as a light yellow viscous oil. The material was hydrolytically labile and was stored at 0° under a $N_2$ atmosphere.

Example 49

Preparation of D, L-3-Benzylideneamino-3-benzyl-2-oxo-1-piperidineacetic acid, Ethyl ester (24): OR D,L-N-Benzylidene-α-benzyl-norVal(cyclo)Gly-O-ethyl ester (24)

To a solution of KOt-Bu (5.25 mL of 1M in THF, 5.25 mmol) at room temperature under $N_2$ was added a solution of 23 (1.4417 g, 5.00 mmol) in 5 mL of anhydrous THF rapidly dropwise so as to maintain ~30°. The resultant dark red-brown solution was stirred at ambient temperature for 1 hr and then benzyl bromide (855.2 mg, 5.00 mmol, 0.60 mL) was added in one portion. A smooth exotherm to 45° was noted along with an immediate color discharge and formation of a precipitate. After 22 hrs reaction time, the mixture was diluted with diethyl ether, extracted with 25 mL portions of water (2×), brine, dried over $MgSO_4$, filtered, and evaporated to afford 1.6834 g (89% yield) of product 24 as a viscous yellow oil. The material was hydrolytically labile and was stored at 0° under a $N_2$ atmosphere.

Example 50

Preparation of D,L-3-Amino-3-benzyl-2-oxo-1-piperidineacetic acid. Ethyl ester, hydrochloride salt (25); OR D,L-α-Benzyl -norVal(cyclo)Gly-O-ethyl ester, hydrochloride salt (25);

A mixture of 24 (1.5722 g, 4.15 mmole) in 5 mL of diethyl ether and 50 mL of 1N HCl was vigorously stirred at room temperature for 2 hrs. The solution was extracted with 3×50 mL of diethyl ether, the aqueous solution was briefly placed on a roto-vap to remove traces of ether, and was then lyophilized for 3 days to afford a yellow foam which was dissolved in 25 mL of dry ethanol, cooled to 0° and treated with ethanolic 12N HCl (3.46 mL, 41.5 mmol). The solution was allowed to warm to ambient temperature and after 14 hrs the solvent was evaporated. A portion of ethanol, acetonitrile:1,1 was added, the solution was reevaporated and the residue was pumped in high vacuum for 12 hrs at <1 mm Hg to afford 1.3013 g (96% yield) of product 25 as a yellow glass. TLC (silica; $CH_2C12$, MeOH, conc $NH_4OH$: 27, 3, 1) Rf=0.55.

Example 51

Preparation of D, L-3-(tert-Butoxycarbonyl)amino-3-benzyl-2-oxo-1-piperidineacetic acid. Ethyl ester (26): OR D. L-Boc-α-benzyl-norVal (cyclo)Gly-O-ethyl ester (26)

To a solution of 25 (653.6 mg, 2.00 mmole) in 6 mL of THF was added 2 mL of saturated $NaHCO_3$ and di-tert-butyl dicarbonate (458.3 mg, 2.10 mmole). The mixture was stirred at room temperature for 17 hrs, diluted with 100 mL of ethyl acetate and then extracted with 2×10 mL brine, dried over $MgSO_4$, filtered and evaporated. The residue was purified on flash silica gel chromatography using a gradient of hexane, ethyl acetate: 9, 1 to 4, 1 and afforded 597.5 mg (77% yield) of 26 as a colorless, amorphous solid. TLC (silica;

hexane, ethyl acetate: 1, 1) Rf=0.45.

Example 52

Preparation of D, L-3-(tert-Butoxycarbonyl)amino-3-benzyl-2-oxo-1-piperidineacetic acid (27): OR D. L-Boc-α-benzyl-norVal (cyclo) Gly-OH (27)

To a solution of 26 (577.9 mg, 1.48 mmole) in 8 mL of ethanol at 0° was added 1M LiOH solution (3.7 mL, 3.7 mmol). The solution was stirred at 0° for 30 min and then allowed to stir at ambient temperature for 2 hrs. Dowex 50×8–400 ($H^+$form, 3.0 g) was added and after stirring for 15 min the resin was filtered, washed with fresh ethanol, water: 1, 1 and the filtrate was evaporated. The residue was pumped in high vacuum at <1mm Hg for 20 hrs with occasional gentle heating to afford 524.4 mg (98% yield) of product 27 as a colorless, amorphous solid. TLC (silica: $CH_2Cl_{12}$, methanol, acetic acid: 27, 3, 1) Rf=0.55.

Example 53

Preparation of N-[D, L-3-(tert-Butoxycarbonyl) amino-3-benzyl -2-oxo-1-piperidineacetyl]-$N^g$-nitro-L-argininal ethyl cyclol (28); OR D, L-Boc-α-benzyl -norVal(cyclo)Gly-$N^g$-nitro-L-argininal ethyl cyclol (28)

To a solution of 27 (510.0 mg, 1.407 mmol) in 14 mL of anhydrous acetonitrile at room temperature under $N_2$ was added $N^g$-nitro-L-argininal ethyl cyclol (452.4 mg, 1.69 mmol), 1-hydroxybenzotriazole hydrate (215.9 mg, 1.41 mmol) and 1-ethyl-3-(3-dimethylaminopropyl) carbodiimide hydrochloride (405.2 mg, 2.12 mmol). After stirring the mixture for 15 min, N,N-diisopropylethylamine (727.4 mg, 5.64 mmol, 0.98 mL) was added and the resultant clear light brown solution was stirred at room temperature for 3 days. The reaction was diluted with 100 mL of ethyl acetate, extracted with 25 mL portions of 0.1 N HCl (2×), saturated NaHCO3 (2×), water , brine, dried over $MgSO_4$, filtered and evaporated. The crude product was purified by flash chromatography on silica gel using a $CH_2Cl_2$, EtOH: 98, 2 to 95,5 gradient system to afford 644.9 mg of product as a light yellow foam. Trituration with two small portions of diethyl ether afforded 540.5 mg (67% yield) of 28 as a colorless, amorphous solid; TLC (silica; ethyl acetate) Rf =0.27.

Example 54

Preparation of N-[D, L-3-(tert-Butoxycarbonyl) amino-3-benzyl -2-oxo-1-piperidineacetyl]-L-argininal ethyl cyclol, acetate salt (29) OR D, L-Boc-α-benzyl-norVal(cyclo)Gly-L-argininal ethyl cyclol acetate salt (29)

To a solution of 28 (508.5 mg, 0.8833 mmol) in 40 mL of ethanol, acetic acid, water: 4, 1, 1 was added 10% Pd/C (254 mg). The mixture was hydrogenated at 60 PSI on a Parr shaker apparatus for 8 hrs, filtered and the solvents were evaporated. The residue was dissolved in ethanol, acetonitile: 1, 1, reevaporated, and pumped at <1 mm Hg on a vacuum pump for 24 hrs to afford 562.5 mg (~Quantitative crude yield) of product 29 as a colorless, amorphous solid. TLC (silica; $CH_2Cl_2$, methanol, conc $NH_4OH$: 20, 10, 2) Rf=0.45, 0.30 (2 isomers).

Example 55

Preparation of N-[D, L-3-Amino-3-benzyl -2-oxo-1-piperidineacetyl]-L-argininal bis-trifluoroacetate salt (30) OR D, L-α-Benzyl -norVal(cyclo)Gly-L-argininal bis-trifluoroacetate salt (30)

Compound 29 (514.4 mg, 0.871 mmol) was added to 30 mL of 3 N HCl at ambient temperature. The solution was stirred for 3 hrs, filtered, and the filtrate was purified by reverse phase HPLC on a 50×300 mm C18 column using a 0–18% gradient of acetonitrile/water (containing 0.1% trifluoroacetic acid) over one hr and afforded 64 mg (12% yield) of product 30 as a colorless, amorphous solid. RP/HPLC analysis showed 5 peaks for the two isomeric products. Mass spectrometry confirmed the theoretical molecular weight of 402.

Examples 56 through 64 describe the synthesis of N-[D, L-3-Amino-3-benzyl-hexahydro-2-oxo-azepine-1-acetyl]-L-argininal, bis-trifluoroacetate salt (39), or D, L-α-Benzyl-norLeu (cyclo)Gly-L-argininal bis-trifluoroacetate salt (39). The synthesis scheme is shown in FIG. 11.

Example 56

Preparation of N-Benzylidene-α-amino-ε-caprolactam (31)

A solution of α-amino-ε-caprolactam (31.42 g, 0.245 mol) and benzaldehyde (26.00 g, 0.245 mol) in 490 mL of benzene was stirred and azeotropically refluxed with a Dean-Stark trap for 4 hrs. The solvent was evaporated and the residue was pumped in vacuum at <1mm Hg for 24 hrs to afford 52.98 g (Quantitative yield) of product 31 as a very stiff golden-yellow oil. The material was hydrolytically unstable and was stored at 0° under $N_2$.

Example 57

Preparation of D, L-α-Benzyl-N-benzylidene-α-amino-ε-caprolactam (32)

To a solution of 31 (21.63 g, 0.100 mol) in 400 mL of anhydrous THF at room temperature under $N_2$ was added lithum bis-(trimethylsilyl)amide (105.0 mL of 1 M THF solution, 0.105 mol) rapidly dropwise over 30 min so as to maintain ~30°. The resultant orange-red solution was stirred at ambient temperature for 2 hrs, cooled to 0°, and a solution of benzyl bromide (17.10 g, 0.10 mol, 11.9 mL) in 75 mL of anhydrous THF was added dropwise rapidly over 30 min so as to maintain <5°. The reaction was stirred at 0° for 2 hrs and then allowed to warm to ambient temperature for 20 hrs. The reaction mixture was quenched with 100 mL of saturated $NH_4Cl$, diluted with 1.5 L of ethyl acetate, and extracted with 100 mL portions of water (2×), brine (2×), dried over $MgSO_4$, filtered and evaporated to afford 27.73 g of crude product as a yellow solid. Recrystallization from diethyl ether afforded a first crop of 13.80 g of colorless solid, mp 140–142°. Trituration of the residue with diethyl ether, hexane afforded second and third crops of solid providing a total of 14.66 g (48% yield) of product 32. The material was hydrolytically unstable and was stored at 0° under $N_2$.

Example 58

Preparation of D, L-α-Amino-α-benzyl-ε-caprolactam, hydrochloride salt (33)

To a solution of 32 (14.60 g, 0.0476 mol) in 50 mL of diethyl ether was added 200 mL of 1N HCl. The solution was stirred vigorously at room temperature for 5 hrs and then extracted with 3×50 mL of diethyl ether. The aqueous solution was evaporated to dryness, a portion of ethanol, acetonitrile: 1, 1 was added and the solution was reevaporated to dryness. The residue was pumped in vacuum at <1 mm Hg for 3 days with occasional gentle heating to provide 12.90 g (~Quantitative crude yield) of product 33 as a golden-yellow foam. TLC (silica; $CH_2Cl_2$, methanol, conc. $NH_4OH$: 27, 3, 1) Rf=0.50.

Example 59

Preparation of D,L-α-Benzyl-α-(carbobenzyloxy) amino-ε-caprolactam (34)

To a solution of crude 33 (12.90 g, ~0.0476 mol) in 100 mL of THF and 100 mL of saturated $NaHCO_3$ solution was added N-(Benzyloxycarbonyloxy)-succinimide (12.46 g, 0.050 mol) rapidly over 2 min. The solution was stirred from 0° to ambient temperature over 14 hrs and the THF was evaporated. Solid NaCl was added to the remaining aqueous layer and it was extracted with 1×200 mL and 2×100 mL of ethyl acetate. The combined organic layers were extracted with 50 mL portions of water (2×), brine, dried over $MgSO_4$, filtered, and evaporated. The crude product was purified by flash silica gel chromatography using a hexane, ethyl acetate: 4, 1 to 1, 1 gradient system and afforded 13.19 g (79% yield) of product 34 as a colorless solid, mp 129–130°, TLC (silica; ethyl acetate, hexane: 2, 1) Rf=0.35.

Example 60

Preparation of D,L-3-Benzyl-3-(carbobenzyloxy) amino-hexahydro-2-oxo-azepine-1-acetic acid, tert-butyl ester (35) OR D L-Cbz-α-Benzyl-norLeu (cyclo)Gly-O-t-Bu (35)

To a solution of 34 (1.616 g, 4.59 mmol) in 19 mL of anhydrous THF at room temperature under $N_2$ was added lithum bis-(trimethylsilyl)amide (5.51 mL of 1M THF solution, 5.51 mmol) rapidly dropwise over 10 min so as to maintain ~27°. The resultant dark yellow solution was stirred at ambient temperature for 30 min and a solution of tert-butyl bromoacetate (1.074 g, 5.51 mL, 0.81 mL) in 7 mL of anhydrous THF was added dropwise over 10 min. The solution was stirred at ambient temperature for 20 hrs, quenched with 10 mL of saturated $NH_4Cl$ solution, diluted with 100 mL of ethyl acetate and the organic phase was extracted with 25 mL portions of water (2×), brine (2×), dried over $MgSO_4$, filtered and evaporated. The residue was purified by flash silica gel chromatography using hexane, ethyl acetate: 9, 1 as eluent and afforded 1.290 g (60% yield) of product 35 as a viscous yellow oil. TLC (silica; hexane, ethyl acetate: 1, 1) Rf=0.50.

Example 61

Preparation of D, L-3-Benzyl-3-(carbobenzyloxy) amino-hexahydro-2H-2-oxo-azepine-1-acetic acid. (36) OR D,L-Cbz-α-Benzyl-norLeu(cyclo)Gly-OH (36)

To a solution of 35 (1.2603 g, 2.70 mmol) in 15 mL of $CH_2Cl_2$ at 0° was added 6 mL of trifluoroacetic acid. After 10 min at 0°, the ice bath was removed and the solution was stirred at ambient temperature for 1 hr. The solvents were evaporated and the residue was purified by flash silica gel chromatography using $CH_2Cl_2$, ethanol: 9, 1 as eluent and afforded 887.8 mg (80% yield) of product 36 as a colorless, amorphous solid. TLC (silica; $CH_2Cl_2$, methanol, acetic acid: 27, 3, 1) Rf=0.57.

Example 62

Preparation of N-[D. L-3-Benzyl-3-(carbobenzyloxy)aminohexahydro-2-oxo-azepine-1-acetyl]-$N^g$-nitro-L-argininal ethyl cyclol (37) OR D, L-Cbz-α-benzyl-norLeu(cyclo)Gly-$N^g$-nitro-L-argininal ethyl cyclol (37)

To a solution of 36 (872.8 mg, 2.126 mmol) in 22 mL of anhydrous acetonitrile at room temperature under $N_2$ was added $N^g$-nitro-L-argininal ethyl cyclol (683.0 mg, 2.55 mmol), 1-hydroxybenzotriazole hydrate (325.6 mg, 2.126 mmol) and 1-ethyl-3-(3-dimethylaminopropyl) carbodiimide hydrochloride (611.0 mg, 3.19 mmol). After stirring the mixture for 15 min, N,N-diisopropylethylamine (1.099 g, 8.50 mmol, 1.48 mL) was added and the resultant clear light brown solution was stirred at room temperature for 18 hrs. The reaction was diluted with 200 mL of ethyl acetate, extracted with 25 mL portions of 0.1N HCl (2×), saturated $NaHCO_3$ (2×), water, brine, dried over $MgSO_4$, filtered and evaporated. The crude product was purified by flash chromatography on silica gel using an ethyl acetate, hexane: 2,1 to ethyl acetate gradient system to afford 967.2 mg (73% yield) of product 37 as a colorless foam. TLC (silica; ethyl acetate) Rf=0.25.

Example 63

Preparation of N-[D, L-3-Amino-3-benzyl-hexahydro-2-oxo-azepine-1-acetyl]-L-argininal ethyl cyclol, diacetate salt (38) OR D, L-α-Benzyl-norLeu(cyclo)Gly-L-argininal ethyl cyclol, diacetate salt (38)

To a solution of 37 (960.2 mg, 1.54 mmol) in 100 mL of ethanol, acetic acid, water: 4, 1, 1 was added 10% Pd/C (480 mg). The mixture was hydrogenated at 55 PSI on a Parr shaker apparatus for 21 hrs, filtered and the solvents were evaporated. The residue was dissolved in ethanol, acetonitrile: 1, 1, reevaporated, and pumped at <1 mm Hg on a vacuum pump for 24 hrs to afford 856.7 mg (99% crude yield) of product 38 as a yellow foam. TLC (silica; $CH_2C_{12}$, methanol, conc $NH_4OH$: 20, 10, 2) Rf=0.40, 0.35 (2 isomers).

Example 64

Preparation of N-[D,.L-3-Amino-3-benzyl-hexahydro-2-oxo-azepine-1-acetyl]-L-argininal, bis-trifluoroacetate salt (39) OR D. L-α-Benzyl-norLeu (cyclo)Gly-L-argininal bis-trifluoroacetate salt (39)

Compound 38 (840.0 mg, 1.49 mmol) was added to 50 mL of 3 N HCl at ambient temperature. The solution was stirred for 3 hrs, filtered, and the filtrate was purified by reverse phase HPLC on a 50×300 mm C18 column using a 0–75% gradient of acetonitrile/water (containing 0.1% trifluoroacetic acid) over one hour and afforded 348.2 mg (36% yield) of product 39 as a colorless, amorphous solid. RP/HPLC analysis showed 5 peaks for the two isomeric products. Mass spectrometry confirmed the theoretical molecular weight of 416.

Examples 65 through 72(a) describe synthesis of N-[(S)-3-N-phenylethylamino-2-oxo-1-piperidineacetyl]-L-argininal, bis-trifluoroacetate salt (47). The synthesis scheme is shown in FIG. 12.

Example 65

Preparation of (S)-3-[(tert-Butoxycarbonyl)amino]-2-oxo-1-piperidineacetic acid, benzyl ester (40)

To a suspension of 21 (20.0 g, 0.0735 mol; see Example 46) in 700 mL of anhydrous acetonitrile and 30 mL of anhydrous N,N-dimethylformamide was added anhydrous, powdered $K_2CO_3$ (12.68 g, 0.0918 mol) followed by benzyl bromide (13.81 g, 0.0808 mol, 9.61 mL). The mixture was stirred and vigorously refluxed for 6 hrs, cooled, filtered, and evaporated. The residue was purified by flash chromatography on silica gel eluting with a gradient system of 40 to 50% ethyl acetate/hexane to afford 25.50 g (96% yield) of product 40 as a pale yellow oil; TLC (silica gel; ethyl acetate/hexane: 1,1 ): Rf=0.35.

Example 66

Preparation of (S)-3-Amino-2-oxo-1-piperidineacetic acid, benzyl ester hydrochloride (41)

To a solution of compound 40 (4.00 g, 0.0110 mole) in 10 mL of ethyl acetate at room temperature was added 5N HCl

Example 67

Preparation of (S)-3-Phenylethylamino-2-oxo-1-piperidineacetic acid, benzyl ester hydrochloride (42)

in 5 ethyl acetate (50 mL, freshly prepared, 0.25 mole) in one portion. The solution was stirred for 3 hrs, solvent was evaporated, $CH_2Cl_2$ was added and the solvents were reevaporated. The residue was pumped at <1 mm Hg on a vacuum pump for 24 hours to afford 3.37 g (~Quantitative crude yield) of product 41 as a colorless foam. TLC (silica gel; $CH_2Cl_2$, methanol, conc. $NH_4OH$: 27:3:1): Rf=0.32.

To a mixture of 41 (1.50 g, 5.02 mmol) and phenylacetaldehyde (0.724 g, 6.03 mmol) in 35 mL of 1,2-dichloroethane was added triethylamine (2.03 g, 21.1 mmol, 2.80 mL). After stirring at ambient temperature for 10 min, sodium triacetoxyborohydride (1.49 g, 7.03 mmol) was added rapidly over a 5 min period. The reaction mixture was stirred at room temperature for 15 hrs and quenched with 30 mL of water. The mixture was diluted with 50 mL of $CH_2Cl_2$ and the organic phase was separated, washed with 30 mL portions of saturated $NaHCO_3$, water, brine, dried over $MgSO_4$, filtered, and evaporated. The residue was purified by flash chromatography on silica gel eluting with $CH_2Cl_2$, ethanol: 95, 5 to afford 1.21 g (66% yield) of product 42 as a pale yellow oil; TLC (silica gel; $CH_2Cl_2$, ethanol: 9, 1): Rf=0.4

Example 68

Preparation of (S)-3-[N-(tert-Butoxycarbonyl)-N-phenylethylamino]-2-oxo-1-piperidineacetic acid, benzyl ester (43)

To a mixture of 42 (1.19 g, 3.23 mmol) in 10 mL of tetrahydrofuran and 10 mL of saturated $NaHCO_3$ solution was added di-tert-butyl dicarbonate (1.41 g, 6.47 mmole). The mixture was stirred at room temperature for 1.5 hrs, diluted with 150 mL of ethyl acetate and then extracted with 30 mL portions of saturated $NaHCO_3$ solution, 1N HCl, brine, dried over $MgSO_4$, filtered and evaporated. The residue was purified on flash silica gel chromatography using a gradient of hexane, ethyl acetate: 2, 1 and afforded 1.06 g (70% yield) of 43 as a colorless oil. TLC (silica; hexane, ethyl acetate: 2, 1) Rf=0.15.

Example 69

Preparation of (S)-3-[N-(tert-Butoxycarbonyl)-N-phenylethylamino]-2-oxo-1-piperidineacetic acid (44)

To a solution of 43 (1.06 g, 2.27 mmol) in 35 mL of methanol was added 10% Pd/C catalyst (127 mg) and the mixture was hydrogenated on a Parr shaker apparatus at 45 PSI for 2 hrs. The solution was filtered, evaporated, and the residue was dried by pumping at <1mm Hg vacuum for 10 hrs to afford 0.836 g (98% yield) of product 44 as a colorless foam. TLC (silica; $CH_2Cl_2$, methanol, acetic acid: 27, 3, 1) Rf=0.40.

Example 70

Preparation of N-[(s)-3-[N-(tert-Butoxycarbonyl)-N-phenylethylamino]-2-oxo-1-piperidineacetyl]-$N^g$-nitro-L-argininal ethyl cyclol (45)

To a solution of 44 (836.0 mg, 2.22 mmol) in 20 mL of anhydrous acetonitrile at room temperature under $N_2$ was added $N^g$-nitro-L-argininal ethyl cyclol (712.0 mg, 2.66 mmol), 1-hydroxybenzotriazole hydrate (340.0 mg, 2.22 mmol) and 1-ethyl-3-(3-dimethylaminopropyl) carbodiimide hydrochloride (638.0 mg, 3.33 mmol). After stirring the mixture for 10 min, N,N-diisopropylethylamine (1.15 g, 8.88 mmol, 1.55 mL) was added and the resultant clear light brown solution was stirred at room temperature for 18 hrs. The solvent was evaporated and the residue was dissolved in 150 mL of ethyl acetate, extracted with 25 mL portions of 1N HCl (2×), saturated $NaHCO_3$ (2×), water, brine, dried over $MgSO_4$, filtered and evaporated. The crude product was purified by flash chromatography on silica gel using $CH_2Cl_2$, isopropanol: 95, 5 as eluent and afforded 1.305 g (99% yield) of product 45 as a colorless foam. TLC (silica; $CH_2Cl_2$, methanol, conc. $NH_4OH$: 25, 5, 1) Rf=0.65.

Example 71

Preparation of N-[(S)-3-[N-(tert-Butoxycarbonyl)-N-phenylethylamino]-2-oxo-1-piperidineacetyl]-L-argininal ethyl cyclol, trifluoroacetate salt (46)

To a solution of 45 (933.0 mg, 1.58 mmol) in 20 mL of ethanol, acetic acid, water: 4, 1, 1 was added 10% Pd/C (280 mg). The mixture was hydrogenated at 45 PSI on a Parr shaker apparatus for 20 hrs, filtered and the solvents were evaporated. The residue was purified by reverse phase HPLC on a 50×300 mm C18 column using a 5–75% gradient of acetonitrile/water (containing 0.1% trifluoroacetic acid) over one hour and afforded 668 mg (64% yield) of product 46 as a colorless, amorphous solid. TLC (silica; $CH_2Cl_2$, methanol, conc $NH_4OH$: 20, 10, 2) Rf=0.40.

Example 72(a)

Preparation of N-[(s)-3-N-phenylethylamino-2-oxo-1-piperidineacetyl]-L-argininal bis-trifluoroacetate salt (47)

Compound 46 (543.0 mg, 0.824 mmol) was added to 20 mL of 3N HCl at ambient temperature. The solution was stirred for 3 hrs, filtered, and the filtrate was purified by reverse phase HPLC on a 50×300 mm C18 column using a 0–75% gradient of acetonitrile/water (containing 0.1% trifluoroacetic acid) over one hour and afforded 334.0 mg (63% yield) of product 47 as a colorless, amorphous solid. RP/HPLC analysis showed 3 peaks for the product. Mass spectrometry confirmed the theoretical molecular weight of 416.

Example 72(b)

Preparation of N-[(S)-3-N-phenylpropylamino-2-oxo-1-piperidineacetyl]-L-argininal, bis-trifluoroacetate salt The title compound was synthesized following the procedures in Examples 67 through 72(a), except 3-phenylpropionaldehyde was used in place of phenylacetaldehyde. RP/HPLC analysis showed 3 peaks for the product. Mass spectrometry confirmed the theoretical molecular weight of 430.

Examples 73 through 80 describe synthesis of N-[(S)-3-N-Phenylethylamino-hexahydro-2-oxo-azepine-1-acetyl]-L-argininal, bis-trifluoroacetate salt (56). The synthesis scheme is shown in FIG. 13.

Example 73

Preparation of (S)-3-[(tert-butoxycarbonyl)amino]-hexahydro-2-oxo-1-azepineacetic acid, ethyl ester (49)

To a solution of the compound 48 (4.57 g, 0.020 mol; see Example 27) in 100 mL of anhydrous tetrahydrofuran at ambient temperature under a N₂ atmosphere was added lithium bis(trimethylsilyl)amide (26.0 mL of 1M solution in tetrahydrofuran, Aldrich, 0.026 mole) dropwise rapidly so as to maintain ~30°. The solution was stirred for 15 min and then a solution of ethyl bromoacetate (6.68 g, 0.040 mole, 4.44 mL) in 10 mL of anhydrous tetrahydrofuran was added rapidly so as to maintain ~32°. After 1 hr reaction time, the mixture was quenched with 50 mL of saturated ammonium chloride solution, diluted with 400 mL of ethyl acetate, and extracted with 2×50 mL water, 1×50 mL brine, dried over $MgSO_4$, filtered, and evaporated. The crude product was purified by flash chromatography on silica gel eluting with 2:1 hexane/ethyl acetate to afford 5.23 g (83% yield) of product 49 as a viscous yellow oil; TLC (silica gel; ethyl acetate, hexane: 1,1): Rf=0.4.

Example 74

Preparation of (S)-3-Amino-hexahydro-2-oxo-1-azepineacetic acid, ethyl ester hydrochloride (50)

To a solution of 49 (3.143 g, 0.0100 mole) in 20 mL of ethanol at 0° C. was added 12N HCl in ethanol (27.0 mL, 0.32 mol) in one portion. The solution was stirred at 0° for 5 min and then allowed to stir at ambient temperature for one hr. The solvent was evaporated, anhydrous acetonitrile (100 mL) was added and the solvent was reevaporated. The residue was pumped at <1 mm Hg on a vacuum pump for 20 hrs to afford 2.410 g (96% yield) of product 50 as a pale yellow foam. TLC (silica gel; $CH_2Cl_2$, methanol, conc. $NH_4OH$: 25, 5, 1): Rf=0.63.

Example 75

Preparation of (S)-3-Phenylethylamino-hexahydro-2-oxo-azepineacetic acid, ethyl ester (51)

To a mixture of 50 (6.00 g, 23.9 mmol) and phenylacetaldehyde (4.21 g, 35.0 mmol, 4.1 mL) in 170 mL of 1, 2-dichloroethane was added triethylamine (9.67 g, 95.6 mmol, 13.3 mL). After stirring at ambient temperature for 10 min, sodium triacetoxyborohydride (7.09 g, 33.5 mmol) was added rapidly portionwise over a 15 min period. The reaction mixture was stirred at ambient temperature for 21 hrs and quenched with 140 mL of water. The mixture was diluted with 170 mL of $CH_2Cl_2$ and the organic phase was separated, washed with 150 mL portions of saturated $NaHCO_3$, water, brine, dried over $MgSO_4$, filtered, and evaporated. The residue was purified by flash chromatography on silica gel eluting with $CH_2Cl_2$, ethanol: 97, 3 to afford 5.22 g (69% yield) of product 51 as a pale yellow oil; TLC (silica gel; $CH_2Cl_2$, methanol, conc. $NH_4OH$: 27, 3, 1): Rf=0.55

Example 76

Preparation of (S)-3-[N-(tert-Butoxycarbonyl)-N-phenylethylamino]-hexahydro-2-oxo-azepineacetic acid, ethyl ester (52)

To a mixture of 51 (5.22 g, 16.4 mmol) in 50 mL of tetrahydrofuran and 50 mL of saturated $NaHCO_3$ solution was added di-tert-butyl dicarbonate (7.16 g, 32.8 mmole). The mixture was stirred at room temperature for 2 hrs, diluted with 350 mL of ethyl acetate and then extracted with 50 mL portions of saturated $NaHCO_3$ solution, 1N HCl, brine, dried over $MgSO_4$, filtered and evaporated. The residue was purified on flash silica gel chromatography using hexane, ethyl acetate: 2, 1 as eluent and afforded 5.77 g (84% yield) of 52 as a pale yellow oil. TLC (silica; $CH_2Cl_2$, isopropanol: 95, 5) Rf=0.45.

Example 77

Preparation of (S)-3-[N-(tert-Butoxycarbonyl)-N-phenylethylamino]-hexahydro-2-oxo-azepineacetic acid (53)

To a solution of 52 (5.77 g, 13.8 mmole) in 70 mL of ethanol at room temperature was added 1M LiOH solution (31.0 mL, 31.0 mmol). The solution was stirred at ambient temperature for 2 hrs. Dowex 50×8–400 ($H^+$form, 15.0 g) was added and after stirring for 15 min the resin was filtered, washed with fresh ethanol, water: 1, 1 and the filtrate was evaporated. The residue was pumped in high vacuum at <1mm Hg for 20 hrs with occasional gentle heating to afford 5.08 g (94% yield) of product 53 as a colorless, amorphous solid. TLC (silica: $CH_2Cl_2$, methanol, acetic acid: 27, 3, 1) Rf=0.5.

Example 78

Preparation of N- [(S)-3-[N-(tert-Butoxycarbonyl)-N-phenylethylamino]-hexahydro-2-oxo-azepine-1-acetyl]1-$N^g$-nitro-L-argininal ethyl cyclol (54)

To a solution of 53 (1.50 g, 3.84 mmol) in 40 mL of anhydrous acetonitrile at room temperature under $N_2$ was added $N^g$-nitro-L-argininal ethyl cyclol (1.34 g, 4.99 mmol), 1-hydroxybenzotriazole hydrate (0.52 g, 3.84 mmol) and 1-ethyl-3-(3-dimethylaminopropyl) carbodiimide hydrochloride (1.10 g, 5.76 mmol). After stirring the mixture for 15 min, N, N-diisopropylethylamine (1.99 g, 15.4 mmol, 2.68 mL) was added and the resultant clear light brown solution was stirred at room temperature for 22 hrs. The solvent was evaporated and the residue was dissolved in 300 mL of ethyl acetate, extracted with 25 mL portions of 1N HCl (2×), saturated $NaHCO_3$ (2×), brine, dried over $NaSO_4$, filtered and evaporated. The crude product was purified by flash chromatography on silica gel eluting with a $CH_2Cl_2$, ethanol: 98, 2 to 96, 4 gradient system and afforded 1.64 g (71% yield) of product 54 as a colorless foam. TLC (silica; $CH_2Cl_2$, methanol, conc. $NH_4OH$: 25, 5, 1) Rf=0.7.

Example 79

Preparation of N-[(S)-3-[N-(tert-Butoxycarbonyl)-N-phenylethylamino]-hexahydro-2-oxo-azepine-1-acetyl]-L-argininal ethyl cyclol, acetate salt (55)

To a solution of 54 (1.64 g, 2.72 mmol) in 30 mL of ethanol, acetic acid, water: 4, 1, 1 was added 10% Pd/C (250 mg). The mixture was hydrogenated at 45 PSI on a Parr shaker apparatus for 19 hrs. Additional 10% Pd/C (1.00 g) was added and the hydrogenation was continued for a further 21 hrs. The solution was filtered and the solvents were evaporated.

The residue was dissolved in anhydrous acetonitrile and reevaporated. The residue was pumped in high vacuum at <1 mm Hg for 24 hrs and afforded 1.75 g (~Quantitative crude yield) of product 55 as a colorless, amorphous solid.TLC (silica; $CH_2Cl_2$, methanol, conc. $NH_4OH$: 20, 10, 2) Rf=0.45.

Example 80

Preparation of N- [(s)-3-N-Phenylethylamino-hexahydro-2-oxo-azepine-1-acetyl]-L-argininal, bis-trifluoroacetate salt (56)

Compound 55 (1.46 g, 2.36 mmol) was added to 50 mL of 3N HCl at ambient temperature. The solution was stirred for 3.5 hrs, filtered, and the filtrate was purified by reverse phase HPLC on a 50×300 mm C18 column using a 0–15% gradient of acetonitrile/water (containing 0.1% trifluoroacetic acid) over one hr and afforded 1.19 g (77% yield) of product 56 as a colorless, amorphous solid. RP/HPLC analysis showed 3 peaks for the product. Mass spectrometry confirmed the theoretical molecular weight of 430.

Example 81

General Procedure for Reaction of (S)-3-amino-2-oxopiperidine-1-acetic acid benzyl ester hydrochloride with Sulfonyl or Sulfamoyl Chlorides.

To a solution of the compound of Example 66 (8.96 g, 0.030 mole) in 300 mL dry acetonitrile is added the appropriate sulfonyl or sulfamoyl chloride listed in Example (0.033 mole) and the solution is cooled to 0° C. under $N_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed in Example 35, intermediates having the formula given below, with R defined as in Example 35, are made:

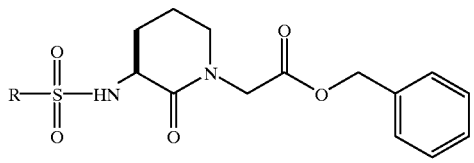

Example 82

General Procedure for Preparation of Compounds of the Present Invention.

Following the four-step protocol outlined in Examples 31 through 34 (hydrogenation, coupling, hydrogenation and hydrolysis), the intermediates of Example 81 were used to synthesize the following compounds of the present invention (as their trifluoroacetic acid salts):

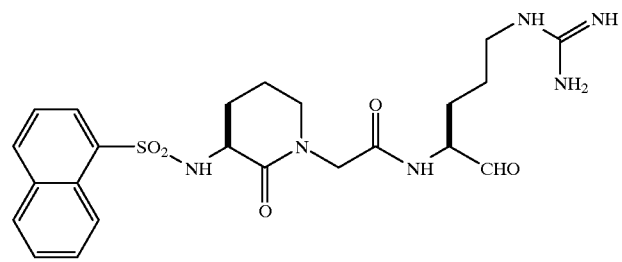

N-(1-naphthyl-SO2-norVal(cyclo)-Gly)-L-argininal (Compound 82(a))

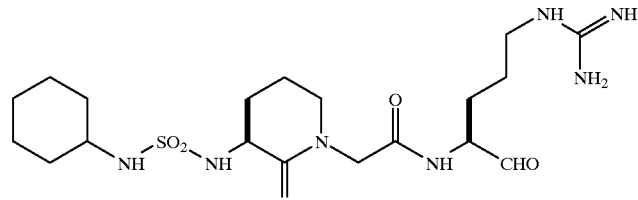

N-(cyclohexylamino-SO2-norVal(cyclo)-Gly)-L-argininal (Compound 82(b))

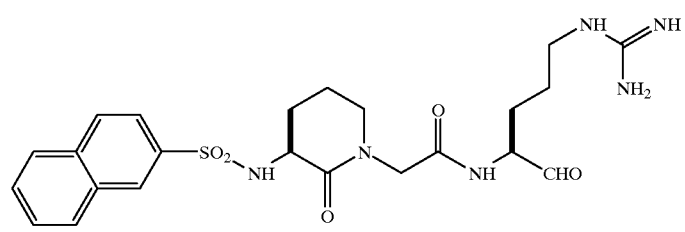

N-(2-naphthyl-SO2-norVal(cyclo)-Gly)-L-argininal (Compound 82(c))

-continued

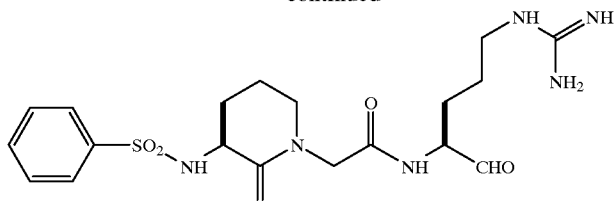

N-(phenyl-SO2-norVal(cyclo)-Gly)-L-argininal (Compound 82(d))

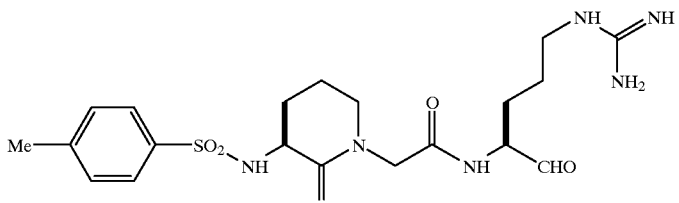

N-(4-methylphenyl-SO2-norVal(cyclo)-Gly)-L-argininal (Compound 82(e))

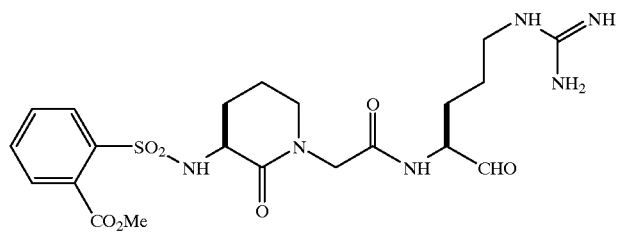

N-(2-carbomethoxyphenyl-SO2-norVal(cyclo)-Gly)-L-argininal (Compound 82(f))

Example 83

General Procedure for Reaction of (S)-3-amino 2-oxohexahydro-1-azepineacetic acid, benzyl ester hydrochloride with Phosphonochloridate Derivatives The substituted phosphonochloridates listed below are prepared by methods described in the literature, see H. J. Musiol, F. Grams, S. Rudolph-Bohner and L. Moroder, J. Org. Chem., 59: 6144–6146 (1994) and references cited therein. To a solution of the compound of Example 29 (9.38 g, 0.030 mole) in 300 mL dry acetonitrile is added the appropriate phosphonochloridate derivative listed below (0.033 mole) and the solution is cooled to 0° C. under $N_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed below, intermediates having the formula given below are made:

| $R_1$ = | R" = | Starting material | (amount needed) |
|---|---|---|---|
| benzyl | OEt | BnPO(OEt)(Cl) | (7.21 g) |
| benzyl | Me | BnPO(Me)(Cl) | (6.22 g) |
| benzyl | NHMe | BnPO(NHMe)(Cl) | (6.72 g) |
| benzyl | S-iPr | BnPO(S-i-Pr)(Cl) | (8.21 g) |

Example 84

General Procedure for Preparation of Compounds of the Present Invention

Following the four-step protocol outlined in Examples 31 through 34 (hydrogenation, coupling, hydrogenation and hydrolysis), the intermediates of Example 83 are used to synthesize the following compounds of the present invention (as their trifluoroacetate salts):

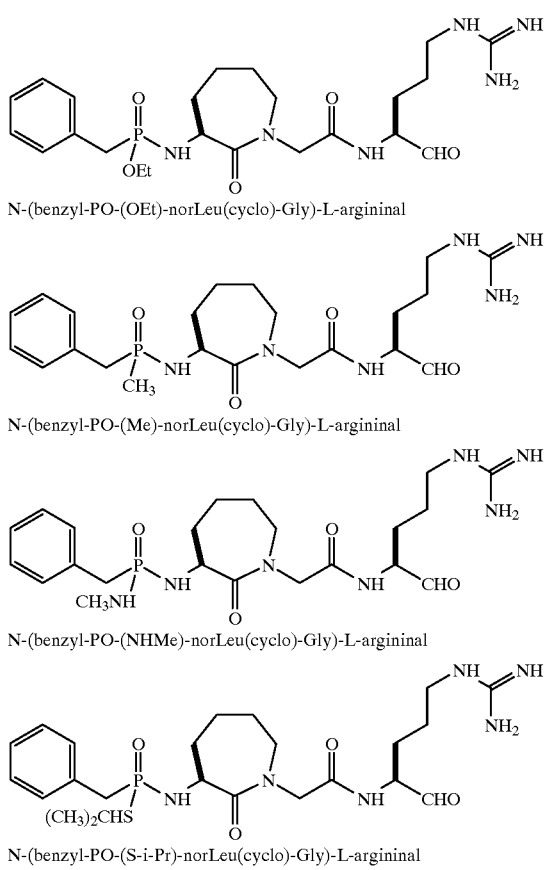

N-(benzyl-PO-(OEt)-norLeu(cyclo)-Gly)-L-argininal

N-(benzyl-PO-(Me)-norLeu(cyclo)-Gly)-L-argininal

N-(benzyl-PO-(NHMe)-norLeu(cyclo)-Gly)-L-argininal

N-(benzyl-PO-(S-i-Pr)-norLeu(cyclo)-Gly)-L-argininal

Example A

Kinetic Analysis of Compounds in an In Vitro Thrombin Inhibition Assay

The ability of the compound of Example 8, referred hereinafter as BzlSO$_2$-norVal(cyclo)-Gly-Arg-al, and the compound of Example 34, referred hereinafter as N-(BnSO$_2$-norLeu(cyclo)-Gly)-L-argininal, to act as an inhibitor of thrombin catalytic activity was assessed by determining its inhibition constant, Ki.

Enzyme activity was determined using the chromogenic substrate Pefachrome t-PA (CH3SO2-D-hexahydrotyrosine-glycyl -L-arginine-p-Nitroanilide), obtained from Pentapharm Ltd. The substrate was reconstituted in deionized water prior to use. Purified human alpha-thrombin (3000U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for Ki determinations was conducted by combining in appropriate wells of a Corning microtiter plate, 50 microliters of HBSA, 50 microliters of the test compound at a specified concentration diluted in HBSA (or HBSA alone for $V_{o(uninhibited\ velocity)}$ measurement), and 50 microliters of the chromogenic substrate (250 mM, 5 XKm) At time zero, 50 microliters of alpha-thrombin diluted in HBSA, was added to the wells yielding a final concentration of 0.5 nM in a total volume of 200 microliters. Velocities of chromogenic substrate hydrolysis which occurred over 40 minutes was measured by the change in absorbance at 405 nm using a Thermo Max® Kinetic Microplate Reader. Ki values were determined for test compounds using the relationships developed by Williams and Morrison, Methods in Enzymology, 63: 437 (1979) using steady state velocities (Vs) measured over 40 minutes. The extent of substrate hydrolysis was less than 5% over the course of this assay.

Table 1 below gives the Ki values for BzlSO$_2$-norVal (cyclo)-Gly-Arg-al and N-(BnSO$_2$-norLeu(cyclo)-Gly)-L-argininal. The data shows the utility of these compounds as potent in vitro inhibitors of human alpha-thrombin.

TABLE 1

| Compound | Ki (nM)* |
| --- | --- |
| BzlSO$_2$-norVal(cyclo)-Gly-Arg-al | 1.01 ± 0.272 |
| N-(BnSO$_2$-norLeu(cyclo)-Gly)-L-argininal | 0.538 ± 0.080 |

*Mean ± SD, n = 3

Example B

In vitro Enzyme Assays for Specificity Determination

The ability of compounds of this invention to act as a selective inhibitor of thrombin catalytic activity was assessed by determining the concentration of test compound which inhibited the activity of this enzyme by 50%, (IC$_{50}$), and comparing this value to that determined for some or all of the following related serine proteases: recombinant tissue plasminogen activator (rt-PA), plasmin, activated protein C (aPC), chymotrypsin and trypsin.

The buffer used for all assays was HBSA (10 mM HEPES, pH 7.5, 150 mM sodium chloride, 0.1% bovine serum albumin). The assay for IC$_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_o$ (uninhibited velocity) measurement), and 50 microliters of the enzyme diluted in HBSA. Following a 30-minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405nm using a Thermo Max® Kinetic Microplate Reader over a 5 minute period in which less than 5% of the added substrate was utilized. The concentration of added inhibitor which caused a 50% decrease in the initial rate of hydrolysis was defined as the IC$_{50}$ value.

1. Thrombin (fIIa) Assay

Enzyme activity was determined using the chromogenic substrate, Pefachrome t-PA (CH3SO2-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

IC$_{50}$ determinations were conducted where HBSA (50 μL), α-thrombin (50 μl) and inhibitor (50 μl) (covering a broad concentration range), were combined in appropriate wells and incubated for 30 minutes at room temperature prior to the addition of substrate Pefachrome-t-PA (50 μl). The initial velocity of Pefachrome t-PA hydrolysis was measured by the change in absorbance at 405nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

2. Recombinant tissue plasminogen activator (rt-PA)

rt-PA catalytic activity was determined using the substrate, Pefachrome t-PA (CH3SO2-D-hexahydrotyrosine-glycyl-L-arginine-p-nitroanilide, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

3. Plasmin Assay

Plasmin catalytic activity was determined using the chromogenic substrate, S-2251 (D-valyl-L-leucyl-L-lysine-p-nitroanilide), which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

4. Activated Protein C (aPC)

aPC catalytic activity was determined using the chromogenic substrate, Pefachrome PC (delta-carbobenzloxy-D-lysine -L-prolyl-L-arginine-p-nitroanilide), obtained from Pentapharm Ltd.). The substrate was made up in deionized water followed by dilution in HBSA prior to the assay in which the final concentration was 250 micromolar (about 3-times Km). Purified human aPC was obtained from Hematologic Technologies, Inc. The enzyme was diluted into HBSA prior to assay in which the final concentration was 1.0 nM.

5. Chymotryosin

Chymotrypsin catalytic activity was determined using the chromogenic substrate, S-2586 (methoxy-succinyl-L-arginine -L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3x-crystallized; CDI) bovine pancreatic a-chymotrypsin was obtained from Worthington Biochemical Corp. The enzyme was reconstituted in deionized water and diluted into HBSA prior to assay in which the final concentration was 1.0 nM.

6. Trypsin

Trypsin catalytic activity was determined using the chromogenic substrate, S-2222 (benzoyl-L-isoleucine-L-glutamic acid-(gamma-methyl ester)-L-arginine-p-nitroanilide), which was obtained from Kabi Diagnostica. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table 2 lists the determined $IC_{50}$ values for the enzymes listed above and demonstrates the high degree of specificity for the inhibition of alpha-thrombin compared to these related serine proteases.

7. Factor Xa

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 $\mu$M (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)].

TABLE 2

$IC_{50}$ values for the inhibition of human alpha thrombin amidolytic activity compared to selected serine proteases for N-(BnSO$_2$-norLeu(cyclo)-Gly)-L-argininal (Example 34; shown as column A), N-(cyclohexylmethylsulfonyl-norLeu(cyclo)-Gly-L-argininal (Example 36(i); shown as column B), and BzlSO$_2$-norVal(cyclo)-Gly-Arg-al (Examples 8 and 18; shown as column C).

| Enzyme | A $IC_{50}$ (nM) | B $IC_{50}$ (nM) | C $IC_{50}$ (nM) |
|---|---|---|---|
| alpha-thrombin | 0.93 | 4.54 | 12.4 |
| rt-PA | NI* | NI* | NI* |
| Plasmin | NI* | NI* | NI* |
| aPC | NI* | NI* | NI* |
| Chymotrypsin | NI* | NI* | NI* |
| Trypsin | 72 | 7.86 | 1550 |

*No inhibition observed at the maximal concentration of inhibitor assayed - 2500 nM.

Table 3, below, displays the specificity of compounds of this invention, having variable $R_1$ and X groups and ring size, with respect to thrombin, fxa and trypsin. The data demonstrate the thrombin specificity of the compounds.

TABLE 3

| Compound of Example No. | $R_1$-X group; Y is H unless specified | Ring size | $IC_{50}$ (nM) thrombin | $IC_{50}$ (nM) plasmin | $IC_{50}$ (nM) aPC | $IC_{50}$ (nM) rt-PA |
|---|---|---|---|---|---|---|
| 8, 18 | BnSO$_2$ | 6 | 6.2 | nd | >2500 | >2500 |
| 34 | BnSO$_2$ | 7 | 0.71 | nd | nd | nd |
| 36(a) | PhSO$_2$ | 6 | 159 | >2500 | >2500 | >2500 |
| 36(i) | ChxCH$_2$SO$_2$ | 7 | 4.54 | >2500 | nd | nd |
| 36(n) | PhNHSO$_2$ | 7 | 14.2 | >2500 | nd | nd |
| 36(p) | Bn(3-CF$_3$)SO$_2$ | 7 | 1.9 | >2500 | >2500 | >2500 |
| 36(q) | Bn(2-Me) | 7 | 1.71 | nd | nd | nd |

TABLE 3-continued

| Compound of Example No. | R₁-X group; Y is H unless specified | Ring size | IC$_{50}$ (nM) thrombin | IC$_{50}$ (nM) plasmin | IC$_{50}$ (nM) aPC | IC$_{50}$ (nM) rt-PA |
|---|---|---|---|---|---|---|
| 36(r) | Bn(3-Me) | 7 | 0.93 | nd | nd | nd |
| 55 | R₁-X group is H; Y is Bn | 6 | 5.41 | >2500 | >2500 | >2500 |
| 65 | R₁-X group is H; Y is Bn | 7 | 5.41 | >2500 | >2500 | >2500 |
| 72(a) | PhCH$_2$CH$_2$ | 6 | 3.09 | >2500 | >2500 | >2500 | nd means not determined

Example C

Ex Vivo Anticoaaulant Effects of Compounds in Rat and Human Plasma

The ex vivo anticoagulant effects of BzlSO$_2$-norVal (cyclo)-Gly-Arg-al (Example 8) and N-(BnSO$_2$-norLeu (cyclo)-Gly)-L-argininal (Example 34) were determined by measuring the prolongation of the activated partial thromboplastin time (APTT) over a broad concentration range of the added inhibitor, using pooled normal human and rat plasma.

Fresh frozen citrated pooled normal human plasma was obtained from George King Biomedical, Overland Park, Kans. Pooled normal rat plasma was prepared from citrated whole blood collected from anesthetized rats using standard procedures. The plasma was flash frozen and stored at −80° C. until use.

Figure 5:
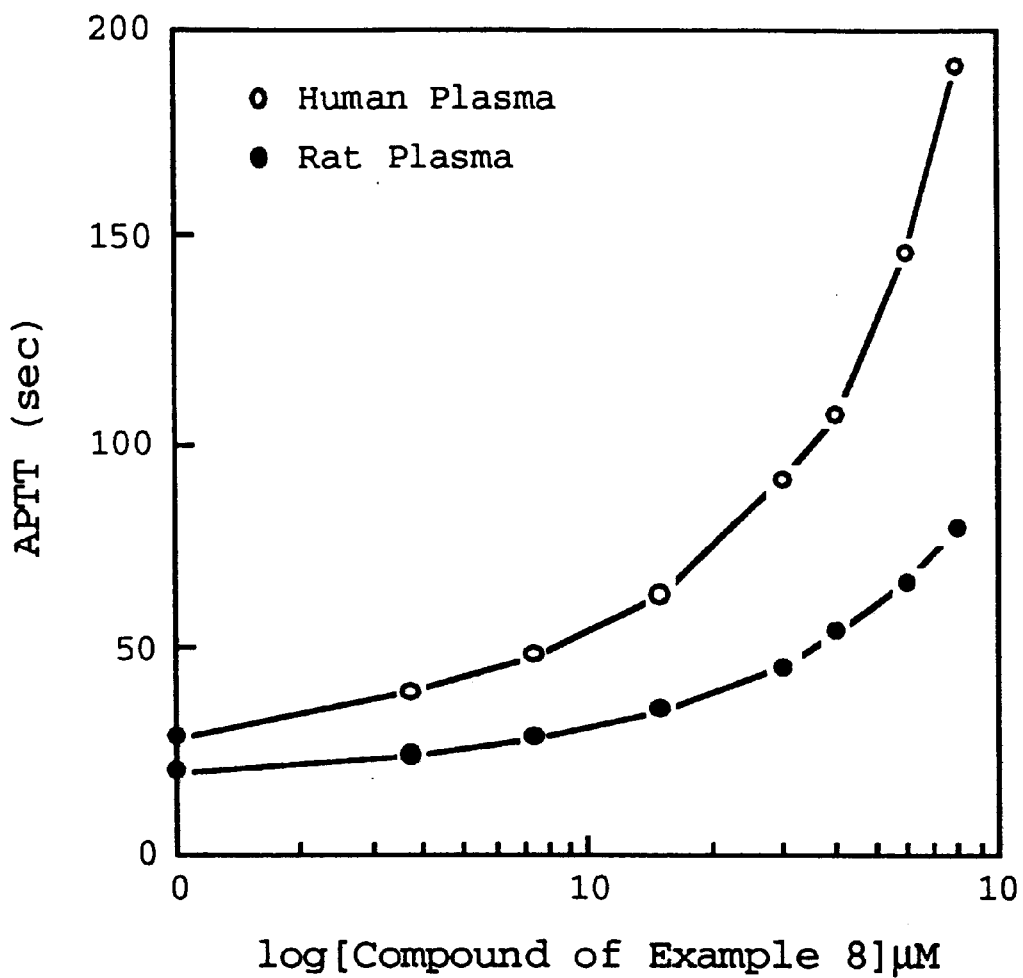
FIG. 5 depicts the anticoagulant effect of BzlSO$_2$-norVal (cyclo)-Gly-Arg-al measured in citrated rat (●) and human (○) plasma using the activated partial thromboplastin time (APTT) assay. The control clotting times (0 inhibitor) for rat and human plasma were 20 sec and 28 sec, respectively. The concentration of BzlSO$_2$-norVal(cyclo)-Gly-Arg-al which caused a doubling of the control clotting time in rat and human plasma was 22.1 micromolar and 12.8 micromolar, respectively. The data is the mean of two independent determinations.
Figure 7:
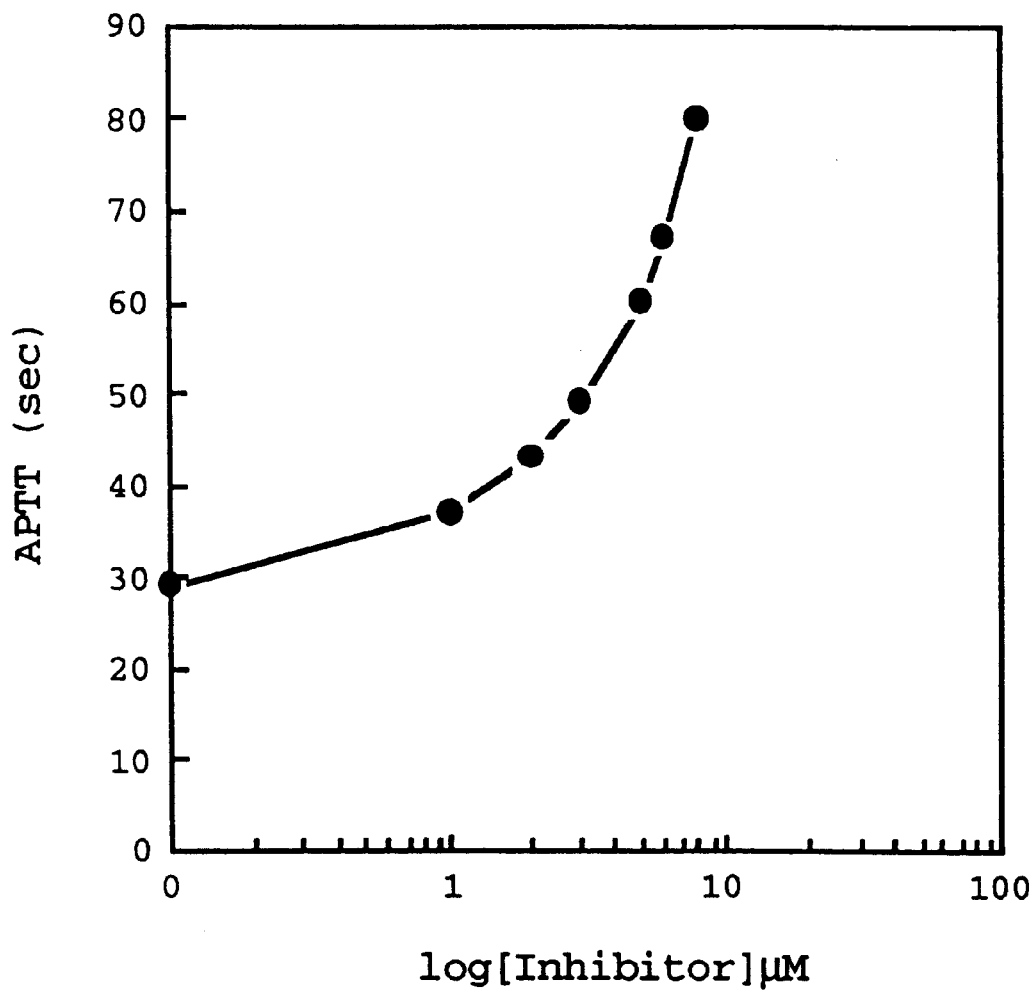
FIG. 7 depicts the anticoagulant effect of N-(BnSO2-norLeu(cyclo)-Gly)-L-argininal measured in citrated human plasma, closed circles (●), using the activated partial thromboplastin time (APTT) assay. The control clotting times (0 inhibitor) for human plasma was 29 seconds. The concentration of N-(BnSO$_2$-norLeu(cyclo)-Gly)-L-argininal which caused a doubling of the control clotting time in human plasma was 4.5 micromolar. The data is the mean of two independent determinations.

Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay was conducted by making a series of dilutions of the test compounds in rapidly thawed plasma followed by adding 200 microliters to the wells of the assay carousel. As shown in FIGS. 5 and 7, BzlSO$_2$-norVal(cyclo)-Gly-Arg-al and N-(BnSO$_2$-norLeu(cyclo)-Gly)-L-argininal, respectively, prolonged the APTT in a dose-dependent manner in both rat and human plasma demonstrating an anticoagulant effect in both species of mammals.

Example D

Evaluation of the Antithrombotic Potential of Compounds in an Experimental Rat Model of Thrombosis The antithrombotic (prevention of thrombus formation) properties of BzlSO$_2$-norVal(cyclo)-Gly-Arg-al (Example 8) and N-(BnSO$_2$-norLeu(cyclo)-Gly)-L-argininal (Example 34) were evaluated using the following established experimental model of acute vascular thrombosis.

Rat model of FeCl$_3$-induced Platelet-dependent Arterial Thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of FeCl$_3$ absorbed to a piece of filter paper. The FeCl$_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl$_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment group with test compound (BzlSO$_2$-norVal(cyclo)-Gly-Arg-al or N-(BnSO$_2$-norLeu (cyclo)Gly)-L-argininal) with at least 6 animals per group per dose. The test compound was administered as a single intravenous bolus at the doses outlined in Table 3 after placement of the flow probe and 5 minutes prior to the thrombogenic stimulus. At t=0, a 3 mm diameter piece of filter paper (Whatman #3) soaked with 10 microliters of a 35% solution of fresh FeCl$_3$ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point.

The efficacy of BzlSO$_2$-norVal(cyclo)-Gly-Arg-al and N-(BnSO$_2$-norLeu(cyclo)-Gly)-L-argininal as an antithrombotic agent in preventing thrombus formation in this in vivo model were demonstrated by the reduction in the incidence of thrombotic occlusion as shown in Tables 4 and 5, below.

TABLE 4

Results of BzlSO$_2$-norVal(cyclo)-Gly-Arg-al in the FeCl$_3$ Model of Thrombosis in Rats.

| Treatment Group | Dose (mg/kg) | n | Incidence of Occlusion |
| --- | --- | --- | --- |
| Saline | — | 6 | 6/6 |
| BzlSO$_2$-norVal(cyclo)-Gly-Arg-al | 0.3 | 6 | 6/6 |
| BzlSO$_2$-norVal(cyclo)-Gly-Arg-al | 1.0 | 6 | 2/6 |
| BzlSO$_2$-norVal(cyclo)-Gly-Arg-al | 3.0 | 6 | 1/6* |
| BzlSO$_2$-norVal(cyclo)-Gly-Arg-al | 5.0 | 6 | 0/6* |

*p $\leq$ 0.05 from saline control by Fishers test

TABLE 5

Results of the N-(BnSO$_2$-norLeu(cyclo)-Gly)-L-argininal in the FeCl$_3$ Model of Thrombosis in Rats.

| Treatment Group | Dose (mg/kg) | n | Incidence of Occlusion |
| --- | --- | --- | --- |
| Saline | — | 6 | 6/6 |
| N-(BnSO$_2$-norLeu(cyclo)-Gly)-L-argininal | 0.3 | 6 | 6/6 |
| N-(BnSO$_2$-norLeu(cyclo)-Gly)-L-argininal | 1.0 | 6 | 6/6 |
| N-(BnSO$_2$-norLeu(cyclo)-Gly)-L-argininal | 3.0 | 6 | 2/6 |
| N-(BnSO$_2$-norLeu(cyclo)-Gly)-L-argininal | 5.0 | 6 | 2/6 |

The effective dose which prevents 50% of thrombotic occlusions in this model (ED$_{50}$) can be determined from the above data by plotting the incidence of occlusion versus the dose administered. This allows a direct comparison of the antithrombotic efficacy of BzlSO$_2$-norVal(cyclo)-Gly-Arg-al and N-(BnSO$_2$-norLeu(cyclo)-Gly)-L-argininal with other antithrombotic agents which have also been evaluated in this model as described above. Table 6 lists the ED$_{50}$ values for several well known anticoagulant agents in this model compared to the present compounds.

TABLE 6

Efficacy of test compounds compared to other antithrombotic agents based on ED$_{50}$ for thrombus prevention in the FeCl$_3$ model of arterial thrombosis.

| Compound | ED$_{50}$[a] |
| --- | --- |
| Standard Heparin | 200 U/kg |
| Argatroban | 3.8 mg/kg |
| Hirulog ™ | 3.0 mg/kg |
| BzlSO$_2$-norVal(cyclo)-Gly-Arg-al | 0.75 mg/kg |
| N-(BnSO$_2$-norLeu(cyclo)-Gly)-L-argininal | 2.1 mg/kg |

[a]ED$_{50}$ is defined as the dose that prevents the incidence of complete thrombotic occlusion in 50% of animals tested.

The data presented in Table 6 clearly demonstrate the effectiveness of the present compounds in preventing occlusive thrombus formation in this experimental model. The relevance of this data to preventing human thrombosis can be inferred from the comparison to the other anticoagulant agents listed in this table which have been evaluated in an identical manner in this experimental model and have demonstrated antithrombotic efficacy in preventing thrombus formation clinically as described in the following literature citations: Heparin-Hirsh, J. N. Engl. J. Med., 324: 1565–1574 (1992), Cairns, J. A. et. al. Chest, 102: 456S–481S (1992); Argatroban-Gold, H. K. et.al., J. Am. Coll. Cardiol., 21: 1039–1047 (1993); and Hirulog™-Sharma, G. V. R. K. et.al., Am. J. Cardiol., 72: 1357–1360 (1993) and Lidon, R. M. et.al., Circulation, 88: 1495–1501 (1993). The in vivo comparison of compounds of the present invention with the clinically effective antithrombotic agents Standard Heparin, Argatroban, and Hirulog™ in the same rodent model of experimental thrombosis coupled with the demonstrated anticoagulant effects of the present compounds in both rat and human plasma described above in Example C would lead one skilled in the art to conclude that this compound will be an effective antithrombotic agent in humans.

Example E

Oral Activity of Compounds

The pharmacodynamic and pharmacokinetic parameters of the compound of Example 34 were evaluated after oral administration in dogs. Adult beagle dogs (9–12 kg) were housed individually in standard cages, and were fed a standard certified commercial diet and tap water ad libitum. Dogs were given an oral dose of 20 mg/kg test compound, in 55 ml deionized water, via a gastric tube, followed by a water rinse. In a separate protocol, 5 mg/kg of test compound, in 5 ml 0.9% sodium chloride, were administered by fast bolus i.v. injection through an indwelling saphenous vein catheter. The same dogs were used for both routes of administration, with a one week wash out period between use of the dogs for the different protocols.

Blood samples were collected during the experimental period from the cephalic vein using sodium citrate (0.38% final concentration) as anticoagulant (nine volumes blood to one volume sodium citrate). After mixing with the anticoagulant, each blood sample was immediately chilled by immersion in a slurry of ice and water. The plasma was separated by centrifugation (4° C., 2400 rpm, 10 min) within 10 min of collection, and then transferred to a cryotube and stored at 70° C. until analysis.

The blood levels of test compound were measured by extracting the compound from plasma, separation by HPLC, and post-column derivatization with a fluorogenic functional group. The clotting time of blood was measured using an APTT assay, which measures the prolongation of the activated partial thromboplastin time (APTT) by the test compound. Fresh frozen pooled normal citrated human plasma was obtained from George King Biomedical, Overland Park, Kans. Measurements of APTT were made using the Coag-A-Mate RA4 automated coagulometer (General Diagnostics, Organon Technica, Oklahoma City, Okla.) using the Automated aPTT Platelin® L reagent (Organon Technica, Durham, N.C.) as an initiator of clotting according to the manufacturers instructions. The assay was conducted by making a series of dilutions of each blood sample in rapidly thawed plasma followed by adding 200 microliters APTT reagent to the wells of the assay carousel.

The systemic bioavailability of the test compound administered by the oral route was calculated by comparing the AUC values (area under curve describing level of compound in blood over time) after i.v. and oral administration. Overall, the administered test compound demonstrated an approximately 66% bioavailability value (ratio of AUC oral to AUC i.v.), after corrections were made for difference in dose. Furthermore, the test compound of Example 34 was rapidly absorbed by the dogs, with significant elevation of APTT occurring within 20–30 min of oral dosing (both doses) and remaining high for up to two hours. The blood level of compound reached maximum levels 30–40 min after administration. The data demonstrated a good correlation ($r^2=0.64$) between plasma level of test compound and anticoagulant effect, as measured by APTT.

We claim:

1. A compound of the formula:

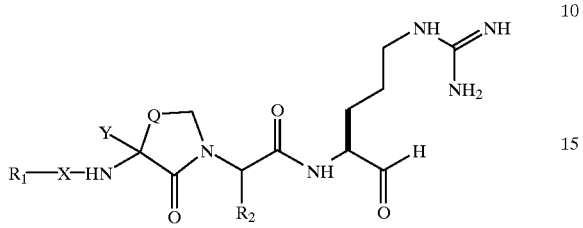

wherein (a) X is selected from the group consisting of —S(O)$_2$—N(R')—S(O)$_2$—, —(C=O)—, —OC(=O)—, —NH—C(=O)—, —P(O)(R")— and a covalent bond, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;

(b) R$_1$ is selected from the group consisting of:

(1) alkyl of 1 to about 12 carbon atoms, (2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which having 1 to about 3 carbons, (3) cyclic alkyl of 3 to about 15 carbon atoms, which optionally is substituted in the ring carbons with hydroxyl, amino, guanidino, amidino, or alkoxyl or alkyl each of which having 1 to about 3 carbons, (4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which having 1 to about 3 carbons, amino, guanidino, or amidino, (5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which having 1 to about 3 carbons, amino, guanidino, or amidino, (6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which having 1 to about 3 carbons, (7) aryl of about 6 to about 14 carbon atoms which is optionally mono-, di- or tri-substituted with Y$_1$, Y$_2$, and/or Y$_3$, respectively, (8) heteroaryl of 5 to 14 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively, (9) aralkyl of about 7 to about 15 carbon atoms which is optionally mono-, di-, or tri-substituted in the aryl ring with Y$_1$, Y$_2$, and/or Y$_3$, respectively,

(10) heteroaralkyl of 6 to 11 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively,

(11) aralkenyl of about 8 to about 15 carbon atoms which is optionally mono-, di-, or tri-substituted in the aryl ring with Y$_1$, Y$_2$, and/or Y$_3$, respectively,

(12) heteroaralkenyl of 7 to 12 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively,

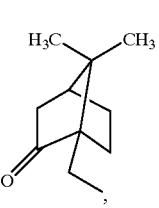
(13)

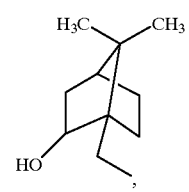
(14)

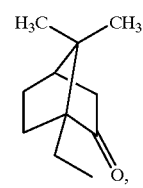
(15)

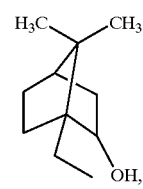
(16)

(17) perfluoroalkyl of 1 to about 12 carbon atoms,

(18) perfluoroaryl of about 6 to about 14 carbon atoms,

(19) perfluoroaralkyl of about 7 to about 15 carbon atoms,

(20) hydrogen, and (21)

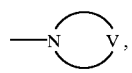

wherein

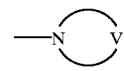

is a 5 to 7 member heterocycle of 3 to 6 ring carbon atoms, where V is —$CH_2$—, —O—, —S(=O)—, —S(O)$_2$— or —S—, wherein $Y_1$, $Y_2$, and $Y_3$ are
(i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —C(O)OH, —$C(O)NH_2$, —$C(O)NHZ_1$, —$C(O)OZ_1$, —$P(O)_3H$, —$P(O)_3H_2$, —$P(O)_3(Z1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$, and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) $Y_1$ and $Y_2$ are selected together to be —$OC(Z_3)(Z_4)O$—, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms,
(c) Q is —$(CH_2)_n$—, wherein n is an integer from 1 to 4, or —$(CH_2)_qR_4$—, wherein q is 1 or 2, and $R_4$ is —$S(O)_p$—, —O—, —$N(R_5)$—, wherein p is 0, 1, or 2 and $R_5$ is selected from the group consisting of hydrogen, alkyl of 1 to 4 carbon atoms, and aryl of 1 to 4 carbon atoms;
(d) $R_2$ is selected from the group consisting of hydrogen, alkyl of 1 to 4 carbon atoms or alkenyl of 2 to 4 carbon atoms; and
(e) Y is selected from the group of $R_1$ substituents, with the proviso that Y is not

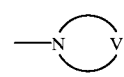

or a pharmaceutically acceptable salt thereof.

2. A compound according to claim 1, wherein X is selected from the group consisting of a covalent bond, —$SO_2$—, —NH—$S(O)_2$—, and —N(R')—$S(O)_2$—.

3. A compound according to claim 2, wherein X is a covalent bond or —$SO_2$—.

4. A compound according to claim 1, wherein $R_1$ is selected from the group consisting of alkyl, aralkyl and aryl.

5. A compound according to claim 4, wherein $R_1$ is selected from the group consisting of substituted or unsubstituted phenyl or naphthyl.

6. A compound according to claim 5, wherein $R_1$ is substituted with a substituent selected from the group consisting of —C(O)OH, —$C(O)OZ_1$, —$CH_3$, —$OCH_3$, and —$CF_3$.

7. A compound according to claim 4, wherein $R_1$ is aralkyl.

8. A compound according to claim 1, wherein Y is selected from the group consisting of:
(a) hydrogen,
(b) phenyl-$(CH_2)_i$—, wherein i is an integer from 0 to 3, and the phenyl is optionally mono-, di-, or tri-substituted with with $Y_1$, $Y_2$, and/or $Y_3$, respectively,
(c) heteroaryl-$(CH_2)_i$—, wherein i is an integer from 0 to 3, and the heteroaryl is optionally mono-, di-, or tri-substituted with $Y_1$, $Y_2$, and/or $Y_3$, respectively,
(d) heterocycloalkyl —$(CH_2)_i$—, wherein i is an integer from 0 to 3, and the heterocycloalkyl is optionally substituted with hydroxyl or, alkoxyl or alkyl, each of which having 1 to about 3 carbons,
(e) $C_5$ to $C_8$ cycloalkenyl, optionally substituted with $Z_5$, $Z_6$, and/or $Z_7$, and
(f) $C_5$ to $C_8$ cycloalkyl, optionally mono-, di-, or tri-substituted with with $Z_5$, $Z_6$, and/or $Z_7$, respectively, wherein $Z_5$, $Z_6$, and/or $Z_7$ are independently selected from the group consisting of $R_5$, $OR_5$, and $CO_2R_5$, wherein $R_5$ is selected from the group consisting of hydrogen, methyl, and alkyl of 1–3 carbon atoms,
(g) $(CH_2)_b$—$Z_5$, wherein b is 0 to 6 and $Z_5$ is as defined above.

9. A compound according to claim 8, wherein Y is aralkyl or cycloalkyl.

10. A compound according to claim 1, wherein X is —$S(O)_2$—, $R_1$ is substituted or unsubstituted aralkyl, Q is —$(CH_2)_2$— and $R_2$ is hydrogen.

11. A compound according to claim 10, wherein $R_1$ is substituted or unsubstituted benzyl.

12. A compound according to claim 1, wherein X is —$S(O)_2$—, $R_1$ is substituted or unsubstituted aralkyl, Q is —$(CH_2)_3$— and $R_2$ is hydrogen.

13. A compound according to claim 12, wherein $R_1$ is substituted or unsubstituted benzyl.

14. A compound according to claim 1 wherein X is —$S(O)_2$—.

15. A compound according to claim 14 wherein Q is —$CH_2$—.

16. A compound selected from the group consisting of:
(a) N-benzylsulfonyl-norVal(cyclo)-Gly-L-argininal,
(b) N-(norVal(cyclo)-Gly)-L-argininal,
(c) D-α-benzyl-norVal(cyclo)Gly-L-argininal,
(d) D-α-benzyl-norLeu(cyclo)Gly-L-argininal,
(e) N-(1-naphthyl-$SO_2$-norVal (cyclo)-Gly-L-argininal,
(f) N-(BnSO$_2$-norLeu (cyclo)-Gly)-L-argininal,
(g) N-(2-carbomethoxybenzyl-$SO_2$-norLeu (cyclo)-Gly)-L-argininal,
(h) N-(2-trifluoromethylbenzyl-$SO_2$-norLeu(cyclo)-Gly)-L-argininal,
(i) N-(cyclohexylmethyl-$SO_2$-norLeu(cyclo)-Gly)-L-argininal,
(j) N-(2thiophenemethyl-$SO_2$-norLeu(cyclo)-Gly)-L-argininal, (k) N-(phenylamino-SO$_2$-norLeu(cyclo)-Gly)-L-argininal,
(l) N-(3-carbomethoxybenzyl-SO$_2$-norLeu(cyclo)-Gly)-L-argininal,
(m) N-(3-trifluoromethylbenzyl-SO$_2$-norLeu (cyclo)-Gly)-L-argininal,
(n) N-(2-methylbenzyl-SO$_2$-norLeu(cyclo)-Gly)-L-argininal,
(o) N-(3-mehtylbenzyl-SO$_2$-norLeu(cyclo)-Gly)-L-argininal,
(p) N-(3-methoxybenzyl-SO$_2$-norLeu(cyclo)-Gly)-L-argininal,
(q) N-(2-chlorobenzyl-SO$_2$-norLeu(cyclo)-Gly)-L-argininal,
(r) N-(2-methyl-5-fluorobenzyl-SO$_2$-norLeu(cyclo)-Gly)-L-argininal,
(s) N-(2-methyl-5-methoxybenzyl-SO$_2$-norLeu(cyclo)-Gly)-L-argininal,
(t) N-((S)-3-N-phenylethylamino-2-oxo-1-piperidineacetyl)-L-argininal,
(u) N-((S)-3-phenylpropylamino-2-oxo-1-pipidineacetyl)-L-argininal,
(v) N-((S)-3-N-phenylethylamino-hexahydro-2-oxo-azepine-1-acetyl)-L-argininal,
(w) L-α-benzyl-norVal(cyclo)Gly-L-argininal, and
(x) L-α-benzyl-norLeu(cyclo)Gly-L-argininal.

17. A mixture of diastereomers consisting of:
(a) D-α-Benzyl-norVal-(cyclo)Gly-L-argininal; and
(b) L-α-benzyl-norVal(cyclo)Gly-L-argininal.

18. A compound according to claim 1 which is a mixture of diastereomers consisting of:
(a) D-α-benzyl-norLeu(cyclo)Gly-L-argininal; and
(b) L-α-benzyl-norLeu(cyclo)Gly-L-argininal.

* * * * *